US012404291B2

(12) United States Patent
Thomas et al.

(10) Patent No.: US 12,404,291 B2
(45) Date of Patent: Sep. 2, 2025

(54) ANTIMICROBIAL AGENT

(71) Applicant: THE UNIVERSITY OF SHEFFIELD, Sheffield (GB)

(72) Inventors: James Anthony Thomas, Sheffield (GB); Kirsty Laura Smitten, Sheffield (GB)

(73) Assignee: The University of Sheffield, Sheffield (GB)

( * ) Notice: Subject to any disclaimer, the term of this patent is extended or adjusted under 35 U.S.C. 154(b) by 966 days.

(21) Appl. No.: 17/600,991

(22) PCT Filed: Apr. 2, 2020

(86) PCT No.: PCT/GB2020/050875
§ 371 (c)(1),
(2) Date: Oct. 1, 2021

(87) PCT Pub. No.: WO2020/201754
PCT Pub. Date: Oct. 8, 2020

(65) Prior Publication Data
US 2022/0162245 A1   May 26, 2022

(30) Foreign Application Priority Data

Apr. 4, 2019   (GB) ..................... 1904796

(51) Int. Cl.
*C07F 15/00*   (2006.01)
(52) U.S. Cl.
CPC ................. *C07F 15/0053* (2013.01)
(58) Field of Classification Search
CPC .... A61K 31/555; C07F 15/00; C07F 15/0053
USPC ........................................................ 514/185
See application file for complete search history.

(56) References Cited

FOREIGN PATENT DOCUMENTS

| CN | 101842519 A | 9/2010 |
|---|---|---|
| CN | 103819510 A | 5/2014 |
| CN | 104792842 A | 7/2015 |
| GB | 2483253 A | 3/2012 |
| WO | WO 2009050509 A2 | 4/2009 |
| WO | WO 2009/056348 A1 | 5/2009 |
| WO | 2010032056 A1 | 3/2010 |
| WO | WO 2012028874 A1 | 3/2012 |
| WO | WO 2013091014 A1 | 6/2013 |
| WO | WO 2014145428 A2 | 9/2014 |

OTHER PUBLICATIONS

Smitten et al., Using nanoscopy to probe the biological activity of antimicrobial leads that display potent activity against pathogenic, multidrug resistant, gram-negative bacteria, ACS Nano, 13, pp. 5133-5146 (Apr. 2019).*

Alatrash et al., Synthesis, DNA Cleavage Activity, Cytotoxicity, Acetylcholinesterase Inhibition, and Acute Murine Toxicity of Redox-Active Ruthenium(II) Polypyridyl Complexes, ChemMedChem, 2017, vol. 12, pp. 1055-1069 (Year: 2017).*
MX Application No. MX/a/2021/011902, Office Action dated Sep. 27, 2023.
Claudio Chiorboli et al., Photophysics of Dinuclear Ru(II) and Os(II) Complexes Based on the Tetrapyrido[3,2-a:2',3'-c:3",2"-3"'-j] (tpphz) Bridging Ligand, Inorg. Chem. 1999, 38, 2402-2410; https://doi.org/10.1021/ic981284f, Apr. 28, 1999) discloses the same mono- and dinuclear Ru complexes. (See Figure 1).
Nobuko Komatsuzaki et al., "Structure and photochemical properties of ruthenium complexes having dimethyl-substituted DPPZ or TPPHZ as a ligand", J. Chem. Soc. Dalton Trans., 2000, 3053-3054, https://doi.org/10.1039/B005428N, Aug. 23, 2000) also discloses the same mono- and dinuclear Ru complexes. (See Figure 2).
Fangfei Li et al, "Ruthenium complexes as antimicrobial agents", Chemical Society Reviews, vol. 44, No. 8, pp. 2529-2542, DOI: 10.1039/C4CS00343H, Jan. 1, 2015) also discloses mono- and dinuclear Ru complexes and the antibacterial properties of ruthenium complexes (see abstract figure 4; compound d, figure 9, compound a).
Simon D Fairbanks et al, "Structural Investigation into the Threading Intercalation of a Chiral Dinuclear Ruthenium(II) Polypyridyl Complex through a B-DNA Oligonucleotide", Journal of the American Chemical Society, vol. 141, No. 11, pp. 4644-4652, DOI: '0.'01'/jacs.8b12280, Feb. 25, 2019) also discloses mono- and dinuclear Ru complexes. (See abstract).
Paul J. Jarman et al, "Exploring the Cytoxicity, Uptake, Cellular Response, and Proteomics of Mono- and Dinuclear DNA Light-Switch Complexes", Journal of the American Chemical Society, vol. 141, No. 7, pp. 2925-2937, DOI: 10.1021/jacs.8b0999, Dec. 30, 2018) also discloses mono- and dinuclear Ru complexes. (See abstract, scheme 1).
Indian Application No. 202117045047, Examination Report, dated Jun. 30, 2023.
Singapore Application No. 11202110640U Written Opinion dated Mar. 21, 2023, 8 pages.
EP Application No. 20718740.2 Examination Reported dated Jan. 16, 2023, 5 pages.
Eurasian Patent Application No. 202192590/28, Conclusion on the Patentability of the Invention, dated Apr. 28, 2023, 4 pages.
Chemical Society Reviews, vol. 44, No. 8, Jan. 1, 2015 (pp. 2529-2542, XP055706232, UK, ISSN 0306-012, DOI: 10.1039/C4Cs00343H.

(Continued)

*Primary Examiner* — Jeffrey H Murray
*Assistant Examiner* — Rilla Marie Samsell
(74) *Attorney, Agent, or Firm* — Lathrop GPM LLP; Laura A. Labeots

(57) ABSTRACT

A compound according to formula (I) or formula (Ia), and a composition comprising the compound for use as an antimicrobial: wherein, $X_1$, $X_2$, $X_3$ and $X_4$ are each independently selected from: N, O, S; $Y_1$ and $Y_2$ are each independently selected from: N, O, S, $C(R_a)$; $M_1$ and $M_2$ are each a metal centre; $R_1$, $R_2$, $R_3$, $R_4$ and Ra are each independently selected from: hydrogen, alkyl, alkenyl, aryl, halogen, haloalkyl, haloalkenyl, haloaryl, hydroxy, alkoxy, carboxylic acid, amino, amido, nitro or combination thereof; $A_1$, $A_2$, $A_3$ and $A_4$ are each bidentate ligands; and rings $D_1$ and $D_2$ are each independently comprise one or more heteroatoms selected from N, O, S, $C(R_a)$; wherein said compound is for use as an antimicrobial.

17 Claims, 27 Drawing Sheets

(56) References Cited

OTHER PUBLICATIONS

Journal of the American Chemical Society, vol. 141, No. 11, Feb. 25, 2019, p. 4644-4652, XP055706247, US, ISSN 0002-7863, DOI 10/1021/jacs.
Jounral of the American Chemical Society, vol. 141, No. 7, Dec. 30, 2018, pp. 2925-2937, XP055706254, US ISSN 0002-7863, DOI 10/1021/jacs.8b09999.
PCT/GB2020/050875 International Search Report and Written Opinion dated Jun. 26, 2020, 14 pages.
GB1904796.8 Combined Search and Examination Report dated Sep. 10, 2019, 8 pages.
Li, F, et al.: "Ruthenium complexes as antimicrobial agents", Chemical Society Reviews, vol. 44, No. 8, Jan. 1, 2015, pp. 2529-2542.
Alatrash et al., "Synthesis, DNA Cleavage Activity, Cytotoxicity, Acetylcholinesterase Inhibition, and Acute Murine Toxicity of Redox-Active Ruthenium(II) Polypyridyl Complexes" ChemMedChem, Jul. 6, 2017;12(13):1055-1069.
Yadav, A. et al: "Regression of Lung Cancer by Hypoxia-Sensitizing Ruthenium Polypyridyl Complexes", Mol Cancer Ther; 12(5) May 2013, pp. 643-653.
Fairbanks, S.D. et al., "Structural Investigation into the Threading Intercalation of a Chiral Dinuclear Ruthenium(II) Polypyridyl Complex through a B-DNA Oligonucleotide", Journal Of The American Chemical Society, vol. 141, No. 11, Feb. 25, 2019, 9 pages.
Jarman, P.J. et al., "Exploring the Cytotoxicity, Uptake, Cellular Response, and Proteomics of Nono- and Dinuclear DNA Light-Switch Complexes", Journal Of The American Chemical Society, vol. 141, No. 7, Dec. 30, 2018, 15 pages.

\* cited by examiner

A

B

ANTIMICROBIAL AGENT

FIELD OF INVENTION

The invention relates to compounds for use in the treatment of microbial infections, specifically bacterial infections. Novel compounds are also described, methods of making said compounds and methods of treating diseases and disorders caused by antimicrobial infections.

BACKGROUND

Although polypyridyl Ru(II) complexes have been much studied as imaging probes and anticancer therapeutic leads, initial biological studies focused on their potential as antimicrobials. In work that was in many ways before its time, the Dwyer group demonstrated that lipophilic derivatives of $[Ru(phen)_3]^{2+}$ (phen=1,10 phenanthroline) containing methylated phenyl ligands are active against a range of bacteria, particularly Gram-positive species, which are unable to develop resistance to these structures. Since the minimum inhibitory concentrations (MIC) of these complexes were found to be relatively high compared to contemporary commercial antibacterials, this work was not further developed. However, in the modern context of a rapidly emerging global health crisis due to increasing antimicrobial resistance (AMR) the activity of such structures is being revisited.

It was recently found that tethering $[Ru(phen)_3]^{2+}$ units together using flexible methylene-based linkers of different lengths produces complexes with considerably higher activity (lower MICs). The mechanism of activity for these compounds is still being explored. It has been hypothesized that they accumulate at ribosomes, causing condensation of polysomes, but it has also been suggested that the cellular uptake and antibacterial activity of this class of compounds is due to their membrane-spanning ability. However, except for one notable example involving a mononuclear complex, these systems display lower activity against Gram-negative species such as *Escherichia coli*. Indeed, pathogenic Gram-negative species are a particularly pernicious AMR problem. For example, in its recent report, the World Health Organization declared that a post-antibiotic era is "a very real possibility for the 21st century" and identified Gram-negative *Pseudomonas aeruginosa, Acinetobacter baumannii*, and members of the Enterobacteriaceae that make up the majority of the ESKAPE group of serious hospital acquired infections as their three Priority 1 (Critical) pathogens in its "Priority Pathogens List For R&D". The urgency of the situation is exacerbated by the lack of new therapeutic leads: no new class of antibiotics for Gram-negative pathogens has been approved for over 50 years, and since 2010 only one new compound has entered the antibiotic pipeline through Phase 1 trials. This situation has prompted calls to increase chemical diversity in the search for chemical leads. It has also been suggested that the lack of completely new molecular "starting points leads" is the biggest roadblock for antibiotic discovery.

There has been some investigation of ruthenium complexes as imaging agents for bacterial species, in particular for use in confocal microscopy (see for instance, WO2009/050509). However, to date, no substantially efficacious ruthenium complexes have been discovered which could form the basis of a new class of antibiotics and/or antimicrobials.

The invention is intended to solve, or at least ameliorate, this problem.

SUMMARY OF INVENTION

There is provided, in a first aspect of the invention a compound according to formula (I) or formula (Ia):

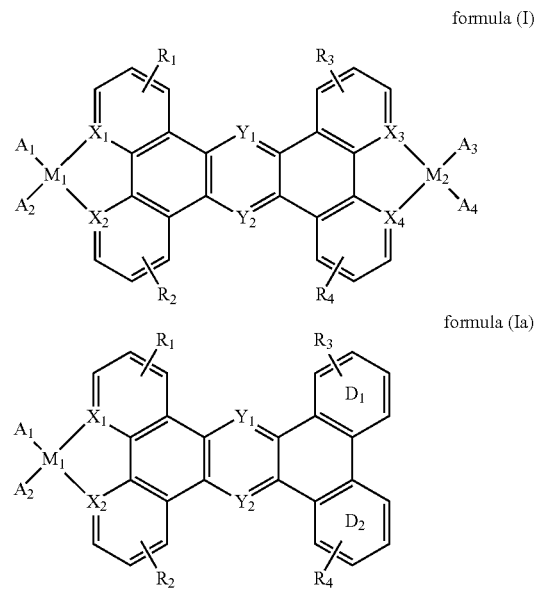

wherein,
$X_1, X_2, X_3$ and $X_4$ are each independently selected from: N, O, S;
$Y_1$ and $Y_2$ are each independently selected from: N, O, S, $C(R_a)$;
$M_1$ and $M_2$ are each a metal centre;
$R_1, R_2, R_3, R_4$ and $R_a$ are each independently selected from: hydrogen, alkyl, alkenyl, aryl, halogen, hydroxy, alkoxy, carboxylic acid, amino, amido, nitro or combination thereof; and
$A_1, A_2, A_3$ and $A_4$ are each bidentate ligands;
wherein rings $D_1$ and $D_2$ may each independently comprise one or more heteroatoms; and
wherein said compound is for use as an antimicrobial.

It has been found by the inventors that bidentate functionalised complexes according to formula (I) or formula (Ia) can not only function as effective imaging agents, but also provide remarkable antimicrobial properties. Without being bound by theory, it is hypothesised that these compounds initially damage cell membranes, attacking both outer and inner-membranes (tearing away and "blebbing" respectively). Moreover, it is believed, that compounds of formula (I) interact with cardiolipins, a double negatively charge lipid on the s-flap of the inner-membrane.

Regarding the compounds of formula (Ia), again without being bond by theory, it is believed that these compounds target DNA.

It is typically the case that said compounds of the first aspect of the invention are for use as antibiotics. Whilst these compounds may be used to treat a wide range of microbes, it has been found that compounds according to the first aspect of the invention are surprisingly effective against bacteria. This is especially true with respect to gram-negative bacteria, against which the compounds of the first aspect of the invention are particular effective. However, it is also envisaged that the claimed compounds may be useful against gram-positive bacteria.

There is no particular restriction as to the bacteria against which the compounds of the invention may be deployed. However, it is typically the case that the compounds of the first aspect of the invention are used to treat one or more bacterial species selected from: *E. coli, A. baumannii, B. cenocepacia, P. aureginosa, S. aureus, E. faecalis* and streptocccus.

For the avoidance of doubt, the term "alkyl" is intended to take its usual meaning and covers linear, branched and cyclic saturated hydrocarbons having a carbon length in the range $C_1$ to $C_{30}$. Often the alkyl group will be linear or branched, typically linear. Whilst the exact length of the alkyl group may vary, it is typically the case that the alkyl group has a carbon length in the range $C_1$ to $C_{20}$, more typically $C_1$ to $C_{12}$, more typically $C_1$ to $C_8$, and most typically $C_1$ to $C_6$. Typical alkyl groups are selected from, but not limited to: methyl, ethyl, propyl, isopropyl, butyl or tertiary butyl. Similarly, the term "alkoxy" is intended to carry its usual meaning i.e. this term is identical to "alkyl" described above with the exception that said alkyl group is covalently bonded via an oxygen atom (as would be familiar to one skilled in the art).

For the avoidance of doubt, the term "alkenyl" is intended to take its usual meaning and covers linear, branched and cyclic partially saturated hydrocarbons having a carbon length in the range $C_2$ to $C_{30}$. The term "partially saturated" refers to the presence of at least one C=C bond within the structure. Often the alkenyl group will be linear or branched, typically linear. Whilst the exact length of the alkenyl group may vary, it is typically the case that the alkenyl group has a carbon length in the range $C_2$ to $C_{20}$, more typically $C_2$ to $C_{12}$, more typically $C_2$ to $C_8$, and most typically $C_2$ to $C_6$. Typical alkenyl groups are selected from, but not limited to: vinyl, propenyl, isopropenyl or butenyl.

For the avoidance of doubt, each of the "alkyl" and "alkenyl" groups listed above may be optionally substituted. One or more optional substituents may be present and typical optional substituents are selected from: halogens, hydroxy, carboxylic acids, amines, amides, nitro or combinations thereof. Most typically, the optional substituents are halogens or hydroxy groups. In some embodiments, one or more hydrogen atoms may be replaced with a halogen.

For the avoidance of doubt, the term "aryl" is intended to take its usual meaning and covers groups of one or more aromatic ring species. Said aromatic rings may include, eight-membered rings, seven-membered rings, six-membered rings, and five-membered rings. More typically, the rings are six-membered rings or five-membered rings, and most typically the rings are six-membered rings. Moreover, one or more heteroatoms may be included within said rings to form heteroaryl species. Typical heteroatoms include N, O and S, more typically N and O, and most typically N. Where a heteroaryl group is used, it is usually the case that only one heteroatom is present. It is often the case that the aryl group is selected from: phenyl, cyclopentadienyl, pyridyl and furyl.

For the avoidance of doubt, the "aryl" group listed above may be optionally substituted. One or more optional substituents may be present and typical optional substituents are selected from: alkyl, alkoxy, alkenyl, halogens, hydroxy, carboxylic acids, amines, amides, nitro or combinations thereof. More typically, the optional substituents are alkyl, alkoxy, halogens or hydroxy groups, and even more typically the optional substituents are alkyl or alkoxy (usually alkyl). In some embodiments, one or more arbitrary hydrogen atoms may be replaced with a halogen.

For the avoidance of doubt, the term "halogen" is intended to take its usual meaning and often encompasses fluorine, chlorine, bromine and iodine. More typically, the halogen will be fluorine, chlorine or bromine; even more typically fluorine or chlorine; and most typically fluorine.

Moreover, the term "metal centre" is intended to refer to a metal atom (typically a metal ion) about which a complex can form in combination with suitable ligands. There is no particular restriction on the choice of metal, however the metal centre is typically capable of forming complexes with a hexagonal geometry i.e. it is capable of forming 6 bonds. Typically the metal centre(s) are transition metals.

The identity of $X_1$, $X_2$, $X_3$ and $X_4$ (i.e. whether N, O or S are employed) is to a large extent determined by the choice of metal centre that are used in the compound of formula (I) or formula (Ia), i.e. "$M_1$ and $M_2$" and "$M_1$" respectively. As will be appreciated, different metals have different affinities for different donor atoms. However, it is often the case that $X_1$, $X_2$, $X_3$ and $X_4$ are each independently N or O. Usually, at least one of $X_1$, $X_2$, $X_3$ and $X_4$ is N, more typically at least two of $X_1$, $X_2$, $X_3$ and $X_4$ are N, and even more typically at least three of $X_1$, $X_2$, $X_3$ and $X_4$ are N. However, most typically each of $X_1$, $X_2$, $X_3$ and $X_4$ are N.

In addition, whilst there is no real limitation on the identity of $Y_1$ and $Y_2$, i.e. whether N, O, S, $C(R_a)$ are used, it is often the case that $Y_1$ and $Y_2$ are each independently selected from N, O, $C(R_a)$ and more typically are each independently selected from N or $C(R_a)$. Usually, at least one of $Y_1$ and $Y_2$ is N. However, it is most often the case that both $Y_1$ and $Y_2$ are N.

With respect to compounds according to formula (Ia), each of rings $D_1$ and $D_2$ may each independently include one or more heteroatoms which are typically defined as for $X_3$ and $X_4$ above. In particular, $X_3$ and/or $X_4$ may be selected from C, N and O, more typically C and N, and most typically N. It may be the case that two or more heteroatoms are present within rings $D_1$ and/or $D_2$. Typically, the compound has a structure according to formula (Ib):

formula (Ib)

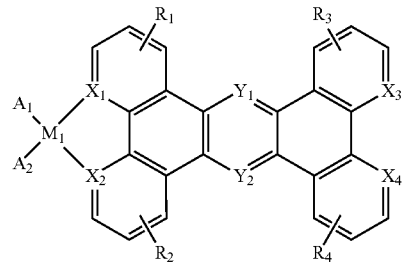

wherein,
$A_1$, $A_2$, $M_1$, $R_1$ to $R_4$, $Y_1$, $Y_2$, and $X_1$ to $X_4$ are as defined above.

The metal centres used in the compound of formula (I) and formula (Ia), $M_1$ and $M_2$, are not particularly limited provided that they are capable of forming a stable complex with the ligands of formula (I) and formula (Ia). Typical examples of metal centre include, but are not limited to: ruthenium, iridium, osmium, iron, platinum, rhodium, or combinations thereof. Often, $M_1$ and $M_2$, are selected from: ruthenium, iridium and osmium. Typically, at least one of $M_1$ and $M_2$ is ruthenium or iridium; more typically ruthenium. It may be the case that both $M_1$ and $M_2$ are ruthenium. In some embodiments, one or both metal centres, $M_1$ and $M_2$, may be iridium.

Typically, each of $R_1$, $R_2$, $R_3$ and $R_4$ is independently selected from: hydrogen, alkyl, alkenyl, aryl, halogen, hydroxy, alkoxy, carboxylic acid, amino, amido, nitro or a combination thereof. Each of $R_1$, $R_2$, $R_3$ and $R_4$ represents between one and three groups attached to the associated aromatic ring as would familiar to the person skilled in the art, i.e. as shown in formula (II) or formula (IIa):

formula (II)

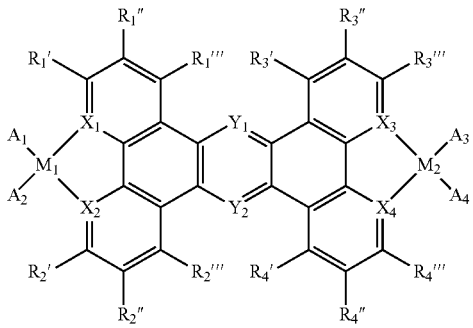

formula (IIa)

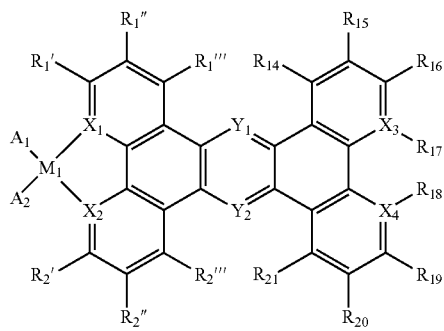

It is typically the case that $R_1$, $R_2$, $R_3$ and $R_4$ are each independently selected from: hydrogen, alkyl, alkenyl, aryl, halogen, hydroxy, alkoxy or combinations thereof. More typically, $R_1$, $R_2$, $R_3$ and $R_4$ are each independently selected from: hydrogen, alkyl, alkenyl, aryl or combinations thereof. Most typically, $R_1$, $R_2$, $R_3$ and $R_4$ are each independently selected from: hydrogen, alkyl, aryl or combinations thereof. Usually, at least one of $R_1$, $R_2$, $R_3$ and $R_4$ is hydrogen; more often, at least two of $R_1$, $R_2$, $R_3$ and $R_4$ are hydrogen; more typically still at least three of $R_1$, $R_2$, $R_3$ and $R_4$ are hydrogen; and most typically each of $R_1$, $R_2$, $R_3$ and $R_4$ are hydrogen.

Moreover, $R_{14}$, $R_{15}$, $R_{16}$, $R_{17}$, $R_{18}$, $R_{19}$, $R_{20}$ and $R_{21}$ are each independently selected from: hydrogen, alkyl, alkenyl, aryl, halogen, hydroxy, alkoxy or combinations thereof. More typically, $R_{14}$, $R_{15}$, $R_{16}$, $R_{17}$, $R_{18}$, $R_{19}$, $R_{20}$ and $R_{21}$ are each independently selected from: hydrogen, alkyl, alkenyl, aryl or combinations thereof. Most typically, $R_{14}$, $R_{15}$, $R_{16}$, $R_{17}$, $R_{18}$, $R_{19}$, $R_{20}$ and $R_{21}$ are each independently selected from: hydrogen, alkyl, aryl or combinations thereof. Usually, at least one of $R_{14}$, $R_{15}$, $R_{16}$, $R_{17}$, $R_{18}$, $R_{19}$, $R_{20}$ and $R_{21}$ is hydrogen; more often, at least two of $R_{14}$, $R_{15}$, $R_{16}$, $R_{17}$, $R_{18}$, $R_{19}$, $R_{20}$ and $R_{21}$ are hydrogen; more typically still at least three of $R_{14}$, $R_{15}$, $R_{16}$, $R_{17}$, $R_{18}$, $R_{19}$, $R_{20}$ and $R_{21}$ are hydrogen; even more typically still at least four of $R_{14}$, $R_{15}$, $R_{16}$, $R_{17}$, $R_{18}$, $R_{19}$, $R_{20}$ and $R_{21}$ are hydrogen; and most typically at least five of $R_{14}$, $R_{15}$, $R_{16}$, $R_{17}$, $R_{18}$, $R_{19}$, $R_{20}$ and $R_{21}$ are hydrogen. Usually, $R_{14}$, $R_{15}$, $R_{16}$, $R_{17}$, $R_{18}$, $R_{19}$, $R_{20}$ and $R_{21}$ are each hydrogen. As will be appreciated, where $X_3$ or $X_4$ are heteroatoms (such as nitrogen or oxygen), it may be the case that $R_{17}$ and $R_{18}$ respectively are omitted.

As will be appreciated by the skilled person, the three substituents associated with each of $R_1$, $R_2$, $R_3$ and $R_4$ (for instance; $R_4'$, $R_4''$ and $R_4'''$ with respect to $R_4$) need not be identical.

Typically, $R_a$ is selected from: hydrogen, alkyl, alkenyl, aryl, halogen, hydroxy, alkoxy, carboxylic acid, amino, amido, nitro or a combination thereof. Often, $R_a$ is selected from: hydrogen, alkyl, aryl, halogen, hydroxy or alkoxy; more typically, hydrogen, alkyl, or alkoxy; more typically still, hydrogen or alkyl; and most typically $R_a$ is hydrogen.

The inventors have found that compounds of formula (I) and formula (Ia) using bidentate ligands ($A_1$ to $A_4$) demonstrate a surprising efficacy against a variety of microbes. In particular, whilst there is no particular restriction on the choice of bidentate ligand, it has been found that compounds according to formula (III) are particularly effective. Such bidentate ligands are shown below:

formula (III)

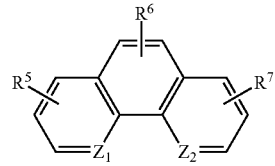

wherein,
$Z_1$ and $Z_2$ are each independently selected from: N, O, S; and $R_5$, $R_6$, and $R_7$ are each independently selected from: hydrogen, alkyl, alkenyl, aryl, halogen, haloalkyl, haloalkenyl, haloaryl, hydroxy, alkoxy, carboxylic acid, amino, amido, nitro or combination thereof.

Without being bound by theory, it is believed that the use of compounds of general structure formula (III), comprising two donor atoms at the 4 and 5 positions, results in compounds with a surprising antimicrobial efficacy. Whilst each donor atom, $Z_1$ and $Z_2$, may be different, it is often the case that $Z_1$ and $Z_2$ are the same. Moreover, each of $Z_1$ and $Z_2$ may be independently selected from N or O. Most typically, at least one of $Z_1$ and $Z_2$ is nitrogen and often each of $Z_1$ and $Z_2$ is nitrogen. As such, it is typically the case that $A_1$, $A_2$, $A_3$ and $A_4$ are each independently phenanthroline or derivatives thereof.

Each of substituents $R_5$, $R_6$ and $R_7$ represents those groups attached to the rings that make up the general structure of formula (III). $R_5$ and $R_7$ refer to up to three substituents and $R_6$ refers to up to two substituents as indicated in formula (IIIa):

formula (IIIa)

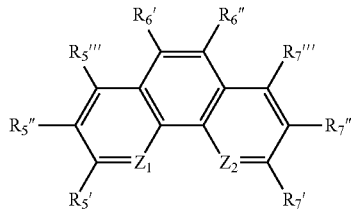

Each of $R_5$, $R_6$ and $R_7$ may be the same or different; and each substituent thereof may be the same of different. For instance, where $R_5$ is an alkyl group; one, two or three of $R_5'$, $R_5''$ and $R_5'''$ may be an alkyl group. It is often the case that $R_5$, $R_6$, and $R_7$ are each independently selected from: hydrogen, alkyl, alkoxy, aryl or combinations thereof. It is often the case that at least one of $R_5$, $R_6$, and $R_7$ is hydrogen; often, that at least two of $R_5$, $R_6$, and $R_7$ are hydrogen; and in some instances, each of $R_5$, $R_6$, and $R_7$ are hydrogen.

In an alternative embodiment, it is often the case that at least one of $R_5$, $R_6$, and $R_7$ is alkyl; often, that at least two of $R_5$, $R_6$, and $R_7$ are alkyl; and in some instances, each of $R_5$, $R_6$, and $R_7$ are alkyl. In some instances, two of $R_5$, $R_6$, and $R_7$ are alkyl. Typically, where two of $R_5$, $R_6$, and $R_7$ are alkyl, $R_5$ and $R_7$ are alkyl. Typical alkyl groups are as defined above. However, it is often the case that, where $R_5$, $R_6$, or $R_7$ is an alkyl group, said alkyl group is selected from: methyl, ethyl or propyl. Typically, said alkyl group is methyl or ethyl and more typically, said alkyl group is methyl.

In a further alternative embodiment, it is often the case that at least one of $R_5$, $R_6$, and $R_7$ is aryl; often, that at least two of $R_5$, $R_6$, and $R_7$ are aryl; and in some instances, each of $R_5$, $R_6$, and $R_7$ are aryl. In some instances, two of $R_5$, $R_6$, and $R_7$ are aryl. Typically, where two of $R_5$, $R_6$, and $R_7$ are aryl, $R_5$ and $R_7$ are aryl. Typical aryl groups are as defined above. However, it is often the case that, where $R_5$, $R_6$, or $R_7$ is an aryl group, said aryl group is selected from: phenyl, pyridyl or furyl. Typically, said aryl group is phenyl or pyridyl and more typically, said aryl group is phenyl.

It may be the case that $R_5$ and $R_7$ are the same. Further, it is often the case that the bidentate ligand is symmetrical, i.e. the substitution pattern about the structure of formula (IIIa) is symmetrical, e.g. wherein $R_5'$ and $R_7'$ are methyl groups and all other substituents are hydrogen.

Typical bidentate ligands are compounds (1) to (7) shown below:

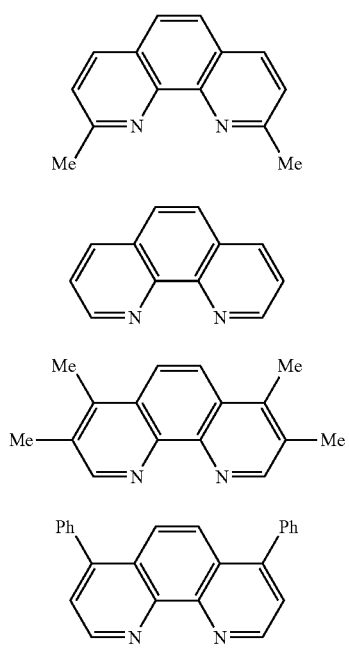

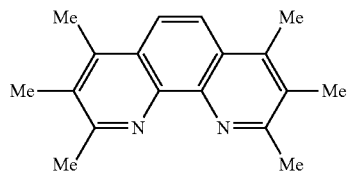

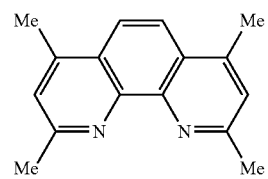

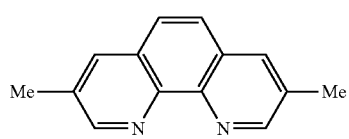

It is often the case that at least two of $A_1$, $A_2$, $A_3$ and $A_4$ are the same. Often, at least three of $A_1$, $A_2$, $A_3$ and $A_4$ are the same; and it may be the case that all four of $A_1$, $A_2$, $A_3$ and $A_4$ are the same. In some embodiments, each of $A_1$, $A_2$, $A_3$ and $A_4$ are different. Each of $A_1$, $A_2$, $A_3$ and $A_4$ may independently be selected from compounds (1) to (7). Often, $A_1$, $A_2$, $A_3$ and $A_4$ are each independently selected from compounds (1), (2), (3), (5), (6) and (7); more typically $A_1$, $A_2$, $A_3$ and $A_4$ are each independently selected from compounds (1), (2) and (3); more typically still $A_1$, $A_2$, $A_3$ and $A_4$ are each independently selected from compounds (2) and (3); most typically $A_1$, $A_2$, $A_3$ and $A_4$ are each independently selected from compounds (1) and (2). It may be the case $A_1$, $A_2$, $A_3$ and $A_4$ are all represented by compound (3).

In the case of compounds of formula (IIa), each of $A_1$ and $A_2$ may independently be selected from compounds (1) to (7). Often, $A_1$ and $A_2$ are each independently selected from compounds (1), (2), (3), (5), (6) and (7); more typically $A_1$ and $A_2$ are each independently selected from compounds (1), (2) and (3); more typically still $A_1$ and $A_2$ are each independently selected from compounds (2) and (3); most typically $A_1$ and $A_2$ are each independently selected from compounds (1) and (2). It may be the case $A_1$ and $A_2$ are both represented by compound (3).

It is typically the case that compounds of the first aspect of the invention possess a positive charge, usually a 4+ charge for compounds of formula (I) and a 2+ charge for compounds of formula (Ia). Various counter ions may be provided to balance this charge. Whilst there is no particular restrictions on the choice of counter ion, this may typically be selected from: chloride, fluoride, bromide, hydroxide, nitrate, hexafluorophosphate, or combination thereof. Typically the counter ion is chloride or nitrate, usually chloride. For the avoidance of doubt, reference to compounds herein is also intended to encompass references to pharmaceutically acceptable salts thereof.

There is also provided, in a second aspect of the invention, a composition comprising the compound according to the first aspect of the invention. There is no particular restriction on the content of the composition. The composition may include one or more excipients to modify the physical or chemical properties of the composition as would be familiar to a person skilled in the art. The composition may be formulated as a tablet for oral delivery, as a topical formulation applicable to the body, or as a composition adapted for intravenous or subdermal delivery as would be familiar to a person skilled in the art.

The composition may include one or more additional active pharmaceutical ingredients including one or more additional antimicrobials, typically one or more additional antibiotics. The composition may also be prepared with a range of dosages of the compound of the first aspect of the invention.

The compound according to the first aspect of the invention and the composition according to the second aspect of the invention may be for the treatment of one or more diseases or disorders caused by microbes. More typically, the compound according to the first aspect of the invention and the composition according to the second aspect of the invention are used for the treatment of one or more diseases or disorders caused by bacteria, in particular gram-negative bacteria. Typical diseases include, but are not limited to: pneumonia, tuberculosis, cholera, syphilis, typhoid, tetanus, nosocomial infections (hospital acquired), urinary tract infections, blood stream infections or combinations thereof.

There is also provided in a third aspect of the invention a method of treating a microbial disease or disorder, comprising the steps of administering the compound of the first aspect of the invention or the composition of the second aspect of the invention to a patient. Typically, the microbial disease or disorder is a bacterial disease or disorder, usually caused by gram-negative bacteria. Typical examples include, but are not limited to: pneumonia, tuberculosis, cholera, syphilis, typhoid, tetanus, nosocomial infections (hospital acquired), urinary tract infections, blood stream infections, or combinations thereof.

There is provided in a fourth aspect of the invention a compound according to formula (IV) or (IVa):

formula (IV)

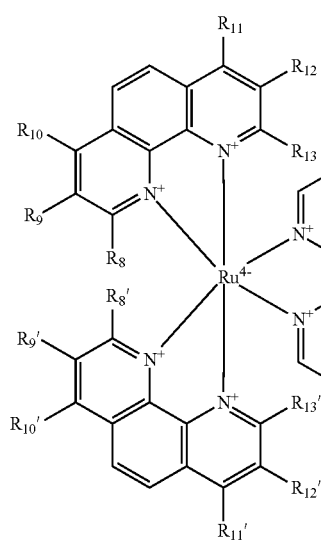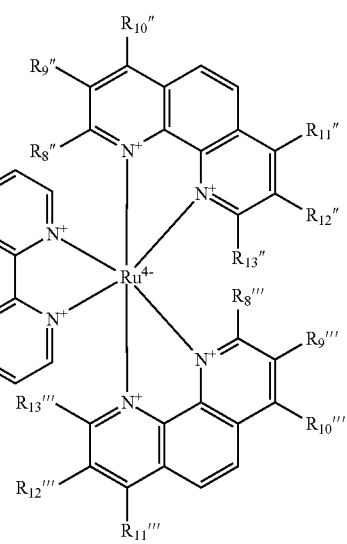

formula (IVa)

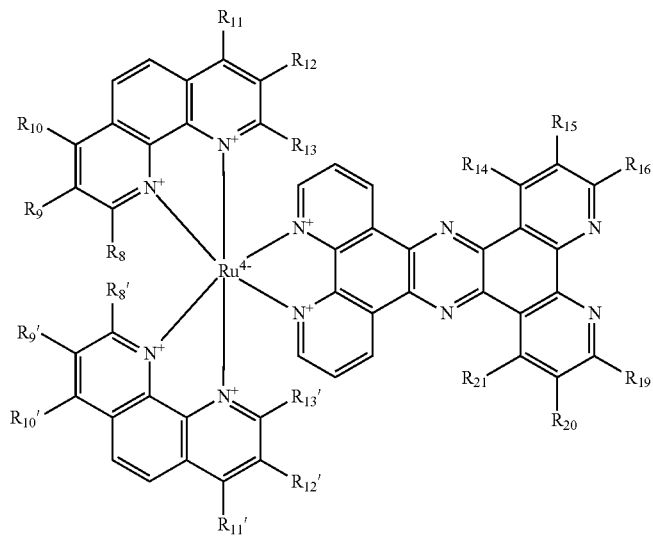

wherein
$R_8$, $R_8'$, $R_8''$, $R_8'''$, $R_9$, $R_9'$, $R_9''$, $R_9'''$, $R_{10}$, $R_{10}'$, $R_{10}''$, $R_{10}'''$, $R_{11}$, $R_{11}'$, $R_{11}''$, $R_{11}'''$, $R_{12}$, $R_{12}'$, $R_{12}''$, $R_{12}'''$, $R_{13}$, $R_{13}'$, $R_{13}''$ and $R_{13}'''$ are each independently selected from: hydrogen, alkyl, alkoxy, alkenyl and aryl;
with the proviso that at least one of $R_8$, $R_8'$, $R_8''$, $R_8'''$, $R_9$, $R_9'$, $R_9''$, $R_9'''$, $R_{10}$, $R_{10}'$, $R_{10}''$, $R_{10}'''$, $R_{11}$, $R_{11}'$, $R_{11}''$, $R_{11}'''$, $R_{12}$, $R_{12}'$, $R_{12}''$, $R_{12}'''$, $R_{13}$, $R_{13}'$, $R_{13}''$ and $R_{13}'''$ is selected from: alkyl, alkoxy, alkenyl and aryl (wherein each of alkyl, alkoxy, alkenyl and aryl groups are as described above); and wherein $R_{14}$ to $R_{16}$ and $R_{18}$ to $R_{21}$ are as described above.

It is often the case that two, three or all four of $R_8$, $R_8'$, $R_8''$ and $R_8'''$ are the same. It is also often the case that two, three or all four of $R_9$, $R_9'$, $R_9''$ and $R_9'''$ are the same. In some embodiments, two, three or all four of $R_{10}$, $R_{10}'$, $R_{10}''$ and $R_{10}'''$ may be the same and typically two, three or all four of $R_{11}$, $R_{11}'$, $R_{11}''$ and $R_{11}'''$ are also the same. Moreover, two, three or all four of $R_{12}$, $R_{12}'$, $R_{12}''$ and $R_{12}'''$ are typically the same and it is often the case that two, three or all four of $R_{13}$, $R_{13}'$, $R_{13}''$ and $R_{13}'''$ are the same. As will be appreciated, it is often easier to manufacture complexes using the same bidentate ligands, and ideally all four identical bidentate ligands, rather than using a combination of different bidentate ligands, as it can be difficult to accurately control the substitution pattern about the ruthenium metal centre in a reliable manner. Often separation techniques are required to achieve consistent "mixed" ligand complexes.

Similarly, in relation to formula (IVa), it is often the case that $R_8$ and $R_8'$ are the same. Moreover, it is often the case that $R_9$ and $R_9'$ are the same. In some embodiments, $R_{10}$ and $R_{10}'$ may be the same and typically $R_{11}$ and $R_{11}'$ are also the same. Moreover, $R_{12}$ and $R_{12}'$ are typically the same and it is often the case that $R_{13}$ and $R_{13}'$ are the same.

In one embodiment of the invention, at least one of $R_8$ to $R_{13}$ is alkyl; more typically, at least two of $R_8$ to $R_{13}$ are alkyl; even more typically, at least three of $R_8$ to $R_{13}$ are alkyl; more typically still, at least four of $R_8$ to $R_{13}$ are alkyl; even more typically still, at least five of $R_8$ to $R_{13}$ are alkyl; and most typically each of $R_8$ to $R_{13}$ are alkyl. Said alkyl group is typically selected from methyl, ethyl and propyl, most typically it will be methyl or ethyl, usually methyl. Those substituents $R_8$ to $R_{13}$ that are not alkyl, will typically be hydrogen. It is often the case that the substitution pattern about the bidentate ligands is symmetrical (e.g. wherein $R_8$, $R_9$ and $R_{10}$ are identical to $R_{13}$, $R_{12}$ and $R_{11}$ respectively). Often, two of $R_8$ to $R_{13}$ are alkyl, more typically four of $R_8$ to $R_{13}$ are alkyl, and in some instances all six of $R_8$ to $R_{13}$ are alkyl.

Often, it will be the case that $R_8$ and $R_{13}$ are alkyl (usually methyl); and typically, in such situations, $R_9$ to $R_{12}$ will be hydrogen. Alternatively, it may be the case that $R_9$ to $R_{12}$ are alkyl (usually methyl); and typically, in such situations, $R_8$ and $R_{13}$ are hydrogen. Further, it may be the case that $R_9$ and $R_{12}$ are alkyl (usually methyl); and typically, in such situations, $R_8$, $R_{10}$, $R_{11}$ and $R_{13}$ are hydrogen. Alternatively, it may be the case that $R_{10}$ and $R_{11}$ are alkyl (usually methyl); and typically, in such situations, $R_8$, $R_9$, $R_{12}$ and $R_{13}$ are hydrogen.

In another embodiment of the invention, at least one of $R_8$ to $R_{13}$ is aryl; and more typically, at least two of $R_8$ to $R_{13}$ are aryl. Said aryl group is typically selected from phenyl, pyridyl and furyl; most typically phenyl. Those substituents $R_8$ to $R_{13}$ that are not aryl, will typically be hydrogen. It is often the case that the substitution pattern about the bidentate ligands is symmetrical (e.g. wherein $R_8$, $R_9$ and $R_{10}$ are identical to $R_{13}$, $R_{12}$ and $R_{11}$ respectively). Often, two of $R_8$ to $R_{13}$ are aryl, and in some instances four of $R_8$ to $R_{13}$ are aryl.

Often, it will be the case that $R_{10}$ and $R_{11}$ are aryl (usually phenyl); and typically, in such situations, $R_8$, $R_9$, $R_{12}$ and $R_{13}$ are hydrogen. Alternatively, it may be the case that $R_9$ to $R_{12}$ are aryl (usually phenyl); and typically, in such situations, $R_8$, $R_{10}$, $R_{11}$ and $R_{13}$ are hydrogen.

It may be the case that the compound is represented by formula (V) or formula (Va):

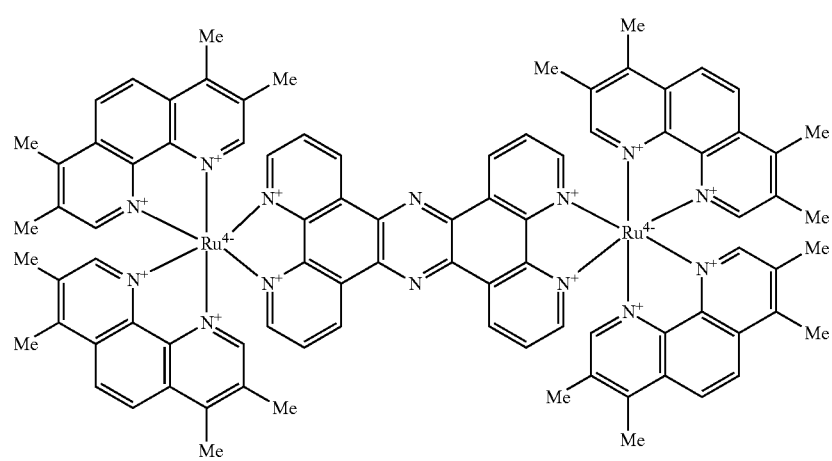

formula (V)

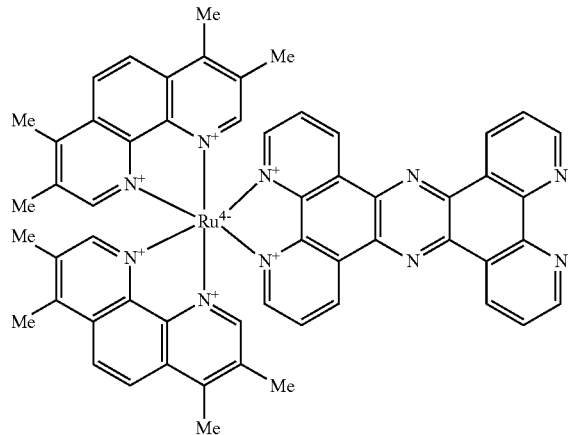

formula (Va)

or a pharmaceutically acceptable salt thereof. There is no particular restriction on the choice of counter ion that may be used and exemplary counter ions are described above.

There is also provided, in a fifth aspect of the invention, a composition comprising the compound according to the fourth aspect of the invention. There is no particular restriction on the content of the composition. The composition may include one or more excipients to modify the physical or chemical properties of the composition as would be familiar to a person skilled in the art. The composition may be formulated as a tablet for oral delivery, as a topical formulation applicable to the body, or as a composition adapted for intravenous or subdermal delivery as would be familiar to a person skilled in the art.

The composition may include one or more additional active pharmaceutical ingredients including one or more antimicrobials, typically one or more antibiotics. The composition may also be prepared with a range of dosages of the compound of the first aspect of the invention.

The compound according to the fourth aspect of the invention and the composition according to the fifth aspect of the invention may be for the treatment of one or more diseases or disorders caused by microbes. More typically, the compound according to the fourth aspect of the invention and the composition according to the fifth aspect of the invention may be used for the treatment of one or more diseases or disorders caused by bacteria, in particular gram-negative bacteria. Typical diseases include, but are not limited to: pneumonia, tuberculosis, cholera, syphilis, typhoid, tetanus, nosocomial infections (hospital acquired), urinary tract infections, blood stream infections, or combinations thereof.

There is also provided in a sixth aspect of the invention a method of treating a microbial disease or disorder, comprising the steps of administering the compound of the fourth aspect of the invention or the composition of the fifth aspect of the invention to a patient. Typically, the microbial disease or disorder is a bacterial disease or disorder, usually caused by gram-negative bacteria. Typical examples include, but are not limited to: pneumonia, tuberculosis, cholera, syphilis, typhoid, tetanus, nosocomial infections (hospital acquired), urinary tract infections, blood stream infections, or combinations thereof.

The invention will now be described with respect to the enclosed figures, purely in order to aid understanding.

Images were taken on a Nikon Confocal Microscope using the 488 nm laser and red emission filter. Images were processed using Image J.

Figure 18:
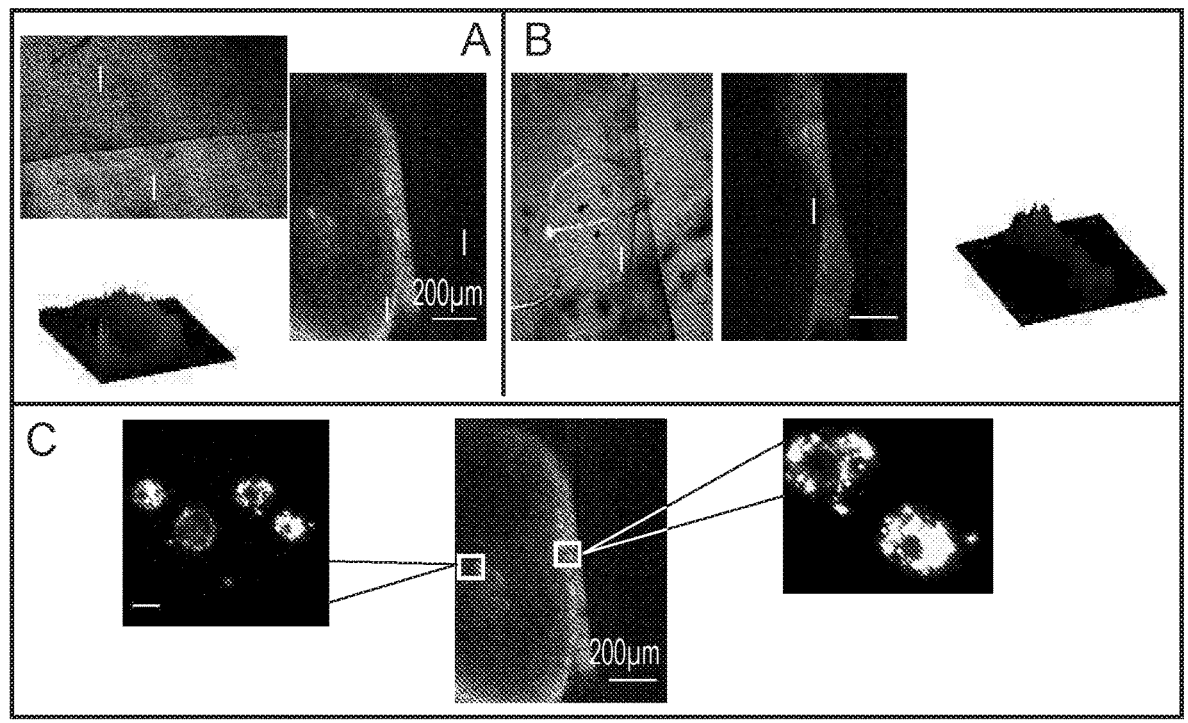
FIGS. 18 A-C are images through cleared *Galleria mellonella* larvae. The luminescence of complex $4^{4+}$ in stained *A. baumannii* AB184 was determined (head A, tail B). Hemocyte containing regions I and II of the bacterial cells are highlighted. *A. baumannii* were stained with 1.2 μM $4^{4+}$ for 30-minutes then fixed with PFA (4%). Larvae were injected with cells and incubated for 30-minutes, larvae anaethetised with diethyl ether were incubated in PFA (4%) for 30 minutes, prior to clearing with the CUBIC protocol.
Figure 19:
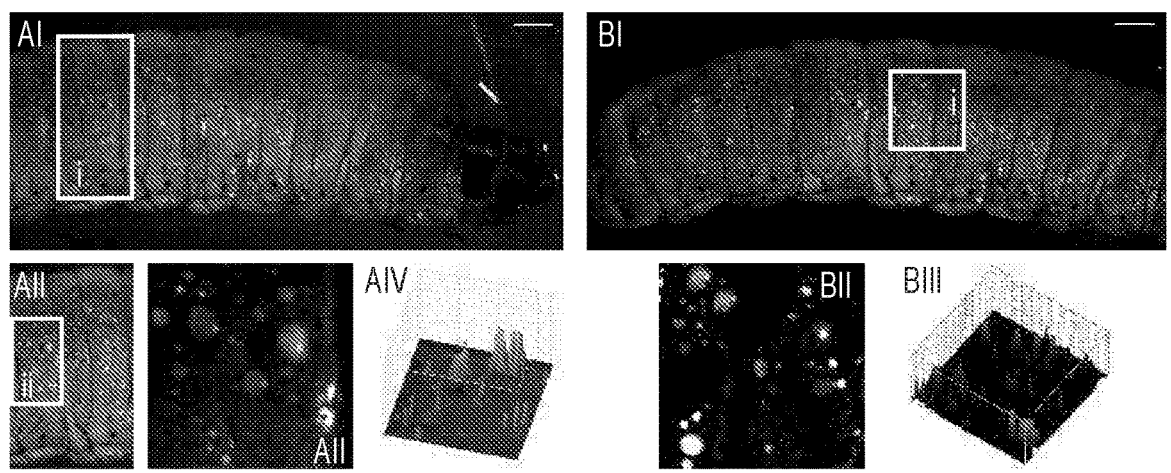

FIG. 19 provides a series of images of cleared *Galleria mellonella* larvae infected with *A. baumannii*, AB184, stained with NHS-ester 488-0.5 mg/mL (A) or complex $4^{4+}$-1.2 μM (B). Sections of the cells are identified (i) and expanded (AII, AIII, BII) to show *A. baumannii* within the hemocyte cells. 3D surface plots (AIV, BIII) are given to show peak emission intensity. Conditions are the same as FIG. 18 Images were taken on a Fluorescence Stereomicroscope: 490 nm ex/520 nm em (NHS-ester 488), 565 nm ex/640 nm. Images were processed using Image J.

Figure 20:
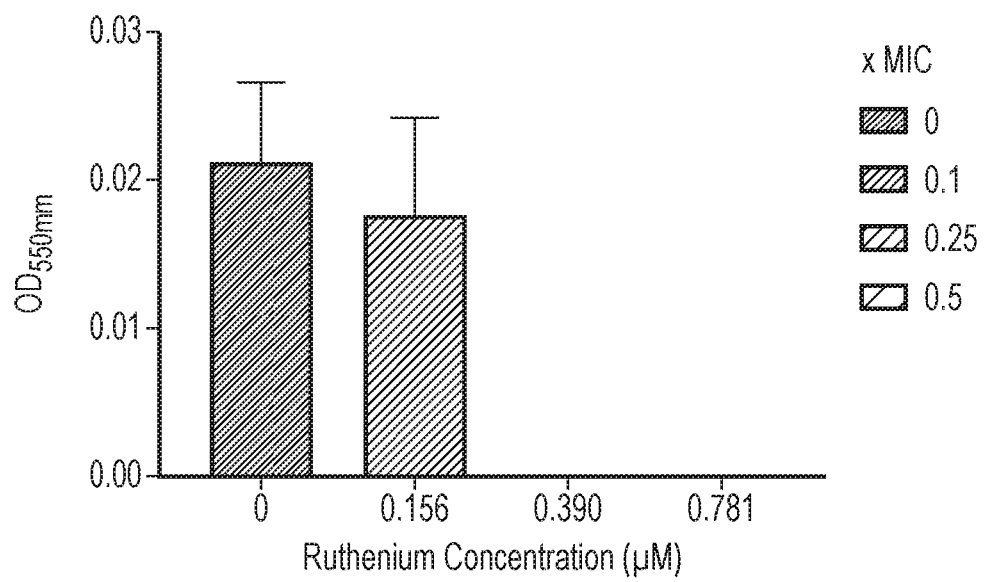
Figure 21:
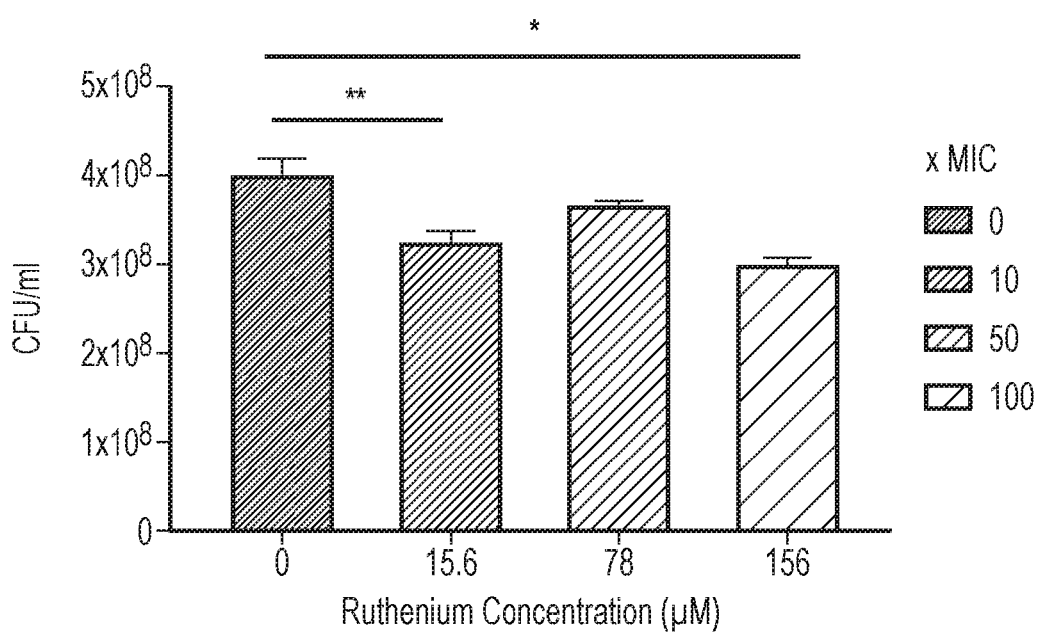

FIG. 20 shows biofilm formation of *E. coli* ST131, EC958, when subjected to different concentrations of $4^{4+}$. N≥3±SEM. Biofilm formed over 19 hours of incubation at 37° C. in 24-well plates. ST131 shows biofilm formation in no Ruthenium and 0.156 μM (10% of MIC), FIG. 21 shows biofilm CFU/mL produced by *E. coli* ST131 when existing biofilms were subjected to 15.6 μM, 78 μM and 156 μM of $4^{4+}$. N≥3±SEM. four day biofilm grown on filter membrane at 37° C. with MHA changed daily. Compound pipetted directly onto biofilm on day four, incubated for 24 hours. CFU/ml calculated using Miles and Mirsa method. One-way ANOVA performed with Turkey's multiple comparison tests.

Figure 22A:
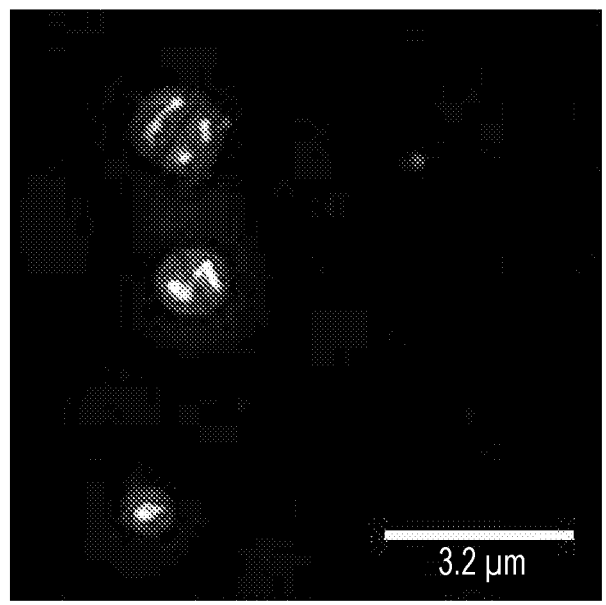
Figure 22B:
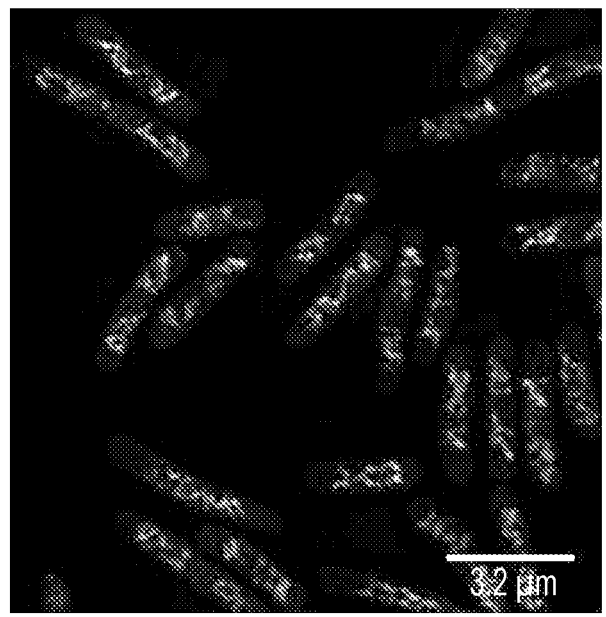

FIGS. 22A and 22B show $4^{2+}$ in EC958 showing helical DNA binding and mono-TMP in SH1000 again showing DNA binding.

Figure 23:
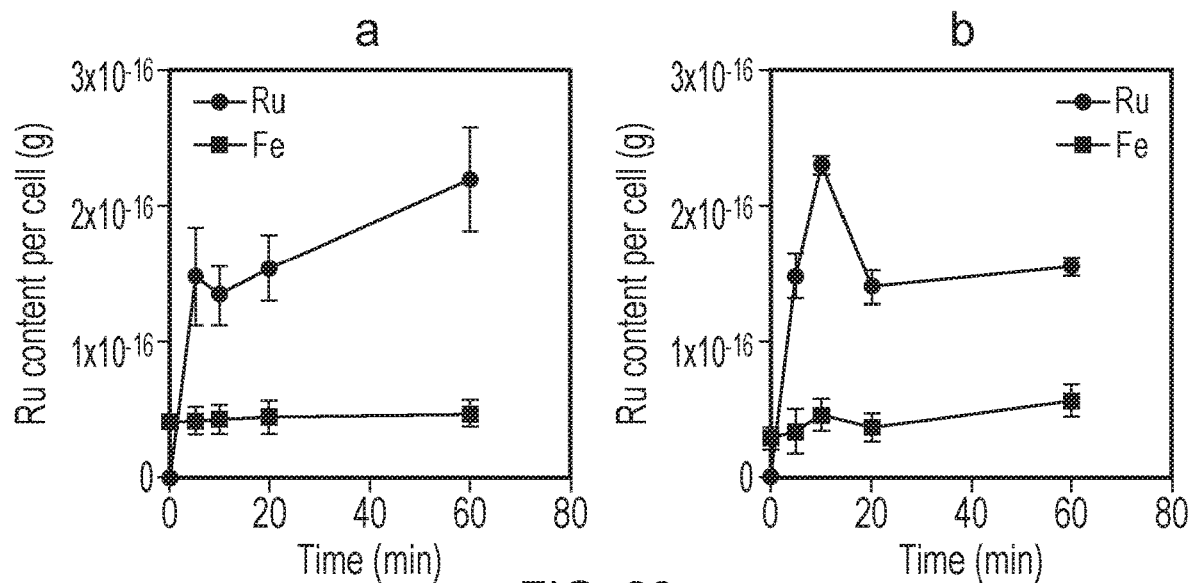

FIG. 23 shows the uptake of cell death effects of $4^{2+}$. ICP-AES data for the uptake of ruthenium by *E. coli* EC958 in the absence (a) and presence (b) of glucose after exposure to $4^{2+}$. Ru (top line) and Fe (bottom line) levels per cell are expressed as metal (g) per cell. Fe levels were calculated as a control. Conditions: concentration of $4^{2+}$=0.8 μM. Cells were washed with 0.5% (v/v) nitric acid to remove unbound complex. Error bars represent three independent biological repeats±SD.

Figure 24:
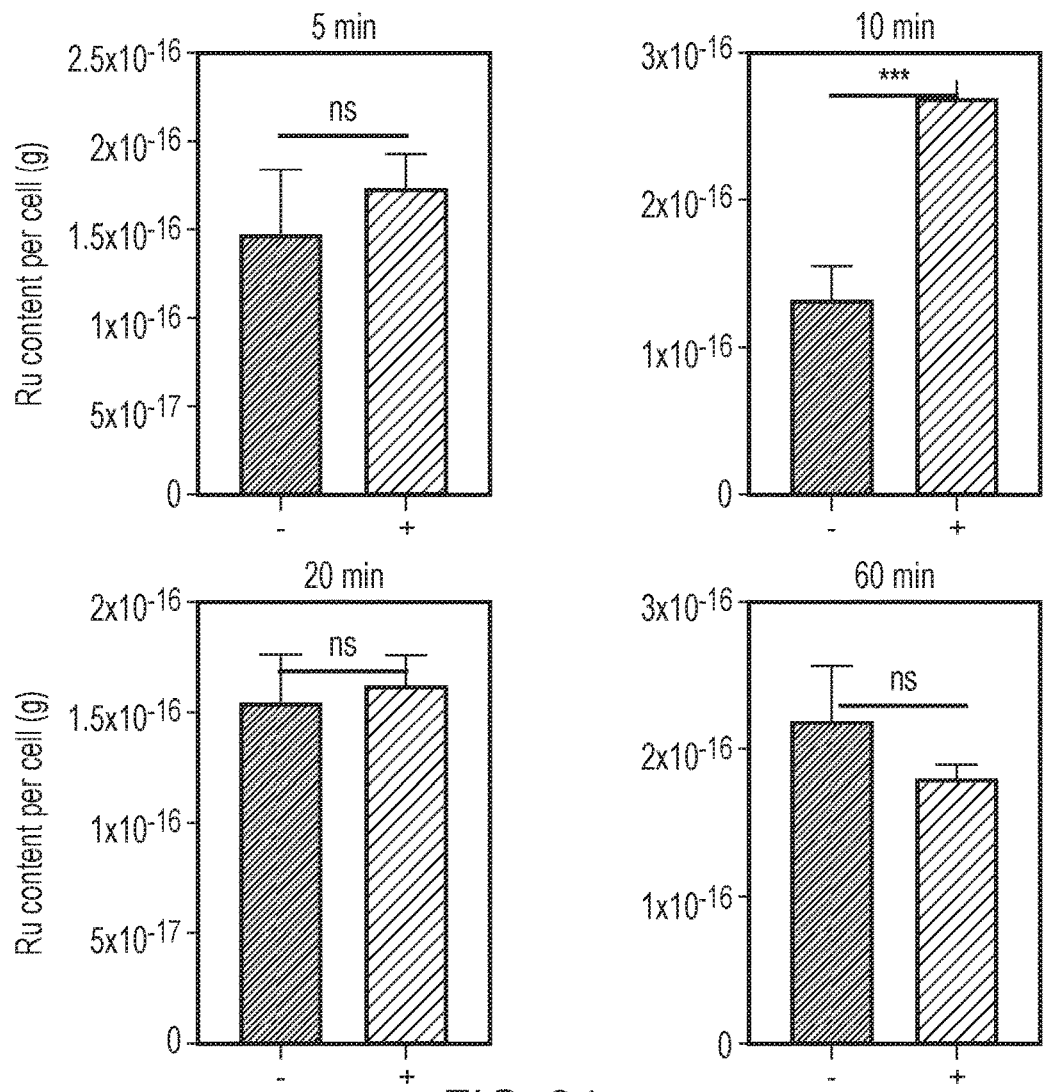

FIG. 24 shows the difference in Ru content per cell (g) at each time point (+) with glucose and (−) without glucose for $4^{2+}$. Showing significant differences in accumulation of ruthenium in the (+) with glucose sample at 10 minutes. Ruthenium content per cell determined via ICP-AES.

Figure 1:
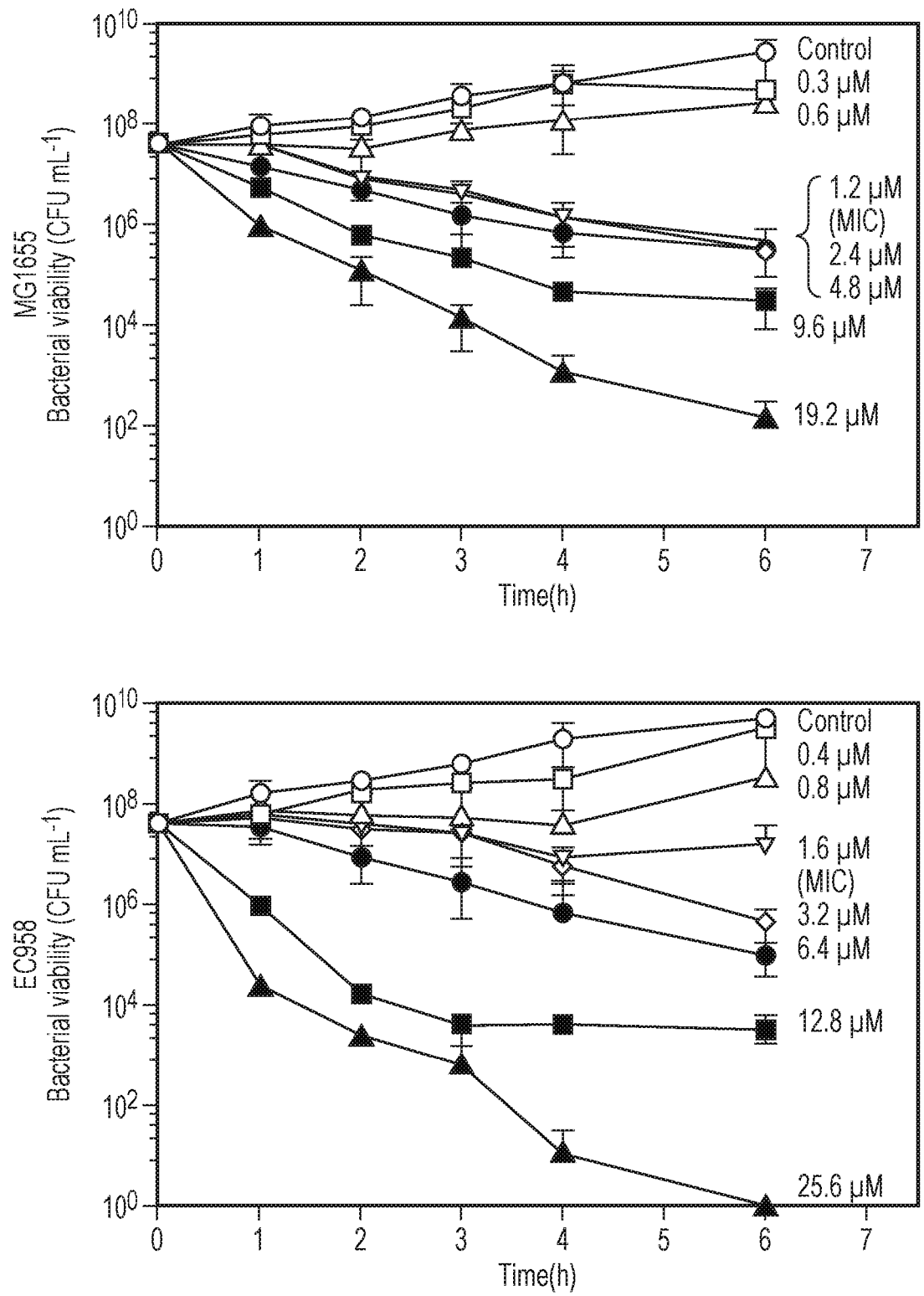
FIG. 1A shows the uptake and cell death effects of $4^{4+}$. Complex $4^{4+}$ induces dose-dependent killing of *E. coli* MG1655 (top) and EC958 (bottom) planktonic cultures in vitro. The complex was added at various concentrations below and exceeding the MIC, 1.2 µM (A) or 1.6 µM (B), of $4^{4+}$ in GDMM. Killing was determined by monitoring the number of colony forming units (CFU) per mL at time intervals up to 6 h post treatment. Error bars represent three independent biological repeats±standard deviation (SD).
FIG. 1B shows the uptake of cell death effects of $4^{4+}$. ICP-AES data for the uptake of ruthenium by *E. coli* EC958 in the absence (left) and presence (right) of glucose after exposure to $4^{4+}$. Ru (top line) and Fe (bottom line) levels per cell are expressed as metal (g) per cell. Fe levels were calculated as a control. Conditions: concentration of $4^{4+}$=0.8 µM. Cells were washed with 0.5% (v/v) nitric acid to remove unbound complex. Error bars represent three independent biological repeats±SD.
Figure 1:
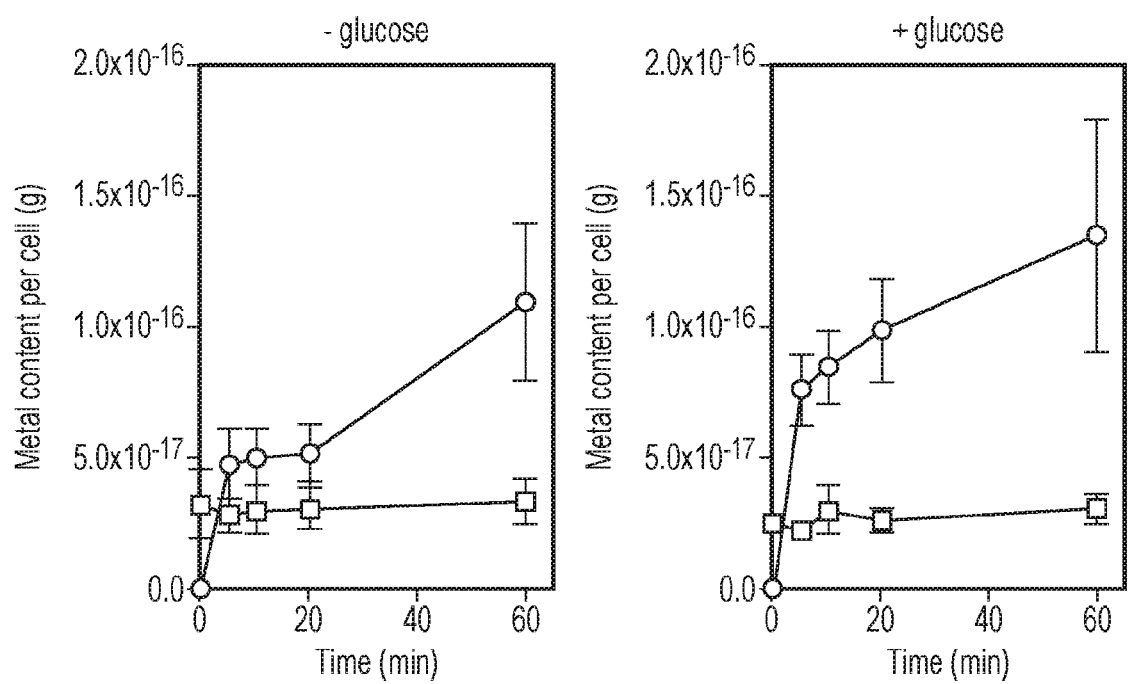
Figure 25:
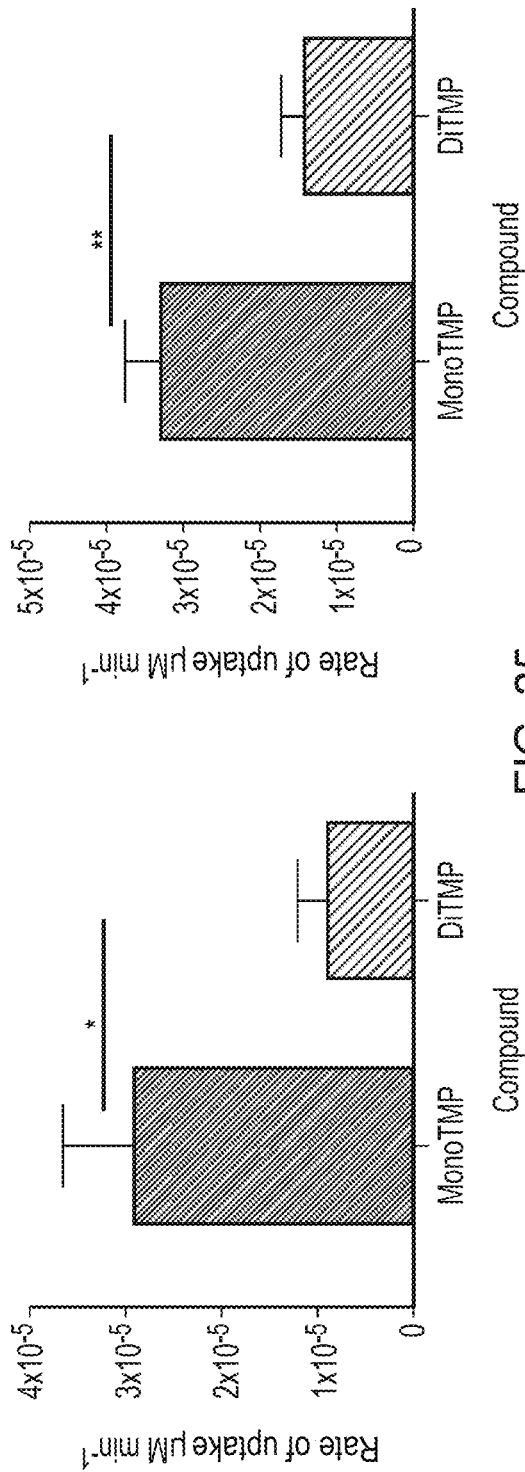

FIG. 25 shows the relative rates of uptake of Ru for $4^{2+}$ and $4^{4+}$ based on the results of FIGS. 1B and 23.

Figure 26:
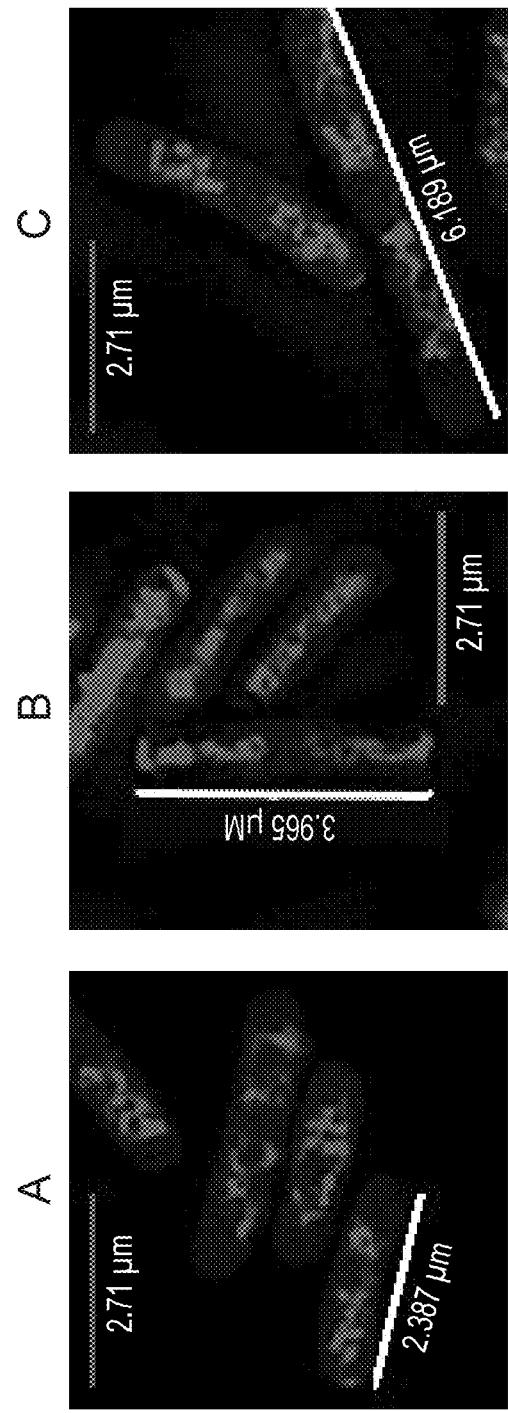

FIGS. 26 A-C show the localization of $4^{2+}$ in *E. coli* EC958 cells visualized through Laser Scanning Confocal Microscopy (LSCM) and Stimulated Emission Depletion (STED) nanoscopy at 60 minutes, 120 minutes and 24 hours. The cells were imaged using the emission of $4^{2+}$ on excitation at 470 nm with a White Light Laser and a 470 nm notch filter, deconvoluted diffraction-limited images (d-LSCM) and super resolution (d-STED) images were processed using commercial Huygens software (SVI). Conditions: after treatment with 0.8 μM $4^{2+}$, cells were washed with nitric acid before fixing with paraformaldehyde (16%).

Figure 27:
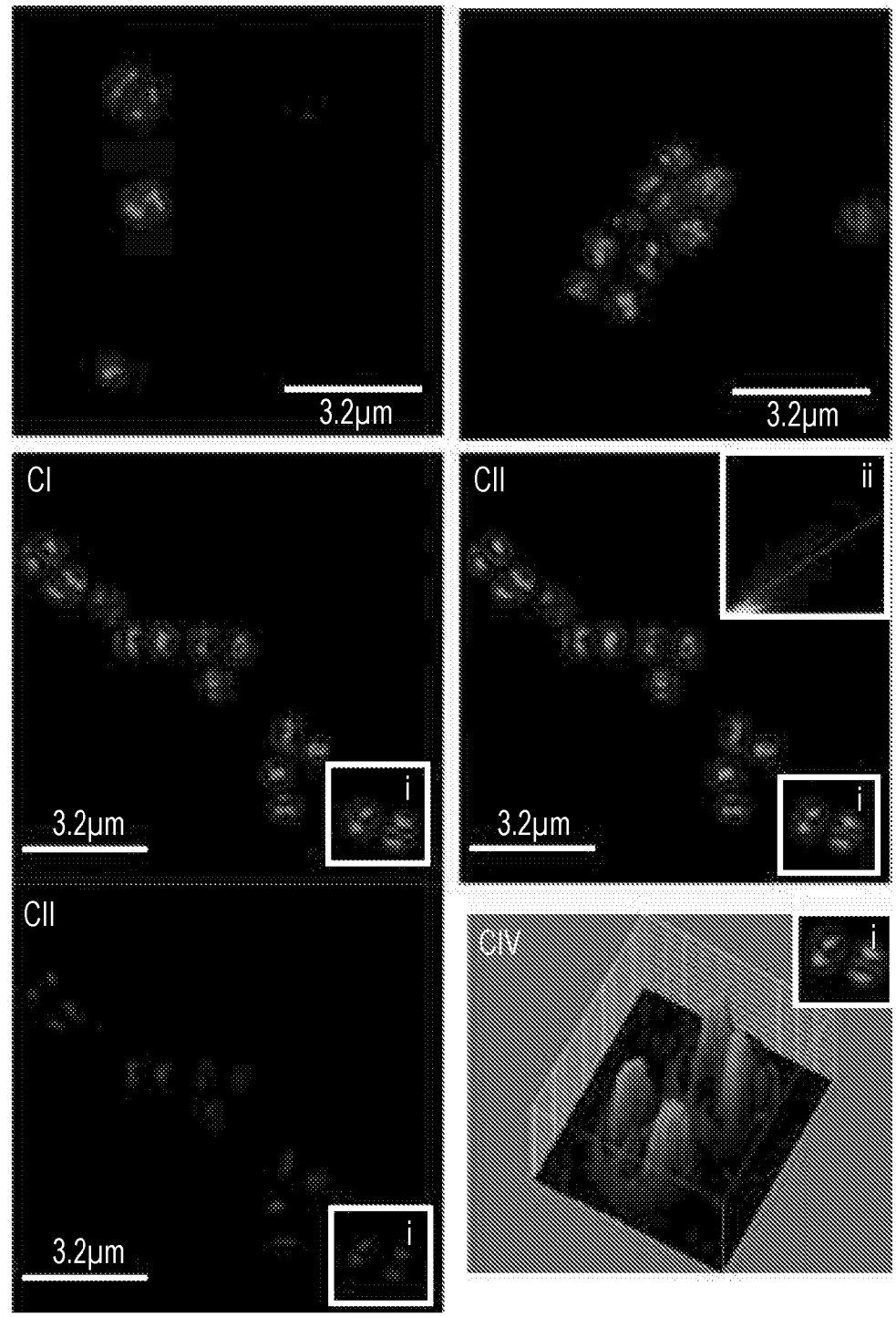

FIG. 27 shows the results of a DNA co-staining experiment. *S. aureus* stained with $4^{2+}$ (top and CI), *S. aureus* stained with the DNA stain DAPI (CII), overlay image (CIII), overlay 3D surface plot (CIV). The image shows a direct overlay of DAPI and Mono-TMP to calculate a Pearson's colocalisation constant of >0.9.

Figure 28:
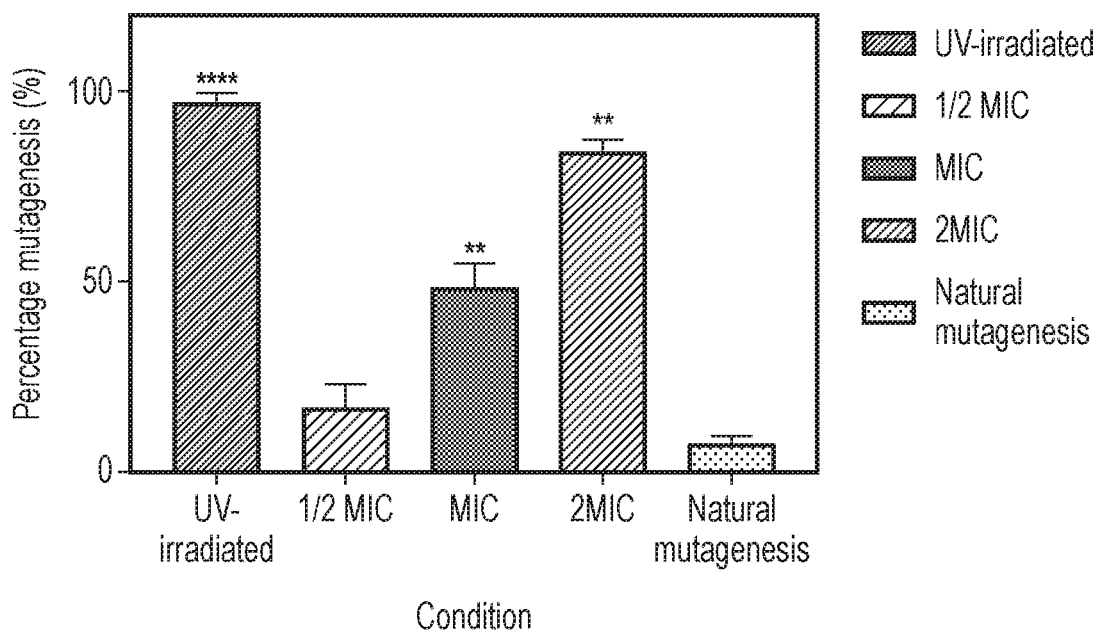

FIG. 28 shows the results of an Ames mutagenic assay for *E. coli* in the presence of $4^{2+}$. Percentage mutagenesis was measured by treating *E. coli* (25% overnight culture, 75% media) cells with $4^{2+}$ at 0 (natural mutagenesis control), 0.5, 1.0 and 2.0×. Bromocresol purple indicator was added, and the percentage colour change from purple to yellow measured after incubation for 48 hours. A positive control with cells irradiated with UV-light was added for comparison.

Figure 29:
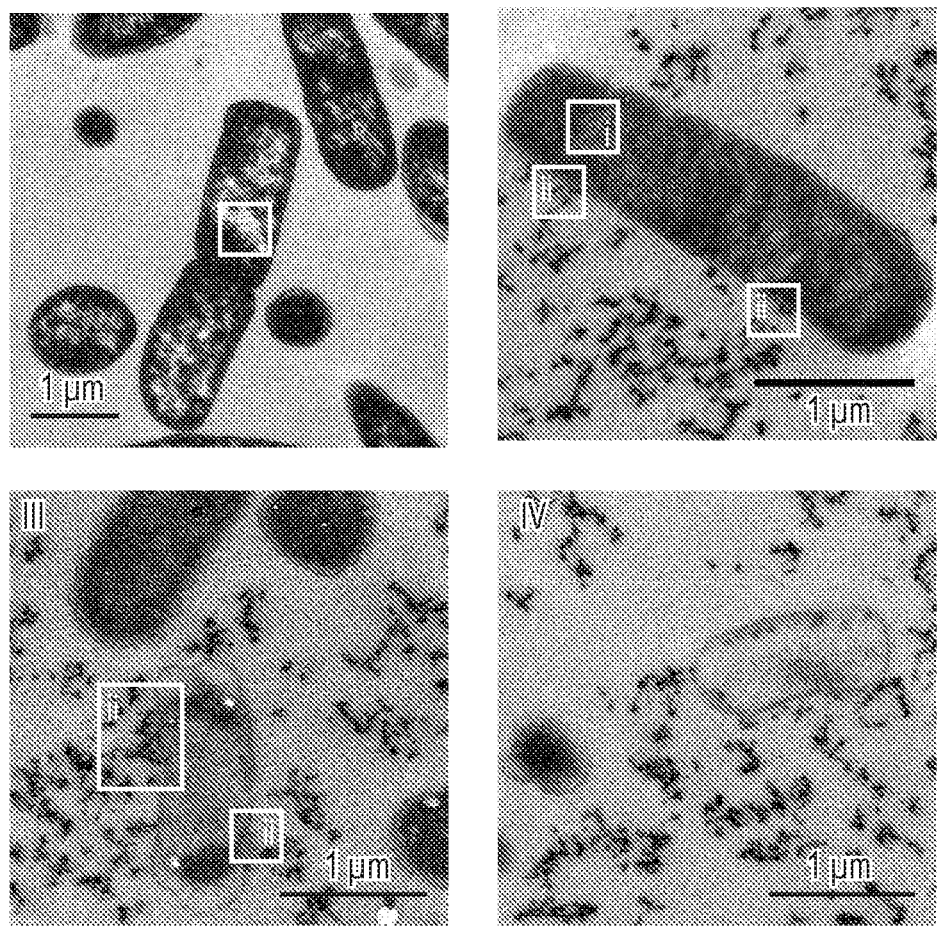

FIG. 29 shows TEM images of *E. coli* in the presence of $4^{2+}$.

Figure 30:
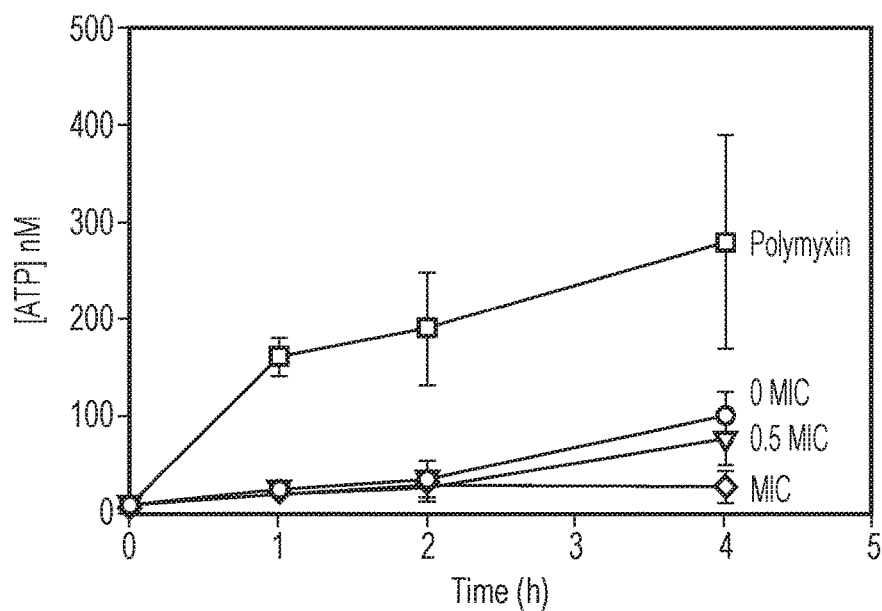

FIG. 30 shows $4^{2+}$ induced ATP release from *E. coli* EC958 cells, extracellular [ATP] (nM) quantified with polymyxin measured on a luminometer for samples exposed to 0 (control), 0.5 MIC and 1.0 MIC of $4^{2+}$ over a period of four hours. Error bars represent three biological repeats±SD. Polymyxin 4 μg/mL.

Figure 31:
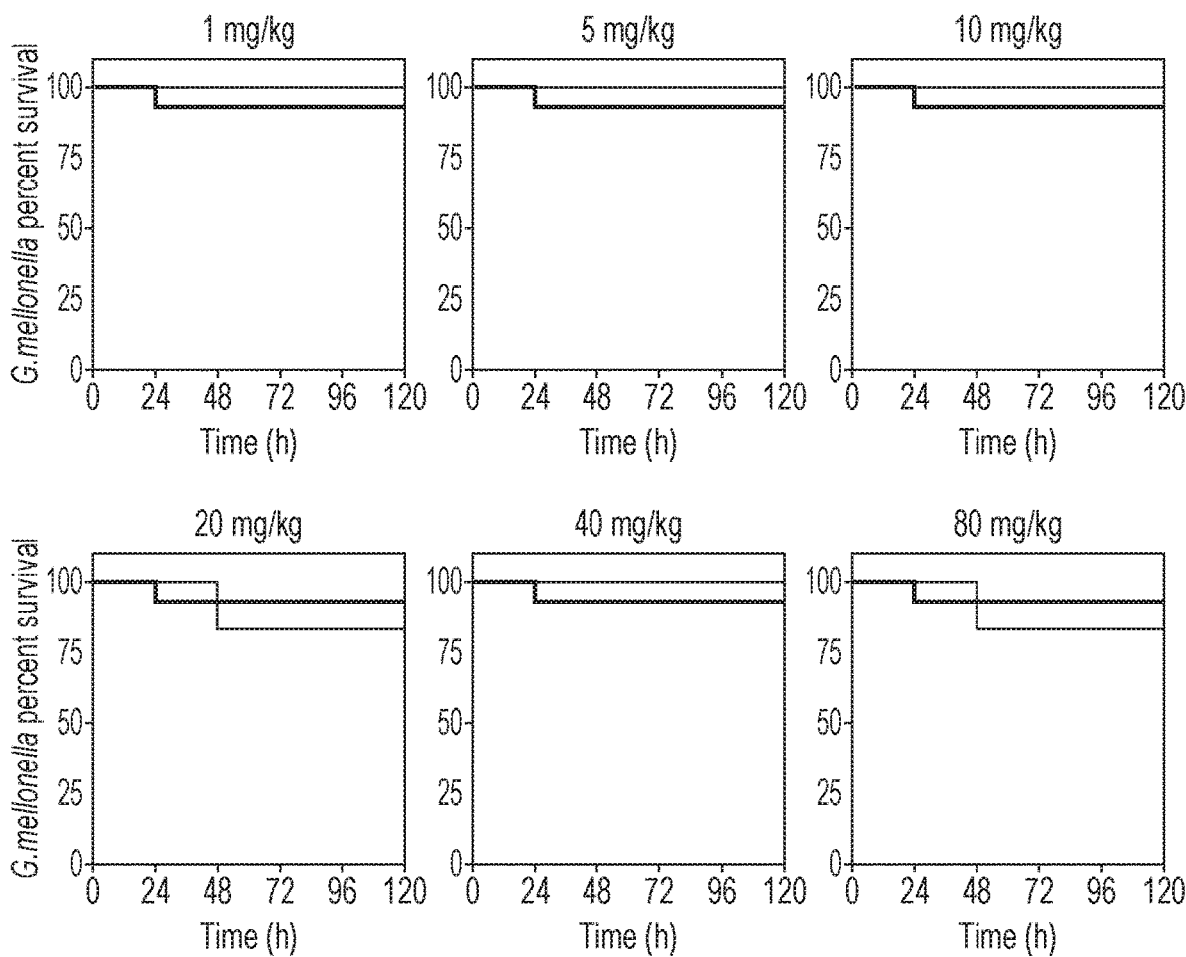

FIG. 31 shows a *Galleria mellonella* toxicity screen Kaplan-Meier survival curves, cells treated with 0-80 mg/kg of $4^{2+}$, incubated at 37.5° C. for 120 hours—water control (black), compound (red).

Figure 32:
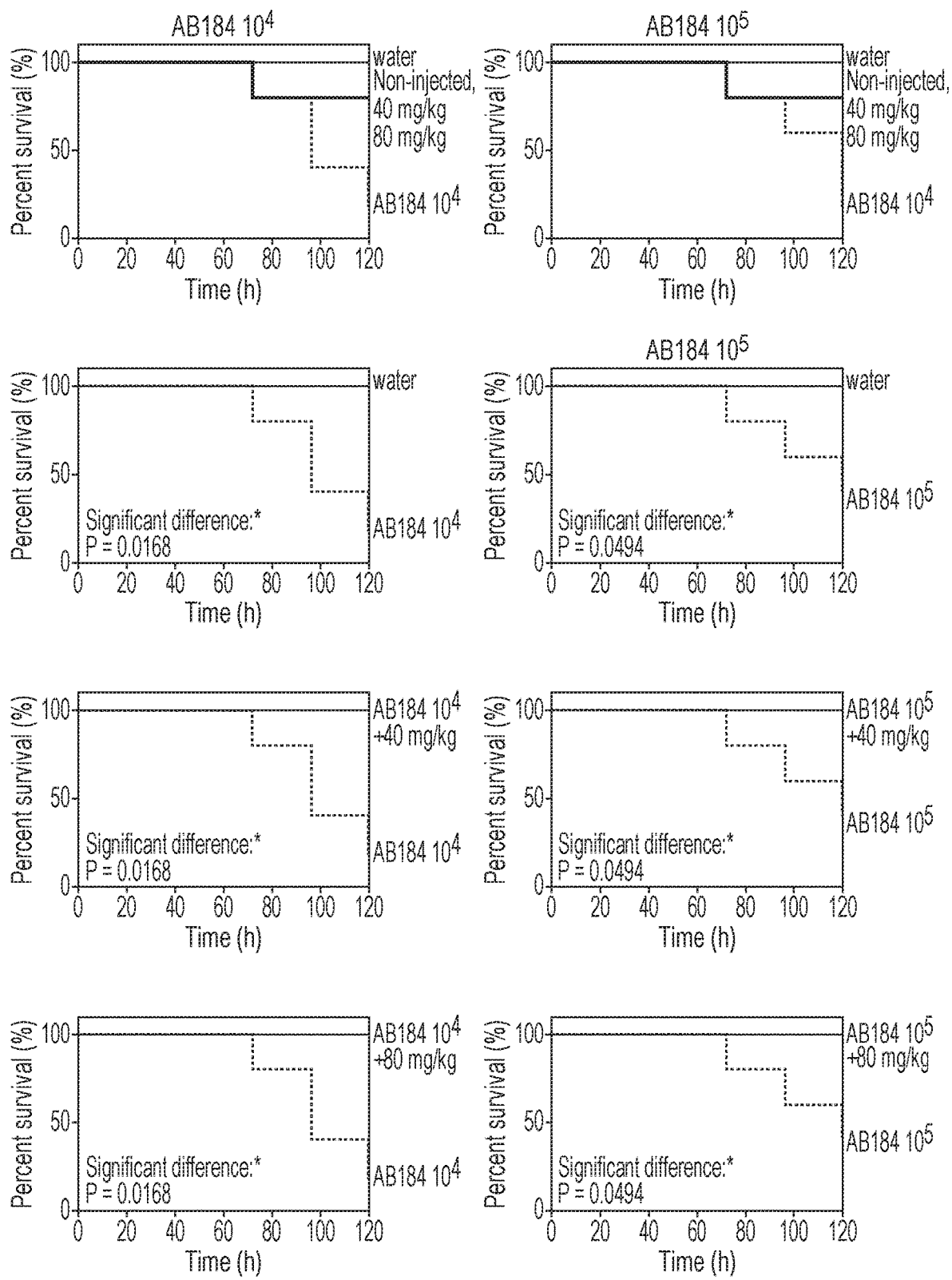

FIG. 32 shows *A. baumannii* AB184 toxicity screen Kaplan-Meier survival curves (initial bacterial count $10^4$—left and $10^5$—right), cells treated with 40 or 80 mg/kg of $4^{2+}$, incubated at 37.5° C. for 120 hours—water control (red), compound (green).

Figure 33:
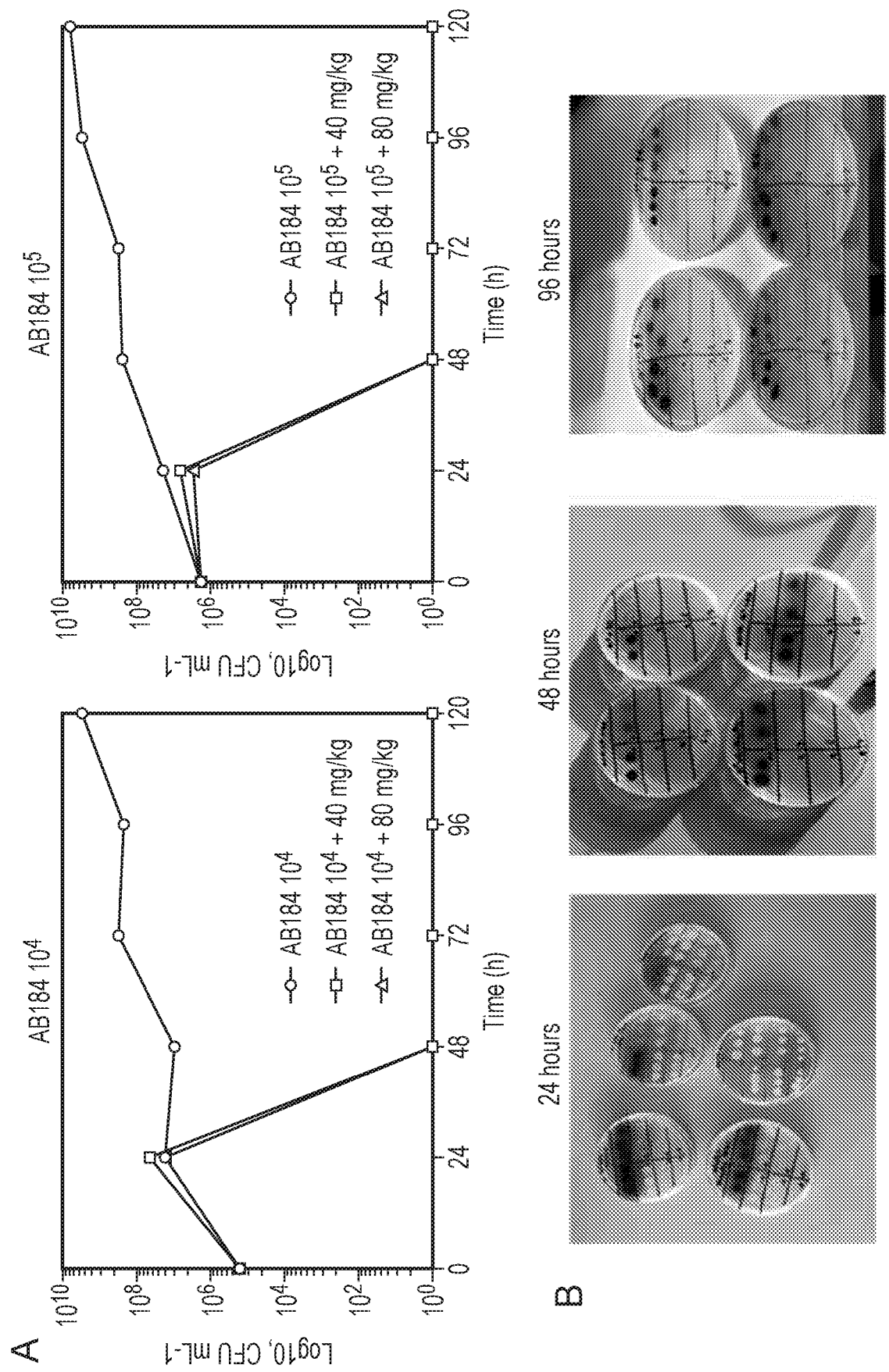

FIG. 33A shows the Bacteria CFU counts from extracted larvae hemolymph (*A. baumannii* AB184), observed for 120 hours in the presence of 40 mg/kg and 80 mg/kg $4^{2+}$. Initial bacterial count $10^4$ (left) and $10^5$ (right).

FIG. 33B shows photographs of the agar plates used to determine the plots of FIG. 33A with regard to the 80 mg/kg dosing of $4^{2+}$. The black marks are not bacteria colonies, but melanised hemolymph.

The invention will now be described with respect to specific examples. These examples are not to be construed as limiting and are provided to improve understanding of the invention.

EXAMPLES

Synthesis of Dinuclear Complexes

Complexes $1^{4+}$ and $2^{4+}$ (see scheme 1) were synthesized using the procedures outlined below.

Scheme 1. Compounds $1^{4+}$ to $4^{4+}$

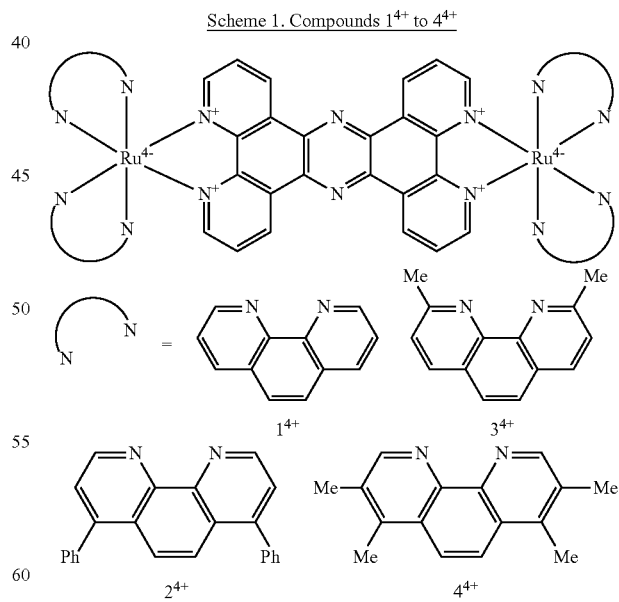

1,10-phenanthroline-5,6-dione (Compound $1^{4+}$)

1,10-phenanthroline (18.02 g, 100 mmol) was dissolved into 60% $H_2SO_4$ (125 mL). With constant stirring potassium bromate (66.81 g, 400.1 mmol) was added slowly to prevent the reaction becoming too vigorous. Reaction liberated brown fumes of bromine gas. Once all potassium bromate was added the reaction mixture was left to cool to room temperature. The mixture was further cooled by adding crushed ice (100 g) and placing in an ice bath. The solution was neutralised to pH 5-6 by dropwise addition of NaOH (20M), during neutralisation the mixture becomes hot this must be conducted in an ice bath to keep it cool. The yellow precipitate was filtered on a sinter and washed with water (1 L) and diethyl ether (100 mL). The product was dried in vacuo. The crude product was purified via recrystallisation in water/methanol (1:50) the bright yellow crystals were collected via vacuum filtration. Mass=16.04 g (76.31 mmol, 76.3%) yellow solid. $^1$HNMR (CDCl$_3$) δ (splitting integration); 7.61 (dd, 2H), 8.52 (dd, 2H), 9.13 (dd, 2H). MS; m/z: 210.1 (100) [M+].

Tetrapyrido[3,2-a:2',3'-c:3'-c:3'',2''-h:2''',3'''-j] phenazine (TPPHZ)

Ammonium acetate (15 g, 194.6 mmol), dip (2.90 g, 13.8 mmol) and sodium dithionite (300 mg, 1.72 mmol) were boiled under reflux for 2 hours at 180° C. under nitrogen. The reaction mixture was stirred occasionally. Once the reaction was complete the mixture was left to cool to room temperature, then distilled water (20 mL) was added.

The yellow precipitate formed was collected, filtered under vacuum and washed with water, methanol and acetone (3×20 mL). The resulting crude product was triturated in refluxing ethanol (100 mL) to remove impurities, filtered whilst hot and dried in vacuo. Mass=(0.92 g, 2.39 mmol, 34.6%) yellow solid. The product was sparingly soluble in most solvents. $^1$HNMR (CDCl$_3$) δ (splitting integration) 7.94 (dd, 4H), 9.41 (dd, 4H), 9.83 (dd, 4H). $^1$HNMR (d-TFA) δ (splitting integration) 8.62 (dd, 4H), 9.56 (dd, 4H), 10.52 (dd, 4H). MS; m/z (42.6%): 385.1 (100) [M+].

Ru(N—N)$_2$Cl$_2$

Four compounds were synthesised by the following method, where N—N represents the substituted phenanthroline ancillary ligand. RuCl$_3$.3H$_2$O, N—N and LiCl were heated in DMF for 8 hours under reflux. The reaction mixture was cooled to room temperature and acetone added. This was stored at 4° C. for 16 hours. The dark purple precipitate was washed with water and ethanol and dried in vacuo.

Ru(1,10-phenanthroline)$_2$Cl$_2$

RuCl$_3$.3H$_2$O (1.56 g, 6 mmol), LiCl (1.55 g, 36.9 mmol), phen (2.5 g, 13.9 mmol), DMF (20 mL) and acetone (100 mL). Mass=2.41 g (4.59 mmol, 66.1% yield). ES-MS m/z (%): 497 (70) [M-Cl]$^+$, 525 (100) [M-Cl]$^+$+CO.

[{Ru(N—N)$_2$}$_2$(tpphz)][PF$_6$]$_4$

The four compounds were synthesized by the following general procedure. [Ru(N—N)$_2$Cl$_2$] and (tpphz) were added to a 1:1 solution of ethanol and water. The solution was heated at reflux for 12 hours under nitrogen. After completion the reaction mixture was cooled to room temperature and stored at 4° C. for 16 hours. The red solution was filtered and the ethanol removed by rotary evaporation. A saturating amount of NH$_4$PF$_6$ was added; this caused the formation of a dark red precipitate. The precipitate was collected by filtration, washed with water and recrystallized in acetonitrile by addition of diethyl ether. The product was dried in vacuo and purified on an alumina column, using the following solvent system: was 95% MeCN, 3% dH$_2$O and 2% KNO$_3$.

[{Ru(1,10-phenanthroline)$_2$}$_2$(tpphz)][PF$_6$]$_4$

Tpphz (0.263 g, 0.68 mmol), [Ru(phen)$_2$Cl$_2$] (1 g, 1.89 mmol) and ethanol/water (50 mL). Mass=1.1 g (0.58 mmol, 85.6% yield). $^1$H NMR (MeCN-d$^6$) δ (splitting integration): 7.71 (m, 8H), 7.94 (dd, 4H), 8.09 (d, 4H), 8.29 (dd, 8H), 8.33 (s, 8H), 8.69 (dd, 8H), 10.01 (dd, 4H). ES-MS; m/z (%): 799 (10) [M−2PF$_6$]$^{2+}$, 484 (15) [M−3PF$_6$]$^{3+}$, 321 (50) [M−4PF$_6$]$^{4+}$, Accurate mass analysis: C$_{72}$H$_{28}$N$_{14}$[$^{102}$Ru]$_2$$^{4+}$ Calculated 321.1110. Found 321.1112.

Figure 5A:
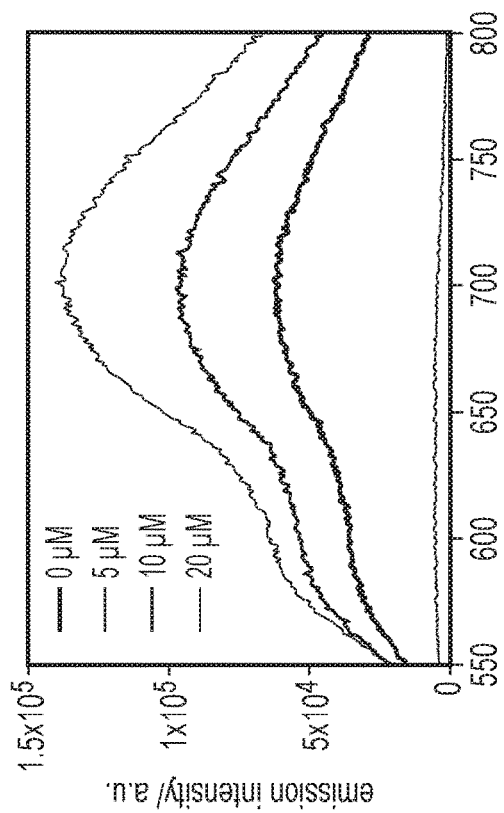
FIG. 5A shows UV-Vis absorption spectrum showing the change in molar extinction coefficient upon increasing concentration of [{Ru(3,4,7,8-tetramethyl-1,10-phenanthroline)2}2(tpphz)] in MeCN (conducted on a Cary 300 UV/Vis spectrophotometer at 27.5° C.).
Figure 5B:
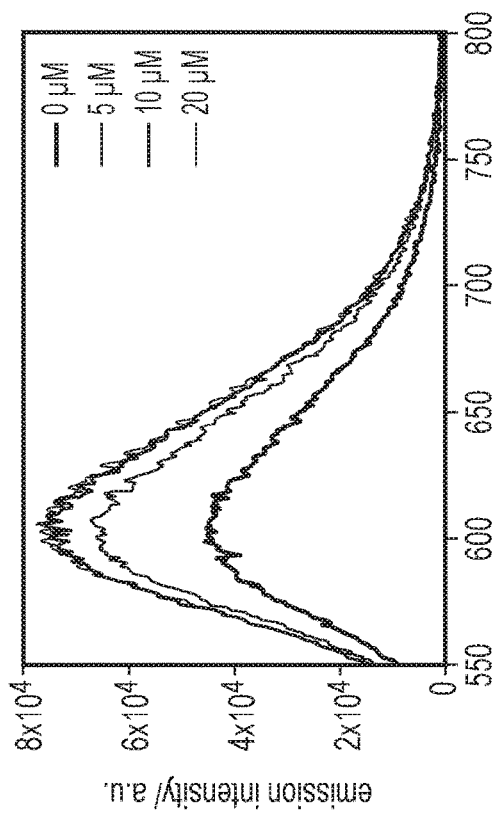
FIG. 5B shows UV-Vis absorption spectrum showing the change in molar extinction coefficient upon increasing concentration of [{Ru(3,4,7,8-tetramethyl-1,10-phenanthroline)2}2(tpphz)] in water (conducted on a Cary 300 UV/Vis spectrophotometer at 27.5° C.).
Figure 6A:
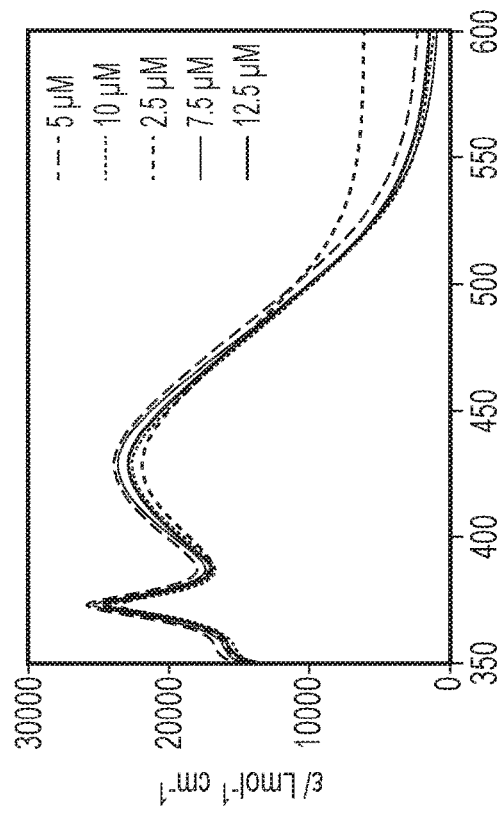
FIG. 6A shows emission spectra at increasing concentration of [{Ru(3,4,7,8-tetramethyl-1,10-phenanthroline)2}2(tpphz)] between 550-800 nm in MeCN. Conducted on a Fluoromax 3 fluorimeter at 27.5° C.
Figure 6B:
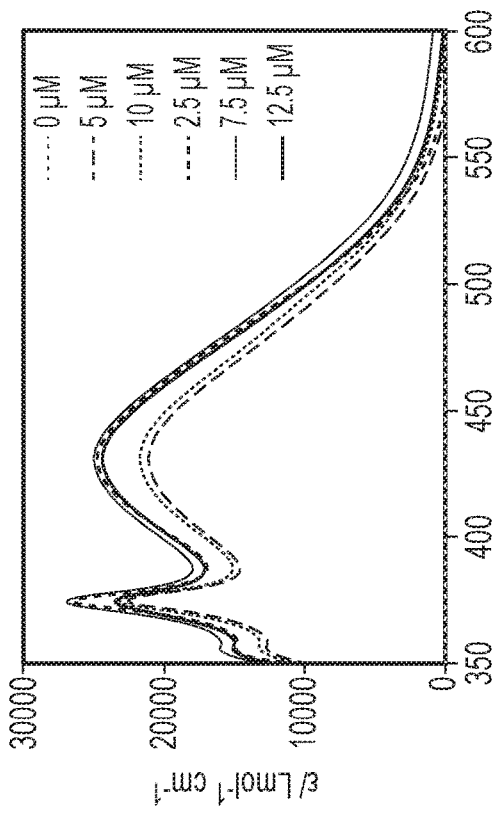
FIG. 6B shows emission spectra at increasing concentration of [{Ru(3,4,7,8-tetramethyl-1,10-phenanthroline)2}2(tpphz)] between 550-800 nm in water. Conducted on a Fluoromax 3 fluorimeter at 27.5° C.

Complexes 3$^{4+}$ and 4$^{4+}$ were synthesised using similar methods, employing the relevant methylated bidentate ligands. Both 3$^{4+}$ and 4$^{4+}$ display the expected intense Ru$^{II}$→tpphz based $^3$MLCT emission in MeCN centred at 670 nm and 700 nm respectively (FIGS. 5 and 6). The biological properties of each of these four complexes were studied using their chloride salts, which were obtained by anion metathesis.

Properties of Dinuclear Complexes

The balance of lipophilicity and hydrophilicity is believed to be important for live-cell uptake of bioactive substrates. The Log P for all four complexes were determined through octanol-water partition using the shake flask procedure. The results were as follows: 1$^{4+}$=1.77, 2$^{4+}$=1.03, 3$^{4+}$=1.38 and 4$^4$+=1.13. These data reveal that 2$^{4+}$ is the most lipophilic complex. Further, the relative lipophilicity appears to increase with the number of methyl groups attached to the ancillary ligands of these complexes.

Figure 7:
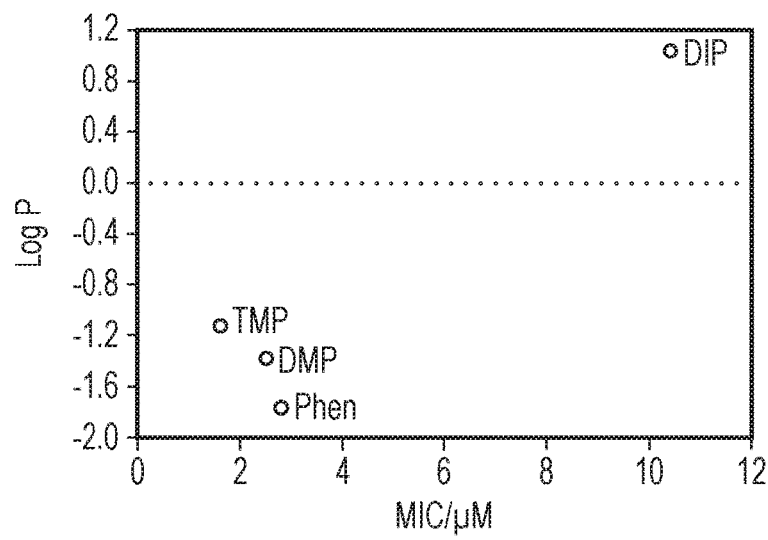
FIG. 7 shows a comparison of the Log P values determined and the activity (MIC) of each complex against the pathogenic *E. coli* strain EC958, to show the increase in activity with relative increase in lipophilicity. Log P data was collected using the shake flask procedure. "Phen" is phenanthroline, "DMP" is dimethyl phenanthroline, "TMP" is tetramethyl phenanthroline and "DIP" is diphenyl phenanthroline.

The bioactivity of these compounds was investigated with respect to the wild type K12-derivative MG1655 and uropathogenic multidrug resistant EC958 ST131 strains of *E. coli*. Another gram-positive bacteria, ESKAPE bacteria— the pathogenic gastrointestinal strain of *Enterococcus faecalis*, V583 (ATCC700802)—which is a major opportunistic pathogen (and a leading cause of urinary tract infections) was also tested with respect to the compounds. The minimum inhibitory concentration, MIC, of the four complexes was obtained in both glucose defined minimal media (GDMM) and nutrient rich Mueller-Hinton-II (MH-II) (FIG. 7). As demonstrated by the data in Table 1, all four complexes show higher activity in GDMM.

TABLE 1

MIC (μM) and MBC (μM) results for *E. coli* wild type (MG1655) and pathogenic (EC958) strains and *E. faecalis* pathogenic (V583) strain in GDMM and MH-II.

| Complex | MG1655 | EC958 | V583 | MG1655 | EC958 | V583 |
|---|---|---|---|---|---|---|
| | GDMM MIC Values | | | MH-II MIC Values | | |
| 1$^{4+}$ | 2.3 | 2.8 | 21.3 | 12.9 | 14.7 | 64 |
| 2$^{4+}$ | 7.8 | 10.4 | 64 | 139.9 | 145.1 | 64 |
| 3$^{4+}$ | 2.5 | 2.5 | 8 | 6.8 | 6.8 | 42.7 |
| 4$^{4+}$ | 1.2 | 1.6 | 0.5 | 5.6 | 5.6 | 3.3 |
| ampicillin | 3.3 | — | 1 | 5.7 | — | 0.5 |
| | GDMM MBC Values | | | MH-II MBC Values | | |
| 1$^{4+}$ | 11 | 4.3 | 53.3 | 11 | 4.6 | 53.3 |
| 2$^{4+}$ | 15.5 | 25.9 | 85.3 | 15.5 | 25.9 | 85.3 |
| 3$^{4+}$ | 20.3 | 5.1 | 53.3 | 20.3 | 5.1 | 53.3 |
| 4$^{4+}$ | 2.4 | 2.4 | 4 | 2.4 | 2.4 | 4 |
| ampicillin | 11.4 | — | 6.3 | 11.4 | — | 6.3 |

Although the most lipophilic compound, $2^{4+}$, shows the least activity—most likely due to its lower solubility in aqueous media—the lipophilic series shows an increase in lipophilicity and a concomitant increase in activity, with $4^{4+}$ having the highest activity against all three strains of bacteria. Notably, $1^{4+}$, $3^{4+}$ and $4^{4+}$ showed appreciable activity against β-lactam-resistant strain of *E. coli*, and the vancomycin resistant strain of *E. faecalis*; complex $4^{4+}$ even displays higher activity than ampicillin against the wild type strain of *E. coli*. Estimates of minimum bactericidal concentration, MBC, for $1^{4+}$-$4^{4+}$ were also obtained and summarized in Table 1. These data show that, as for the MIC data, an increase in MBC values between GDMM and MH-II is observed. Again, $4^{4+}$ is the most active, and in GDMM its MBC values were lower than ampicillin, indicating that, for all strains of bacteria, it is more active than the conventional antibiotic. Furthermore, as MBC values against all three strains exceed the MICs by at least 4-fold, all compounds function as bacteriostatic antimicrobial agents.

Figure 8:
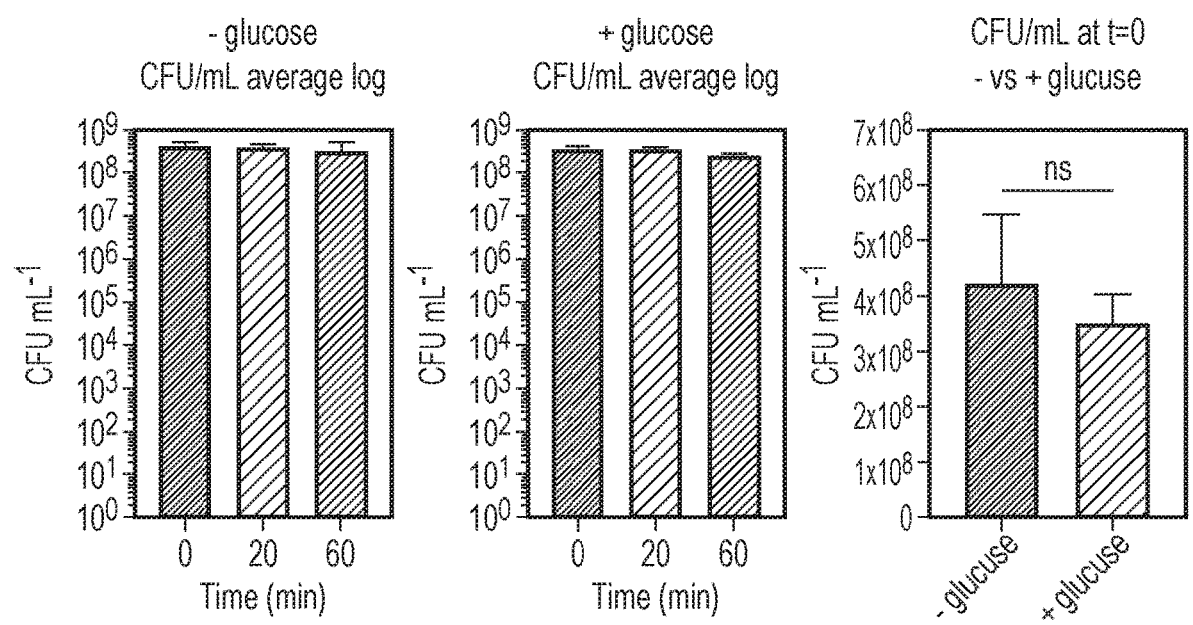
FIG. 8 shows CFU/mL counts for the accumulation experiment of $4^{4+}$ by EC958, to ensure that the number of bacteria in the solution maintained constant between each time point.

Having established that complex $4^{4+}$ had the most promising bactericidal properties, time-kill kinetics assays were carried out for both *E. coli* strains during 6 hours of exposure to increasing concentrations of the complex in minimal media at 37° C. (see FIGS. 1A and 8). At concentrations lower than the MIC there was a gradual increase in colony forming units (CFU), as the bacteria continued to grow. In both strains, it is evident that, at concentrations of MIC and above, the compound halts the bacterial proliferation and reduces the number of viable bacterial cells. For EC958 at the highest exposure to $4^{4+}$ no colonies formed, showing that all bacteria within the system were killed. Discrepancies between MBC values and the time-kill assays may have arisen from different experimental conditions—the MBC assay involves stationary incubation over 16-18 hours, and the time kill assay is carried out with 90% aeration and rotation over 6 hours.

Figure 9:
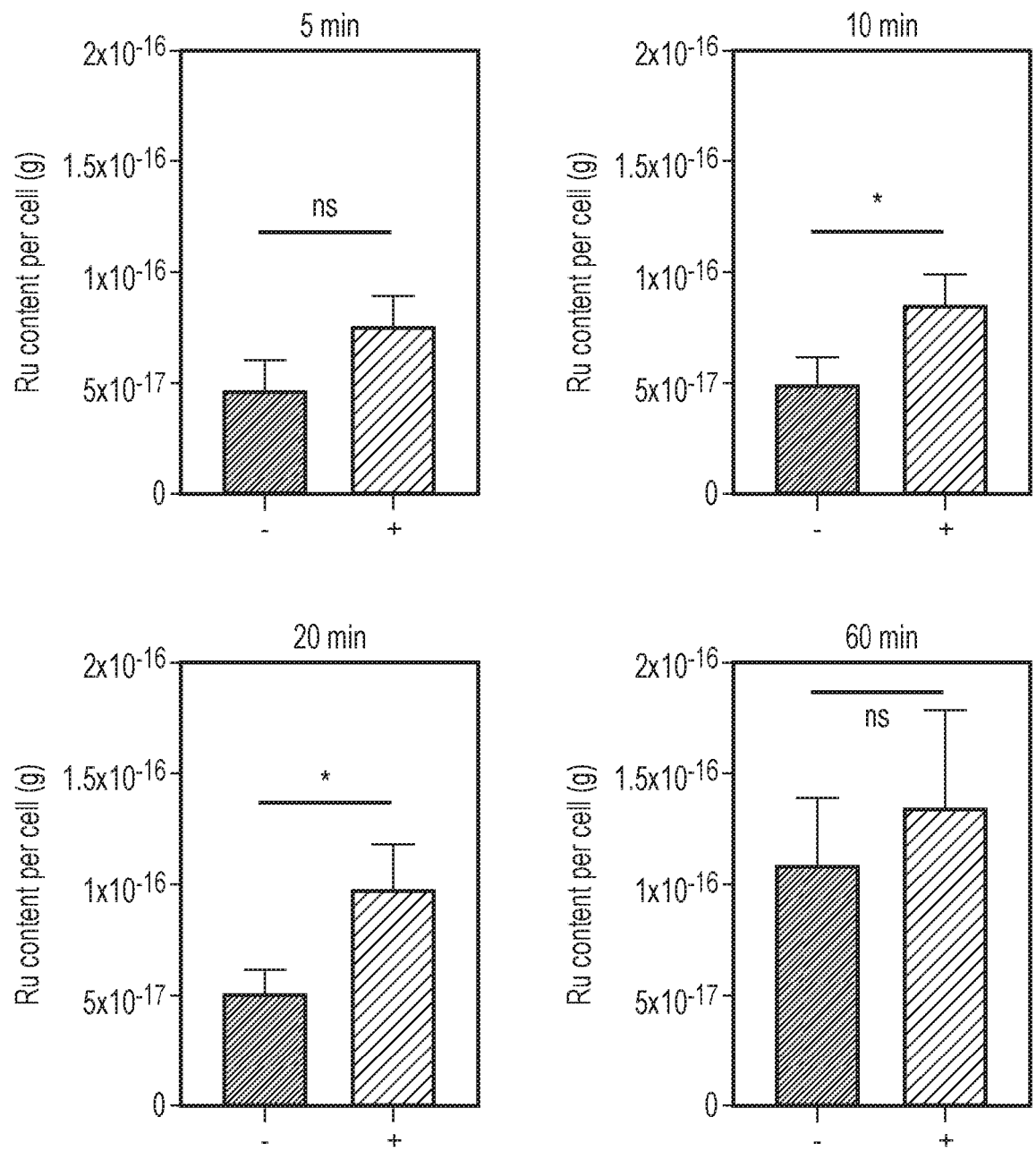
FIG. 9 shows the difference in Ru content per cell (g) at each time point (+) with glucose and (−) without glucose for $4^{4+}$. Showing significant differences in accumulation of ruthenium in the (+) with glucose sample at 10 and 20 minutes. Ruthenium content per cell determined via ICP-AES.

To investigate the uptake of $4^{4+}$ by *E. coli* cells, ICP-AES studies were carried out. Uptake studies with $4^{4+}$ were carried out in the presence and absence of glucose (see FIGS. 1B and 9). Experiments to investigate the accumulation of ruthenium in the *E. coli* EC958 over an hour were conducted as, at high concentrations, the time kill assays showed 99.9% of bacteria were killed within the first hour of exposure to $4^{4+}$. In these experiments, the concentration of iron, (a trace element in all cells) was also quantified as a control. It was found that on treatment with $4^{4+}$, iron content remained constant; furthermore there was also a negligible change in CFU/mL, demonstrating that cells were not lysed during the accumulation experiment.

In glucose-free conditions, accumulation shows two phases: after an initial increase on exposure, low levels of ruthenium are maintained for about 20 minutes, after which uptake gradually doubles to a final figure of $1.1 \times 10^{-16}$ g per cell. Assuming an average cell volume of 1 μm$^3$, this is equivalent to an intracellular concentration of >1 mM. Contrastingly, in the presence of glucose—although the amount of ruthenium that finally accumulates is identical within experimental error—the uptake of the complex is rapid, with the maximum intracellular concentration of ruthenium being reached within 20 minutes. The significant differences between the glucose and glucose-free conditions are seen at 10 and 20 minutes.

Figure 2:
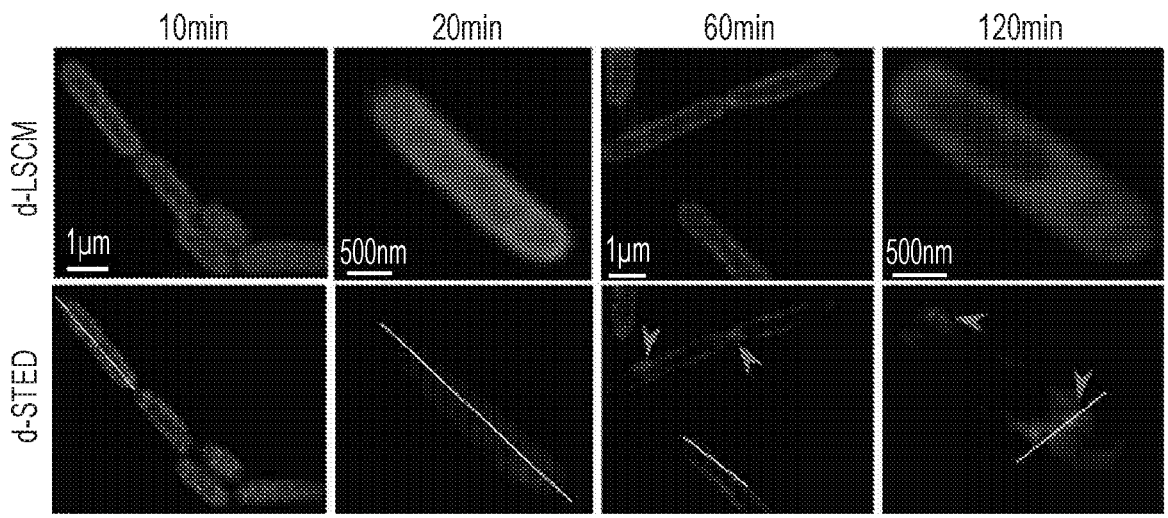
FIG. 2 shows the localization of $4^{4+}$ in *E. coli* EC958 cells visualized through Laser Scanning Confocal Microscopy (LSCM) and Stimulated Emission Depletion (STED) nanoscopy at 5, 20, 60, and 120 minutes. Top row: cells imaged using the emission of $4^{4+}$ on excitation at 470 nm with a White Light Laser and a 470 nm notch filter. Middle row: cells imaged with the same excitation and emissions settings; STED effect was obtained employing a 775 nm depletion laser, and a 780 nm vortex phase plate. Both deconvoluted diffraction-limited images (d-LSCM) and super resolution (d-STED) images were processed using commercial Huygens software (SVI). The arrowheads highlight regions where $4^{4+}$ preferentially accumulates. Bottom row: normalised emission intensity profile along the solid white lines drawn on top of selected region of cells shown in the middle row; solid black lines represent the d-LSCM, solid red lines represent d-STED. Conditions: after treatment with 0.8 µM $4^{4+}$, cells were washed with nitric acid before fixing with paraformaldehyde (16%).
Figure 2:
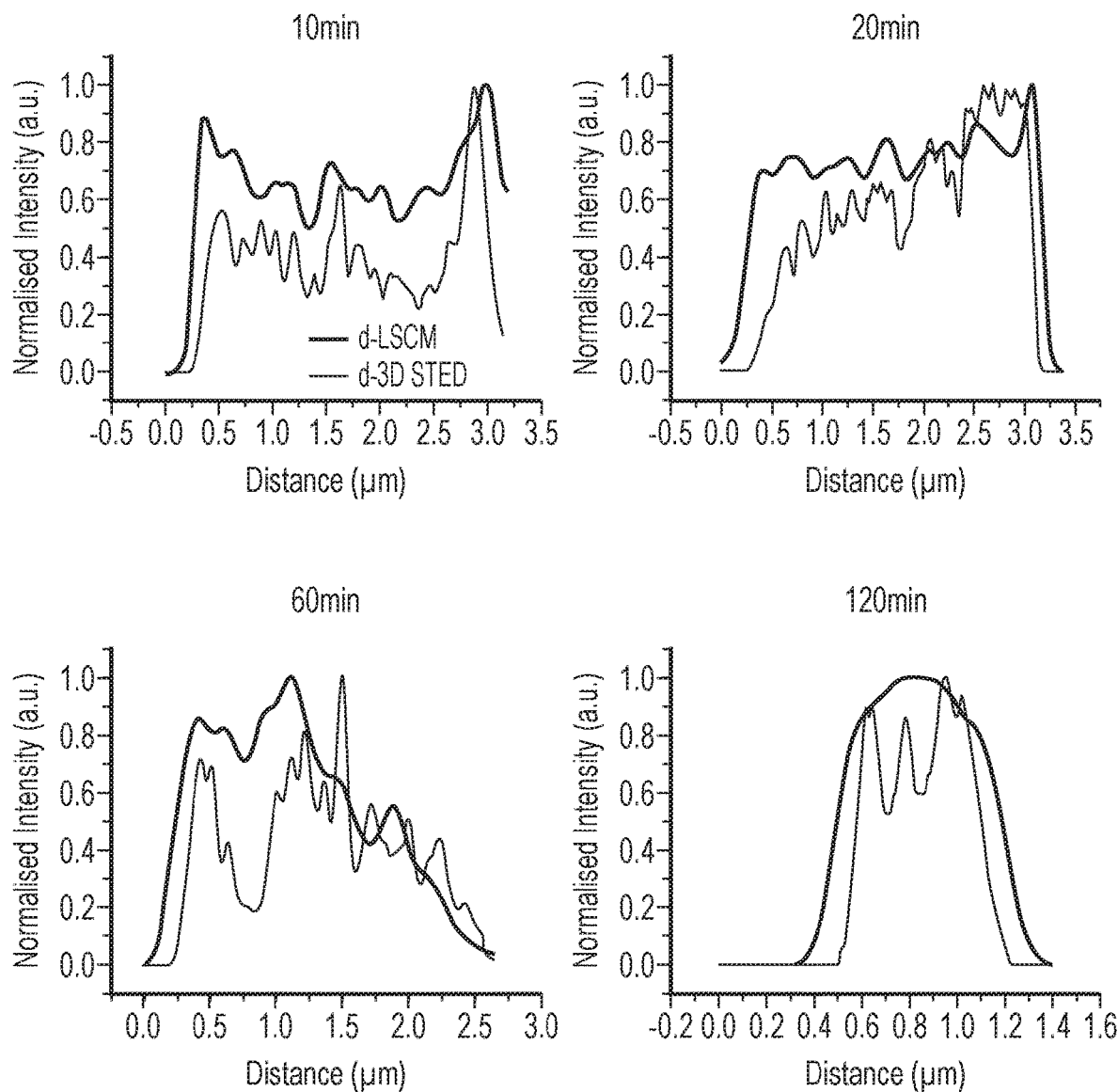

The uptake of $4^{4+}$ and the cellular response to exposure to $4^{4+}$ was also analysed at super resolution using a metal complex. Although structured illumination microscopy was used to image the internalization of $4^{4+}$ at improved resolutions (~100 nm), we also employed stimulated emission depletion (STED) nanoscopy, to provide the highest sub-diffraction limited resolutions. Example STED images taken over a time-course (5-120 minutes) are shown in FIG. 2.

To investigate whether changes in cell morphology occur within the first 5-20 minutes of exposure, images were taken at the same time points and identical conditions used in the accumulation experiments. These images confirmed that $4^{4+}$ is readily and rapidly taken up by the pathogenic strain of *E. coli*. Interestingly, up to 20 minutes, the complex largely accumulates at cellular membranes and is generally distributed within the cell compartment. However, after this period it increasingly preferentially locates at the cell poles.

Figure 3:
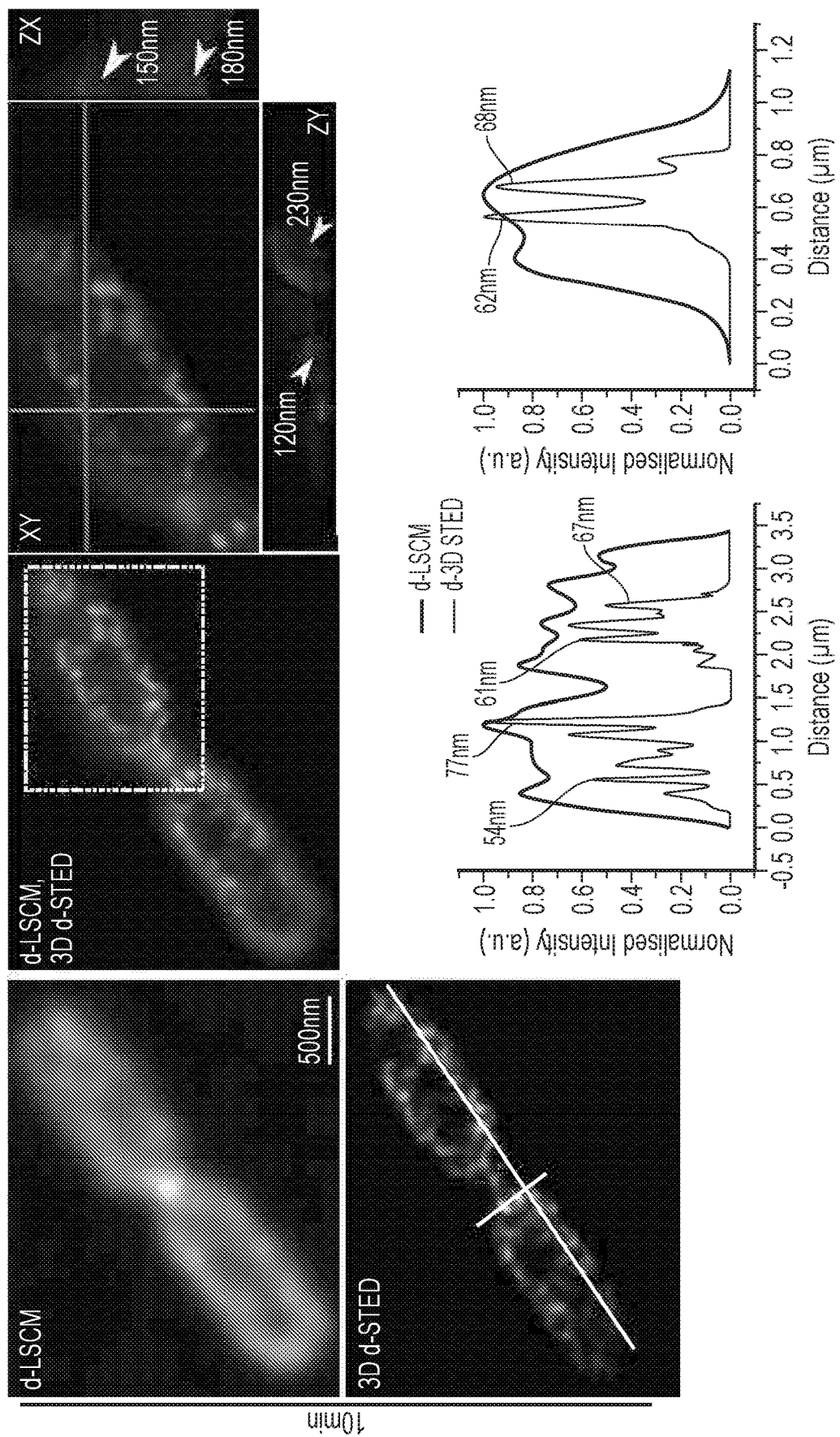
FIG. 3 displays representative images showing section planes of full-volume deconvoluted diffraction-limited cells and super-resolution images (d-LSCM and d-3D STED). Normalised emission intensity profile of the solid white lines drawn on top of selected region of cells are plotted. Solid black lines represent the d-LSCM, solid red lines represent d-3D STED. Zoomed-in areas of the dashed white squared drawn for each time point are shown adjacent to the images, as well as the orthogonal representation of every axis (XY, XZ, and YZ), where the increased resolution and better localisation of $4^{4+}$ is shown in green. The 10 and 20 minutes time points show accumulation at specific locations within the cell membrane; by the 60 minutes time point the compound localises at sections of the cell poles as can be seen in the zoomed in regions (a, b, c, d). Conditions used are identical to those employed in FIG. 2.
Figure 3:
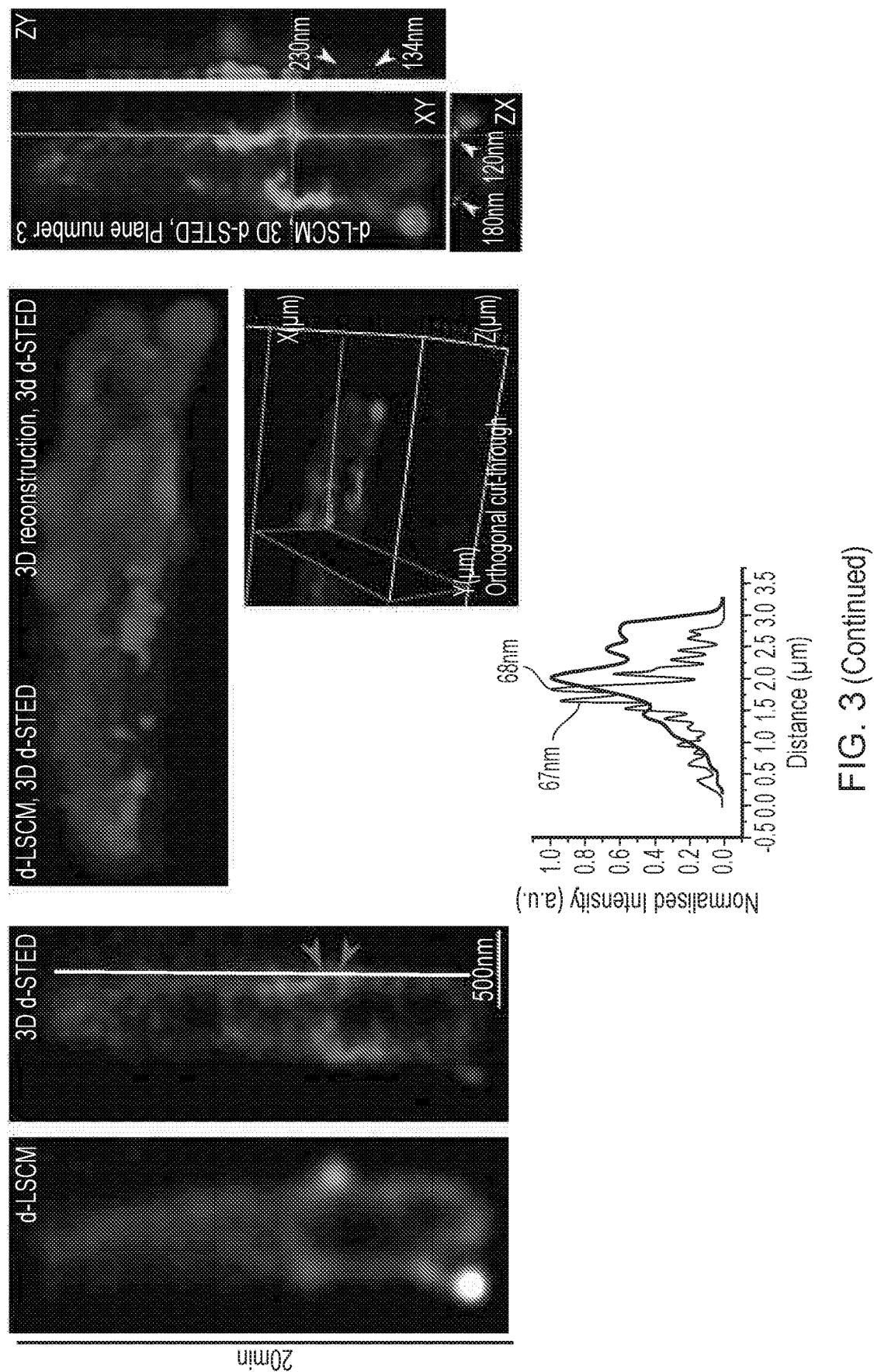
Figure 3:
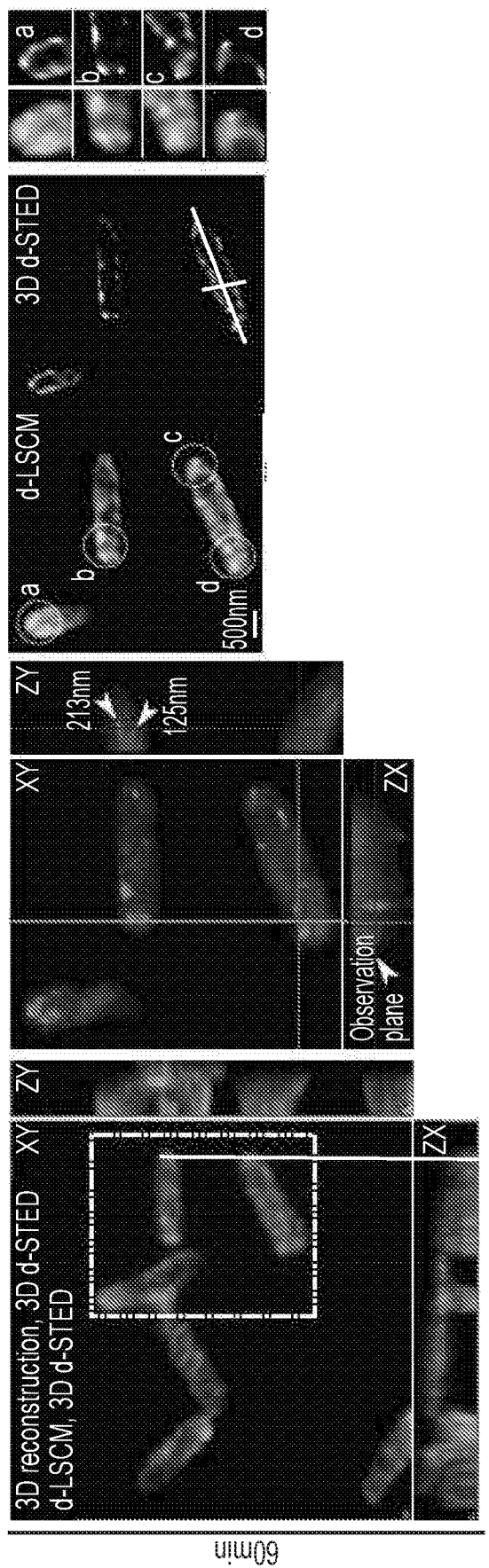
Figure 3:
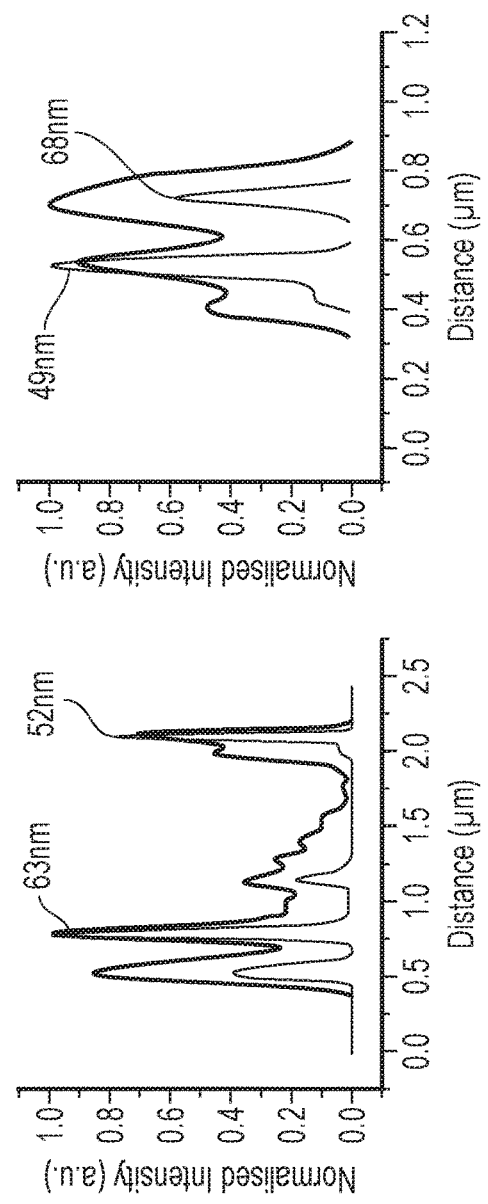

STED microscopy was also employed for detailed 3D sectioning experiments (3D STED). By employing a dual STED beam split into the XY plane and Z axis the highest possible 3D resolutions in each imaged plane was facilitated; a critical factor given the cellular dimensions of bacteria. Using this procedure, 3D STED resolutions of 50 nm in each plane and around 120 nm in the Z-axis were obtained. FIG. 3 shows images taken at specific time points after exposure to $4^{4+}$. During the first 10 min the probe accumulates within the cell membrane forming a distinctive distribution pattern. After 20 minutes dye redistribution begins and accumulation at the poles becomes increasingly apparent.

Taken together with the ICP-AES data the imaging studies indicate a change in the quality of uptake and intracellular distribution of the complex after around 20 minutes. Furthermore, as the molecular weight of $4^{4+}$ is considerably larger than the upper limit for porin-mediated uptake (~600 Da), this mechanism can be discounted. To investigate the possibility of membrane damage a second co-staining experiment with the probe Alexa Fluor NHS-ester 405 was carried out (see FIG. 4A).

Since Alexa Fluor NHS-ester 405 is impermeable to non-compromised bacterial membranes it localizes and images cell membranes. Following 5 minutes exposure to $4^{4+}$, localization of NHS-ester 405 is restricted to the cell membrane of bacteria. However, after 60 minutes exposure to the complex, both dyes are found to internalize within *E. coli*. In contrast, even after 60 minutes, cells solely stained with NHS-ester 405 continue exclusively to display membrane staining. The fact that the membrane stain is internalized only after treatment with $4^{4+}$ offers further evidence that the complex is disrupting the structure of bacterial membranes. To investigate this phenomenon more quantitatively, concentration-dependent ATP cellular leakage assays were performed. Following treatment with specific concentrations of $4^{4+}$, the presence of extracellular ATP, released from damage to bacterial cell membranes, was detected using the luminescence generated from the ATP-dependent reaction between recombinant firefly luciferase and D-luciferin.

Figure 4:
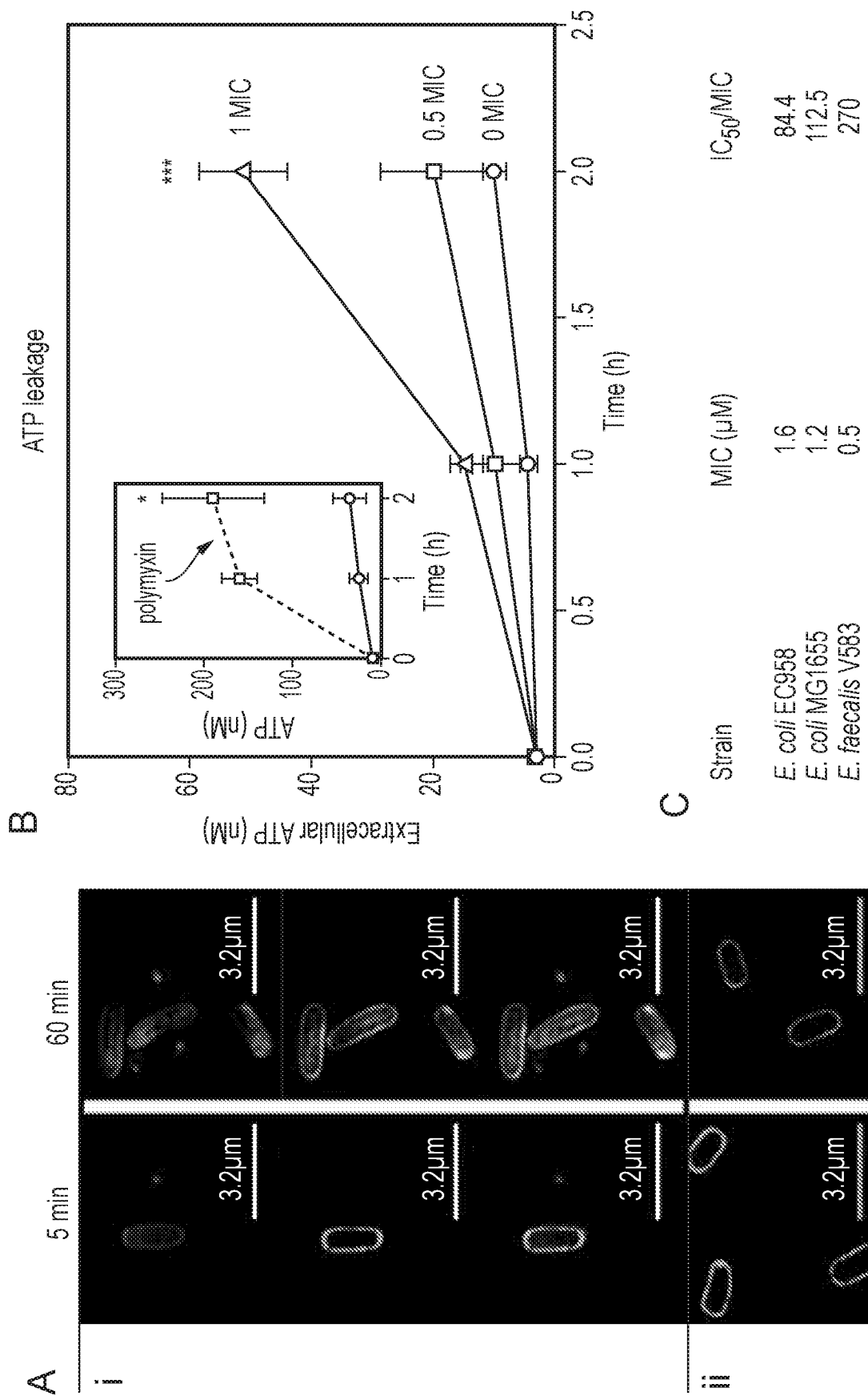
FIG. 4A shows evidence of membrane damage in *E. coli* EC958. Co-localization of $4^{4+}$ and NHS-ester 405 visualized through SIM at 5 minutes (left), and 60 minutes (right). (i) Cells treated with 0.8 μM $4^{4+}$ and fixed with paraformaldehyde (16%). After fixation cells were treated with 2.5 μg/mL of NHS-ester 405. Top panel: emission of $4^{4+}$ (A568 filter) middle panel: NHS-ester 405 emission at 405 nm (DAPI filter Bottom panel: merged images. (ii). Staining with NHS-ester in the absence of $4^{4+}$.
FIG. 4B shows $4^{4+}$ induced ATP release from EC958 cells, extracellular [ATP] (nM) quantified with recombinant luciferase and D-luciferin with ATP released measured on a luminometer for samples exposed to 0 (control), 0.8 and 1.6 μM (MIC) of $4^{4+}$ over a period of two hours. A three-star significant difference is observed between 0 and 1 MIC, P value=0.0006. Error bars represent three biological repeats±SD. ATP positive contro—polymyxin 4 μg/mL (inset). $IC_{50}$/MIC comparison for HEK293 cells and three bacteria strains.
FIG. 4C shows $IC_{50}$/MIC comparison for HEK293 cells and three bacteria strains.
FIG. 4D shows a *Galleria mellonella* toxicity screen Kaplan-Meier survival curves, cells treated with 0-80 mg/kg of compound $4^{4+}$, incubated at 37.5° C. for 120 hours—water control (black), compound $4^{4+}$ (red).
Figure 4:
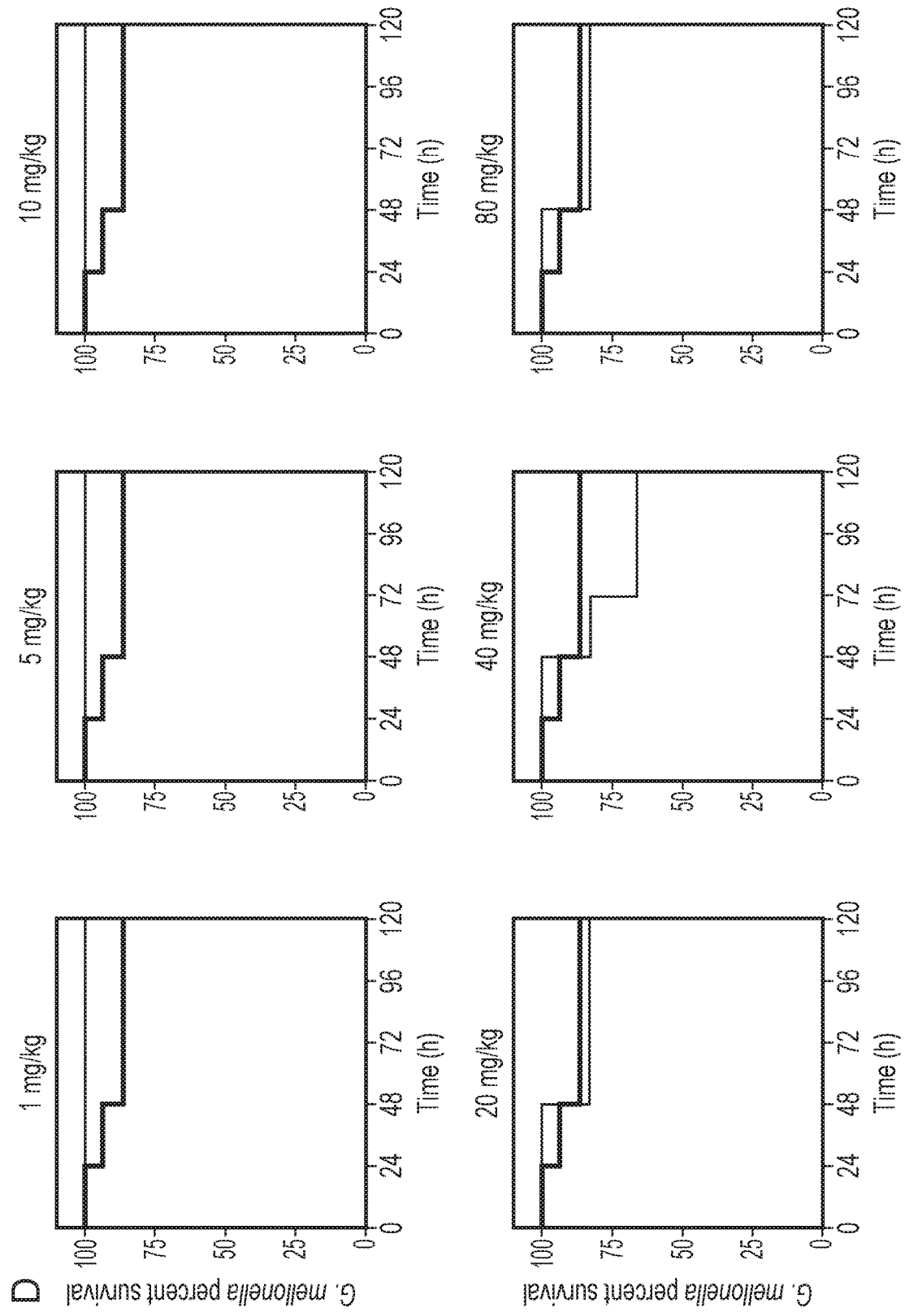

Data obtained from the luminescence-based determination of [ATP], summarized in FIG. 4B, confirm that bacterial membranes are compromised in a concentration-dependent manner on exposure to $4^{4+}$. Given this effect, it seems likely that the uptake of the complex in glucose-free conditions is biphasic, as membrane damage must initially occur before the level of internalized $4^{4+}$ can rise to high concentration. It is possible that this membrane damage is the sole mechanism of therapeutic action for the complex; although—once internalized—the complex localizes and binds at specific regions of the cell suggesting a second cellular target. Given that pathogenic, therapeutically-resistant, strains of *E. coli* are still sensitive to the complex, it seems likely that the membrane disruption effect of $4^{4+}$ may only be one facet of a more complex set of interactions and cellular responses.

TABLE 2

UV-Vis spectroscopy data showing the molar extinction coefficient and absorption maxima for the four [{Ru(N—N)$_2$}$_2$(tpphz)] in water and MeCN. Conducted on a Cary 300 UV/Vis spectrophotometer at 27.5° C.

| Complex | | λmax/nm | ε/M$^{-1}$ cm$^{-1}$ | Transition |
|---|---|---|---|---|
| $1^{4+}$ | in water | 450 | 34000 | MLCT |
| $2^{4+}$ | in water | insoluble | — | — |
| $3^{4+}$ | in water | 454 | 25300 | MLCT |
| $4^{4+}$ | in water | 430 | 22833 | MLCT |
| $1^{4+}$ | in MeCN | 450 | 27000 | MLCT |
| $2^{4+}$ | in MeCN | 450 | 41000 | — |
| $3^{4+}$ | in MeCN | 449 | 22700 | MLCT |
| $4^{4+}$ | in MeCN | 432 | 19498 | MLCT |

TABLE 3

Luminescent emission data showing the molar extinction coefficient and absorption maxima for the four [{Ru(N—N)$_2$}$_2$(tpphz)] in water and MeCN. Conducted on a Fluoromax 3 fluorimeter at 27.5° C.

| Complex | λmax/nm (MeCN) | λmax/nm (water) |
|---|---|---|
| $1^{4+}$ | 710 | — |
| $2^{4+}$ | 660 | insoluble |
| $3^{4+}$ | 670 | 600 |
| $4^{4+}$ | 670 | 650 |

As $4^{4+}$ shows high antimicrobial activity and is membrane targeting, the potency of the compound in noncancerous eukaryotic cells was determined to further explore its potential as an antimicrobial theranostic lead. MU-assays on the human embryonic kidney line, HEK293 revealed an average IC$_{50}$ value of 135 μM, indicating at least an 80-fold magnitude difference in inhibitory concentration against bacteria and HEK293 cells (see FIG. 4C).

Given the promising comparison between IC$_{50}$ and MIC values, an animal model screen was carried out. As many aspects of the physiology of *Galleria mellonella* larvae, particularly their immune system, are very similar to mammals they are much employed as an in vivo model, including as a toxicity screen, yielding results that are comparable to commonly used mammalian models. A toxicity screen was conducted with $4^{4+}$ and Kaplan-Meier survival curves plotted (see FIG. 4D). All concentrations used were above the MIC for $4^{4+}$ against EC958, and within the daily dose range used in the clinic for antimicrobials. From Log-rank tests it was determined that there was no significant difference between the percentage survival with the *Galleria* treated with $4^{4+}$ and the control at all compound concentrations. In addition, activity and melanisation scores showed that there was no significant negative effects on the *Galleria* exposed to $4^{4+}$, confirming that this compound is not toxic at concentrations well above the MIC.

TABLE 4

Figure 10A:
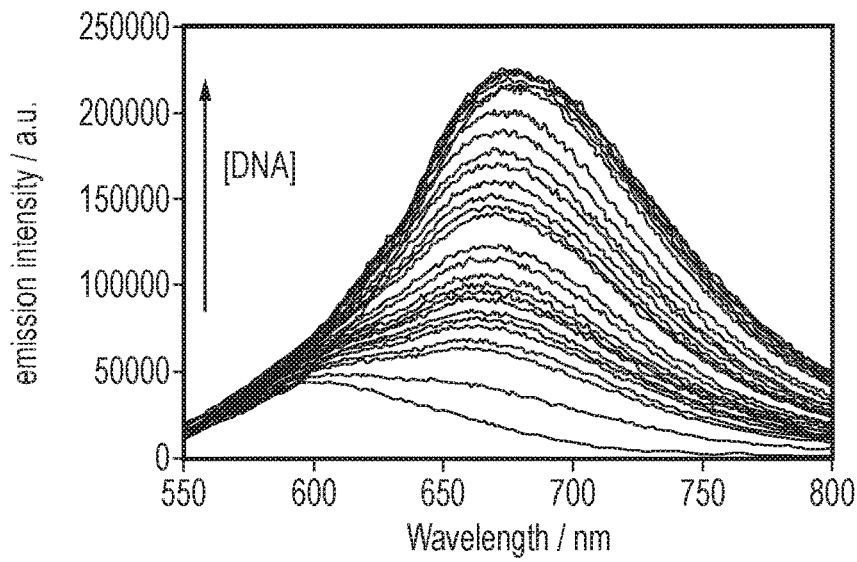
FIG. 10A shows DNA binding titration using increasing concentrations of CT-DNA and $4^{4+}$ in Tris buffer at 27° C., conducted on a Fluoromax 3.
Figure 10B:
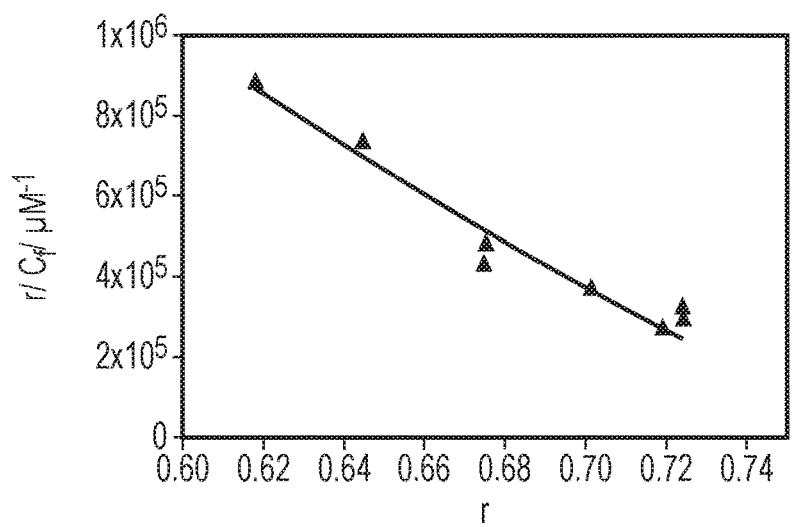
FIG. 10B shows a scatchard plot and McGhee Von Hippel fit, to find the binding constant of $4^{4+}$.

DNA binding constants, and site sizes of four compounds described herein (FIG. 10)

| Complex | $I_b/I_f$ | $K_b$ | n |
|---|---|---|---|
| $1^{4+}$ | 60 | 1.1 × 10$^7$ | 2.9 |
| $2^{4+}$ | 17 | 5.6 × 10$^6$ | 1.26 ± 0.02 |
| $3^{4+}$ | 27 | 6.7 × 10$^6$ | 1.45 ± 0.02 |
| $4^{4+}$ | 10 | 2.4 × 10$^6$ | 0.92 ± 0.02 |

TABLE 5 log-rank (Mantel-Cox) tests on the Kaplan-Meier survival curves to determine whether a significant difference is observed between the control (water) and compound injected Galleria survival percentages. Galleria were injected with 10 μL of compound (0-80 mg/kg) and stored at 37.5° C. for 120 hours.

| Concentration/ mg kg$^{-1}$ | Chi square | P | Survival curve sig different |
|---|---|---|---|
| 1 | 0.83 | 0.36 | No |
| 5 | 0.83 | 0.36 | No |
| 10 | 0.83 | 0.36 | No |
| 20 | 0.87 | 0.35 | No |
| 40 | 0.87 | 0.35 | No |
| 80 | 0.02 | 0.88 | No |

Figure 11A:
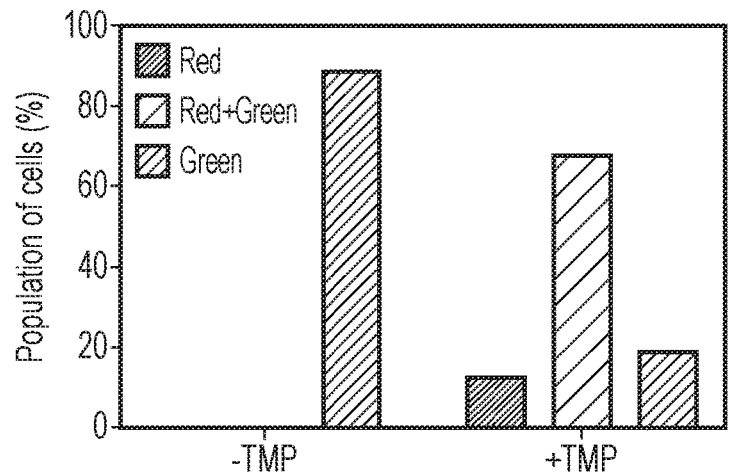
FIGS. 11A and 11B show the detection of membrane potential in *E. coli* EC958 cells. The percentage population of cells (%) containing red/red+green/green fluorescence are given. Cells were incubated with 30 μM of Di-OC2(3) for 30 minutes in the presence or absence of 1.6 μM of $4^{4+}$.
Figure 11B:
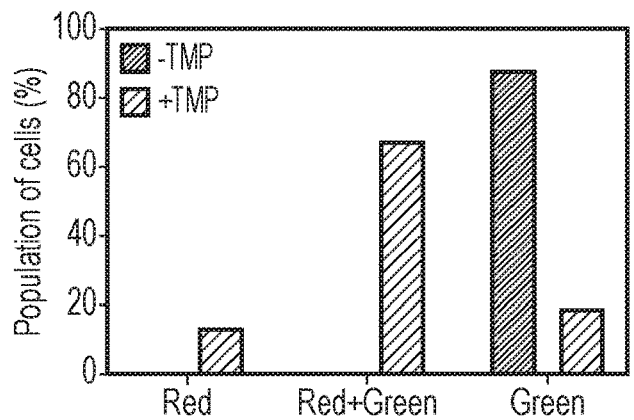
Figure 12A:
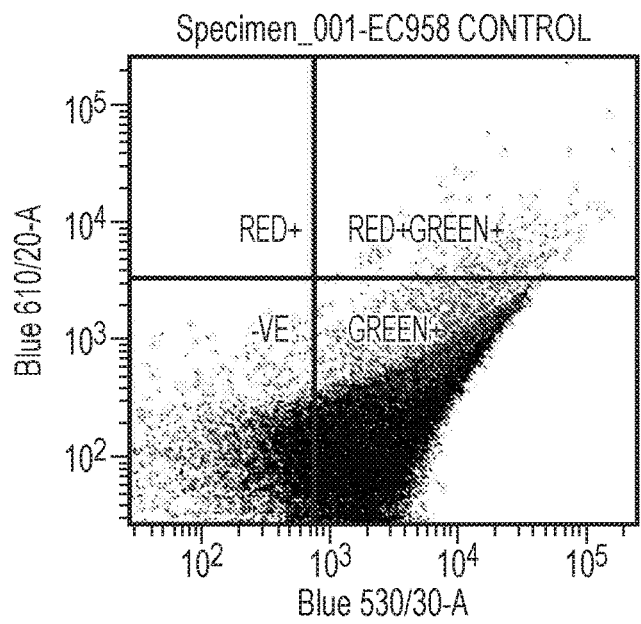
FIGS. 12A and 12B show the analysis of the flow cytometry data using red and green fluorescence parameters. The red-versus-green fluorescence dot plots were collected with log amplification.
Figure 12B:
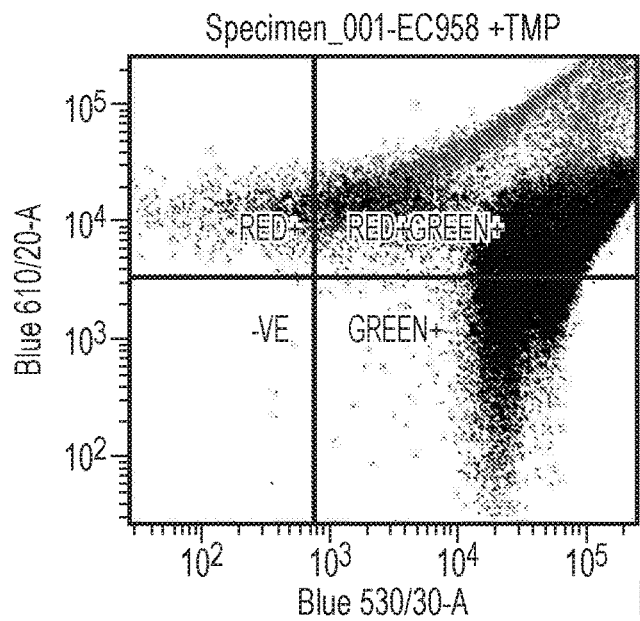
Figure 13:
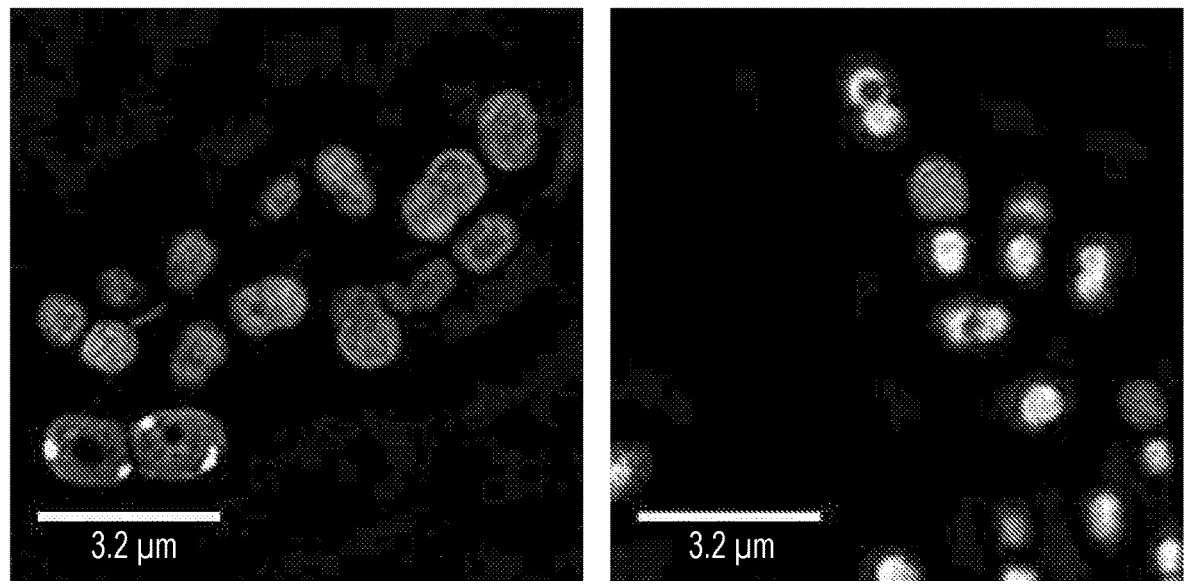
FIG. 13 shows Acetinobacter *baumannii* (AB184) stained with $4^{4+}$ at MIC concentration at 10 minutes (left) and 60 minutes (right), corresponding to imaging of the outer membrane (10 minutes) and the inner membrane (60 minutes). Cells fixed with PFA (4%) and washed with PBS. Cells were imaged on a structured illumination microscope using the 488 nm laser and an A568 filter.
Figure 17:
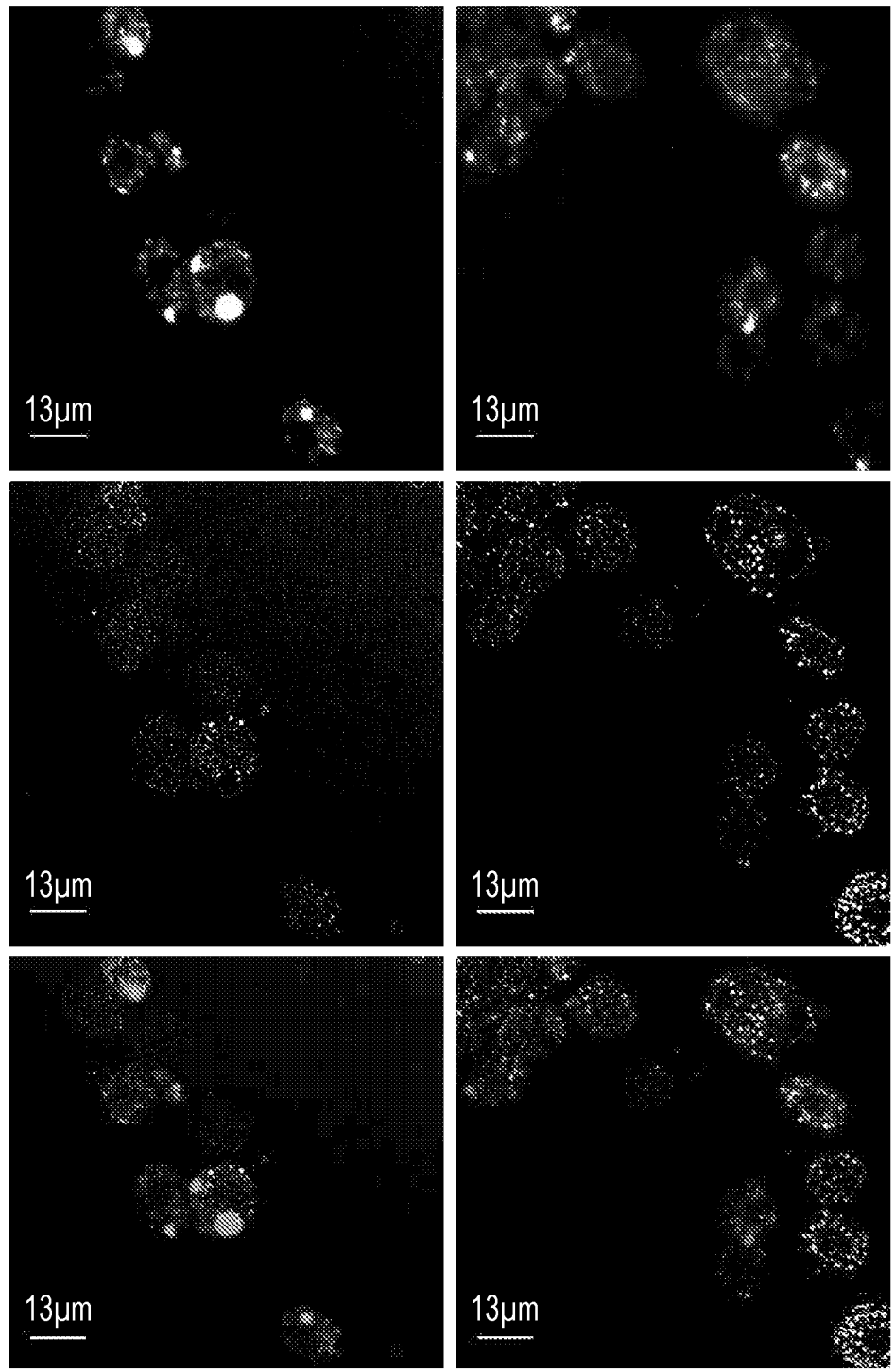
FIG. 17 shows the localization of $4^{4+}$ in *A. baumannii* AB184 cells within the larvae's hemolymph using confocal microscopy. Top Row: cells imaged using the emission of $4^{4+}$ on excitation at 450 nm using A568 filter. Middle row: phase contrast. Bottom Row: combined image. Extracted hemolymph cells were washed with nitric acid before fixing with paraformaldehyde (16%).

The membrane potentials and flow cytometry behaviour of $4^{4+}$ were determined, as shown in FIGS. 11 and 12. Further, it has been shown that $4^{4+}$ at MIC concentration can penetrate *Acetinobacter baumannii* (AB184) (FIG. 13). At 10 minutes, the outer membrane can be imaged, at 60, the inner membrane. The localization of $4^{4+}$ in *A. baumannii* AB184 cells within the larvae's hemolymph is shown in FIG. 17.

Figure 14:
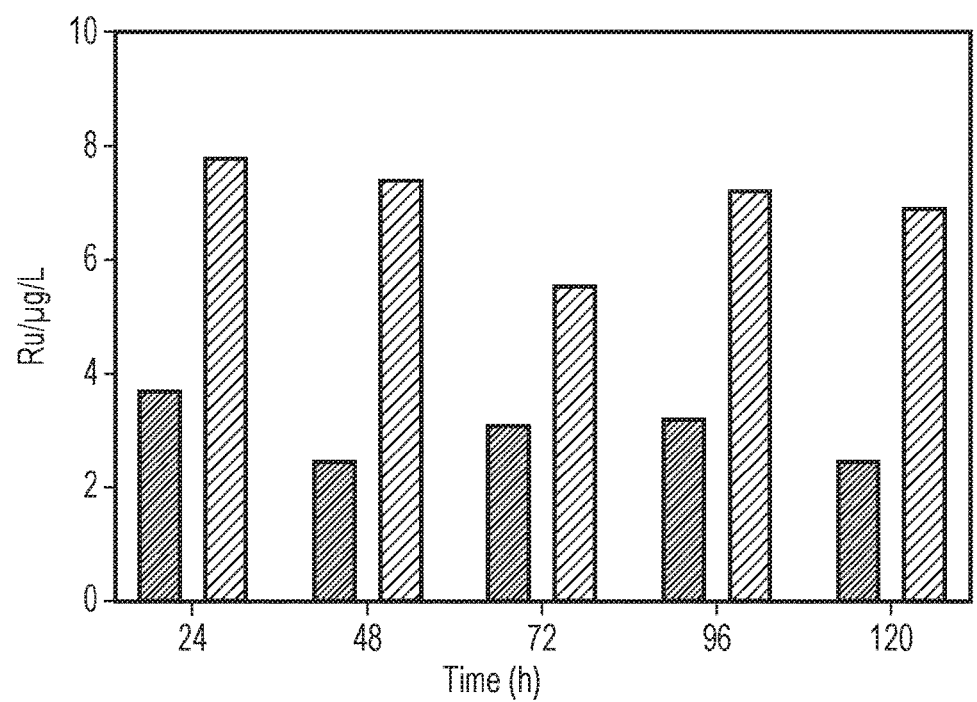
FIG. 14 shows the ruthenium haemolymph content (μg/mL) for *Galleria mellonella* injected with 20 mg/kg (blue) and 80 mg/kg (red). *Galleria* were injected with 10 μL $4^{4+}$/water into their left pro-leg, incubated at 37.5° C. for 120 hours. At each time interval, the *Galleria* were scored: live/dead, activity and melanisation. Ru content was determined via ICP-AES.
Figure 15:
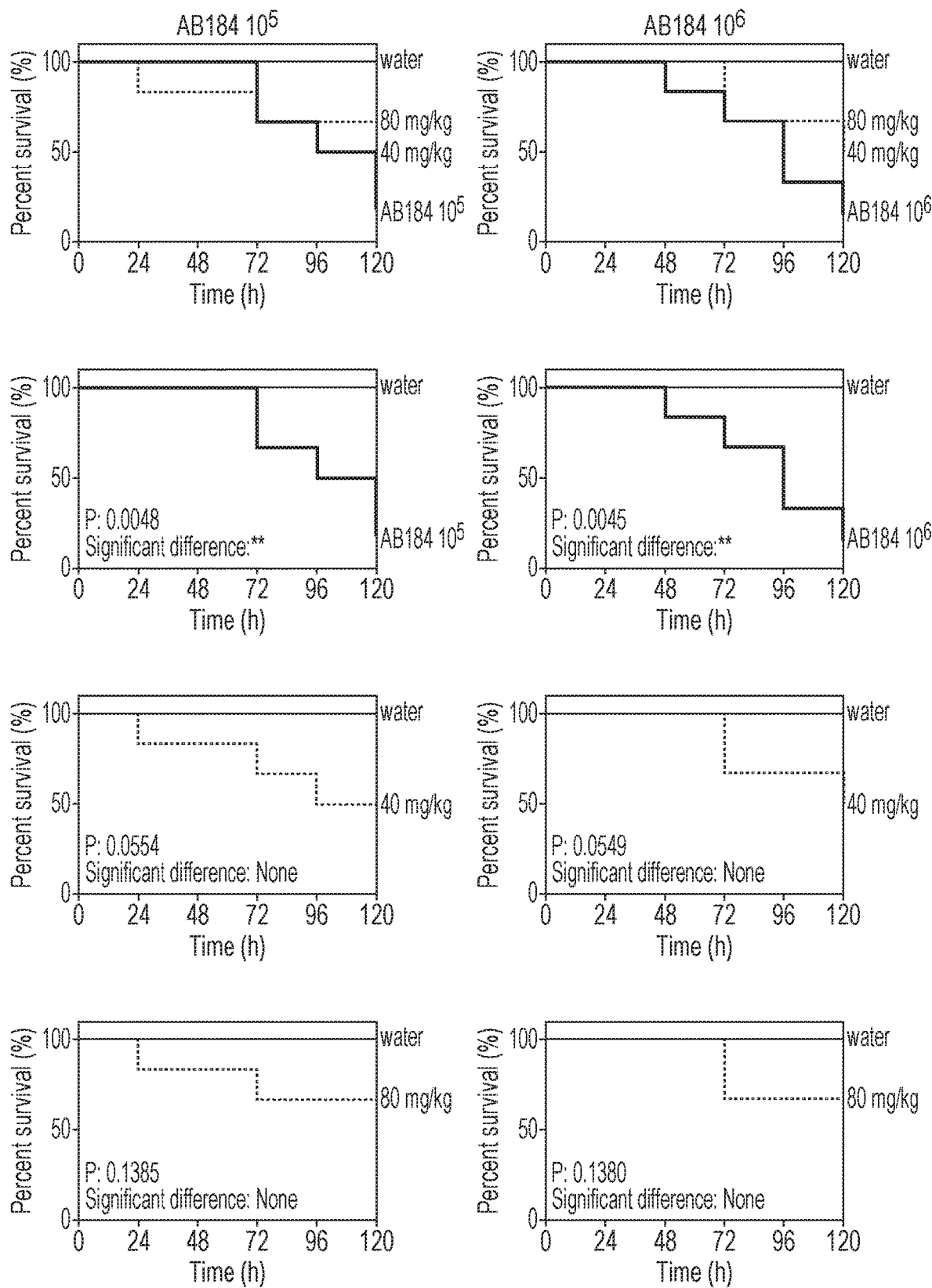
FIG. 15 shows *Galleria mellonella* (CFU $10^5$—left and $10^6$—right) toxicity screen Kaplan-Meier survival curves, cells treated with 0-80 mg/kg of $4^{4+}$, incubated at 37.5° C. for 120 hours—water control (orange), bacteria (green) and $4^{4+}$ (purple). Co-injected larvae were injected with bacteria in their right pro-leg then $4^4$+30 minutes later in their left pro-leg.
Figure 16:
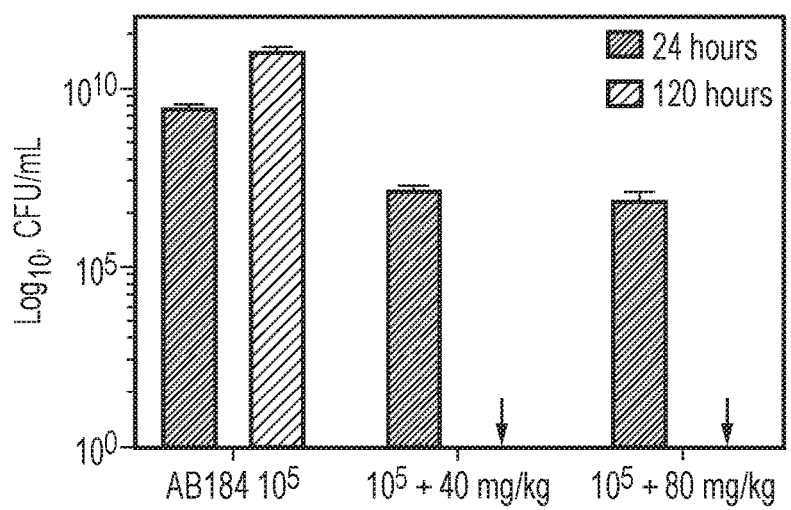
FIG. 16A shows the Bacteria CFU counts from extracted larvae hemolymph (*Galleria mellonella*), observed for 120 hours in the presence of 40 mg/kg and 80 mg/kg $4^{4+}$, with extractions taken at 24 and 120 hours. Initial bacterial count $10^5$ (left) and $10^6$ (right). Larvae were incubated at 37.5° C.
FIG. 16B shows photographs of the agar plates used to determine the plots of FIG. 16A and show a 0 mg/kg, 40 mg/kg and 80 mg/kg dosing of $4^{4+}$ after 24 hours. Complete clearance was observed in 96 hours at 40 and 80 mg/kg doses, with a single dose. The black marks are not bacteria colonies, but melanised hemolymph.
Figure 16:
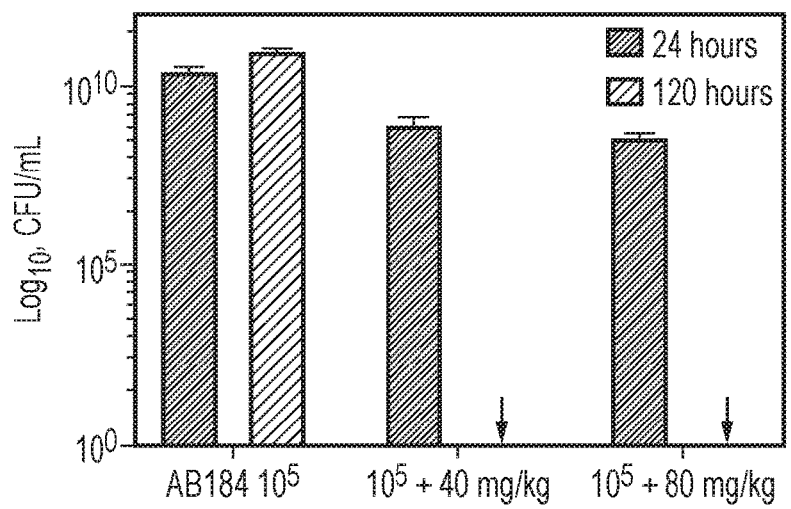
Figure 16:
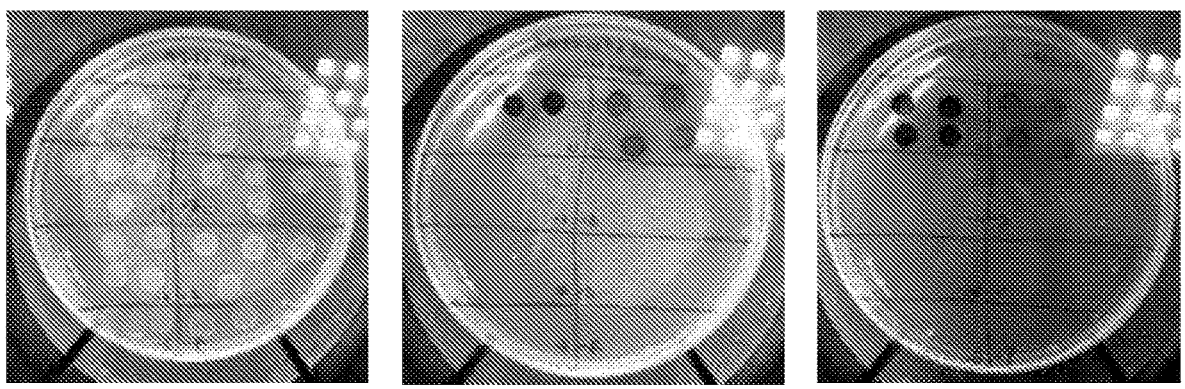

Ruthenium haemolymph content (μg/mL) was determined in *Galleria mellonella* injected with $4^{4+}$ (FIG. 14). As would be expected, at higher doses, the ruthenium content is higher in the haemolymph, although this remains largely constant over the duration of the experiment. Kaplan Meier infection models (FIG. 15) show good survival at both concentrations of $4^{4+}$ (40 mg/kg and 80 mg/kg) relative to the control (water). Further, FIGS. 16A and 16B show the Bacteria CFU counts from extracted larvae hemolymph (*Galleria* bacteria). From these plots it is clear that after 48 hours under both treatment concentrations (40 or 80 mg/kg of $4^{4+}$) the colonies were cleared. This clearance was achieved from a single compound dose. In comparison, an exponential increase in bacterial growth was observed in the absence of $4^{4+}$.

The *Galleria mellonella* larvae were selected for further study, using the CUBIC clearing protocol. FIG. 18 shows images taken through cleared *Galleria* wax moth larvae. The luminescence of $4^{4+}$ stained *A. baumannii* cells at the head (A) and tail (B) of *Galleria Mellonella*. Regions of *A. baumannii* cells are highlighted (I,II). Initiation of an immune response in *Galleria* hemolymph cells is observed (C). The images show the *A. baumannii* stained with $4^{4+}$ are taken up by the larvae's hemocyte cells and phagocytosed. This indicates that not only does $4^{4+}$ kill the bacteria but it also upregulates the larvae's immune response allowing the infection to be cleared. FIG. 19 also shows images of cleared larvae infected with *A. baumannii*, AB184, stained with NHS-ester 488 (A) or $4^{4+}$ (B). Sections of the cells are identified (i) and expanded (AII, AIII, BII) to show *A. baumannii* within the hemocyte cells. 3D surface plots (AIV, BIII) are given to show peak emission intensity.

In FIG. 20, a study of biofilm formation of *E. coli* ST131, EC958, when subjected to complex $4^{4+}$ is presented. ST131 formed biofilms in the absence of $4^{4+}$, and at 10% of MIC. Welch's T-test showed no significant difference between these groups (P=0.687). Concentrations of 0.390 and 0.781 showed no biofilm formation having minor negative values of 0.003 and 0.005 respectively. As such, $4^{4+}$ prevents biofilms from forming at concentrations as low at 0.390 μM. FIG. 21 shows a study with pre-formed biolfilms. The biofilms were subjected to 15.6 μM, 78 μM and 156 μM of $4^{4+}$. A one-star significant difference was observed between the control (0 μM) and 156 μM samples (p value=0.0015), and a two-star significant difference was observed between the control (0 μM) and 15.6 μM samples (p value=0.0086). Therefore, $4^{4+}$ has an ability to prevent biofilm formation, and to penetrate existing biofilms.

Synthesis of Mononuclear Complexes

Complexes $1^{2+}$ and $2^{2+}$ (see scheme 2) were synthesized using the procedures outlined below.

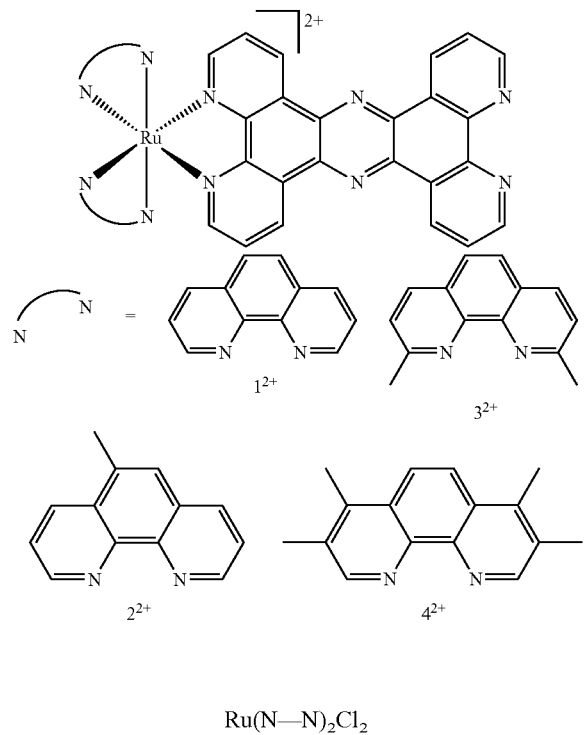

Scheme 2. Compounds $1^{4+}$ to $4^{4+}$

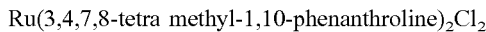

Ru(N—N)$_2$Cl$_2$

Four compounds were synthesised by the following method, where N—N represents the substituted phenanthroline ancillary ligand. RuCl$_3$.3H$_2$O, N—N and LiCl were heated in DMF for 8 hours under reflux. The reaction mixture was cooled to room temperature and acetone added. This was stored at 4° C. for 16 hours. The dark purple precipitate was washed with water and ethanol and dried in vacuo.

Ru(3,4,7,8-tetra methyl-1,10-phenanthroline)$_2$Cl$_2$

RuCl$_3$.3H$_2$O (1.14 g, 5.50 mmol), TMP (2.4 g, 10.16 mmol), LiCl (1.47 g, 34.68 mmol), DMF (19 mL) and acetone (100 mL). Mass=2.07 g (3.21 mmol, 63.2%) purple solid. MS m/z (%): 609.1 (62) [M−Cl]$^+$, 637.1 (100) [M]$^+$ 667.1. (44) [M+Na]$^+$. Carbon monoxide displaced one of the chlorines.

[Ru(N—N)$_2$(DPQ)][PF$_6$]$_2$

Four compounds were synthesised by the following general procedure. [Ru(N—N)$_2$Cl$_2$] and DPQ were suspended in a 1:1 solution of EtOH:H$_2$O. The suspension was refluxed for 12 hours under argon, cooled to room temperature and filtered. NH$_4$PF$_6$ was added to form a brown hexafluorophosphate salt.

[Ru(3,4,7,8-tetra methyl-1,10-phenanthroline)(DPQ)][PF$_6$]$_2$

[Ru(TMP)$_2$Cl$_2$] (1.01 g, 1.57 mmol), DPQ (0.495 g, 2.36 mmol) and EtOH:H$_2$O (50 mL). Mass=0.861 g (0.801 mmol, 51%). MS(TOF MS LD+) m/z (%): 784 (51) [M−2PF$_6$]$^{2+}$, 929 (100) [M−PF$_6$]$^+$. 1 HNMR (DMSO-d$^6$) δ (splitting integration): 2.23 (6H, s), 2.39 (6H, s), 2.79 (6H, s), 2.85 (6H, s), 7.46 (2H, dd), 7.85 (2H, d), 7.65 (2H, s), 7.95 (2H, s), 8.41 (4H, d), 8.48 (2H, d).

[Ru(N—N)$_2$(tpphz)][PF$_6$]$_2$

Four compounds were synthesised by the following general procedure. 5,6-diamino-1,10-phenanthroline was dissolved in hot methanol, this was added to a boiling solution of [Ru(N—N)$_2$DPQ][PF$_6$]$_2$ in acetonitrile. The reaction mixture was heated to reflux at 80° C. for 6 hours. The solution was cooled to room temperature and filtered. NH$_4$PF$_6$ was added to form a red hexafluorophosphate salt. The crude product was washed with water, ethanol and diethyl ether. It was then purified on a grade I alumina column with acetonitrile/water/KNO$_3$. The red band was collected, the solvent removed under reduced pressure and the red solid dried in vacuo.

[Ru(3,4,7,8-tetramethyl-1,10-phenanthroline)(tpphz)][PF$_6$]$_2$ 5,6-diamino-1,10-phenanthroline (88.2 mg, 0.42 mmol), hot methanol (17 mL), [Ru(TMP)$_2$DPQ][PF$_6$]$_2$ (606 mg, 0.56 mmol), acetonitrile (30 mL). Mass=0.272 g (0.389 mmol, 45%), 1 HNMR (CD$_3$CN-d$^6$) δ (splitting integration): 2.29 (6H, s), 2.32 (6H, s), 2.80 (6H, s), 2.86 (6H, s), 7.71-7.78 (4H, m), 7.84 (4H, s), 8.15 (4H, d), 9.30 (4H, d), 9.59 (4H, d). MS; m/z (%): 479 [M−2(PF$_6$)]$^{2+}$. Accurate mass analysis: C$_{56}$H$_{44}$N$_{10}$[$^{102}$Ru]$^{2+}$ Calculated 479.1391. Found 479.1405.

Properties of Mononuclear Complexes

The same parameters and conditions used above to determine MIC and MBC values with respect to compounds $1^{4+}$ to $4^{4+}$ were employed in order to test the MIC and MBC values of complexes $1^{2+}$ to $4^{2+}$.

TABLE 6

MIC results in for mononuclear complexes

| Complex | MG1655 | EC958 | V583 | SH1000 | PA2017 | AB184 |
|---|---|---|---|---|---|---|
| | | Defined Medium Values | | | | |
| $1^{2+}$ | 17.5 | 34.9 | 69.8 | 69.8 | 34.9 | 17.5 |
| $2^{2+}$ | 33.9 | 33.9 | 135.6 | 33.9 | 16.9 | 16.4 |
| $3^{2+}$ | 8.2 | 16.5 | 35.8 | 32.9 | 16.4 | 8.5 |
| $4^{2+}$ | 3.9 | 3.9 | 31.1 | 7.8 | 7.8 | 3.6 |
| ampicillin | 5 | — | 7.5 | 5 | — | — |

TABLE 7

MBC results in for mononuclear complexes

| Complex | MG1655 | EC958 | V583 | SH1000 | PA2017 | AB184 |
|---|---|---|---|---|---|---|
| | | Defined Medium Values | | | | |
| $1^{2+}$ | 34.9 | 17.5 | 279.5 | 69.8 | 34.9 | 34.9 |
| $2^{2+}$ | 33.9 | 17 | 271.2 | 33.9 | 16.9 | 16.9 |
| $3^{2+}$ | 8.2 | 16.5 | 131.7 | 32.9 | 32.9 | 8.2 |
| $4^{2+}$ | 3.9 | 3.9 | 31.1 | 7.8 | 7.8 | 3.6 |
| ampicillin | 10 | — | 7.5 | 10 | — | — |

As can be seen from Tables 6 and 7, antimicrobial activity was determined from each of compound $1^{2+}$ to $4^{2+}$. Moreover, compound $4^{2+}$ was found to show surprising efficacy as an antibiotic, with better properties than existing antibiotics such as ampicillin. For the avoidance of doubt; SH1000 is *Staphylococcus aureus*; AB184 is acetinobacter *baumanii*; and PA2017 is *pseudomonas* auriginosa.

Having established that complex $4^{2+}$ had the most promising bactericidal properties, DNA binding (FIG. 22) and time-kill kinetics assays were carried out for *E. coli* during exposure to increasing concentrations of the complex in minimal media at 37° C. (see FIG. 23). In the presence of glucose, efflux mechanism is observed, clearly indicating that the complex can be actively transported in and out of the cell. FIG. 24 shows the difference in Ru content per cell (g) at the time intervals for FIG. 23, the Ru content is generally higher in the presence of glucose at 5, 10 and 20 minutes, with significant differences observed after 10 minutes.

*E. coli* cells treated with $4^{2+}$ at MIC concentration at 1, 2 and 24 hours have shown the onset of multi-nucleated cell filamentation when $4^{2+}$ is present (FIGS. 26 A-C and FIG. 27). This indicates that cell death is caused by DNA damage in the presence of this complex. In FIG. 27, a direct overlay of DAPI and $4^{2+}$ gives a Pearson's colocalisation constant of >0.9. This constant indicates a strong colocalisation confirming $4^{2+}$ targets *S. aureus* DNA. To corroborate the observations in FIGS. 26 and 27, the mutagenic properties of $4^{2+}$ on *E. coli* were determined using an Ames mutagenic assay (FIG. 28), as compared to natural mutagenesis and UV-irradiation. At and above the MIC levels of $4^{2+}$ significant DNA mutagenesis is observed, at twice the MIC this is close to the levels observed for UV Irradiation, indicating that $4^{2+}$ causes damage to bacterial cell DNA, as observed in the filamentation shown in FIG. 26. FIG. 29 shows TEM images of *E. Coli* after treatment with $4^{2+}$, the cell membrane remains intact, providing further evidence that cell death occurs through membrane damage and not membrane lysis. However, there are indications of plasmolysis in the dead cells (for instance the internal cell leakage observed in III), indicating that $4^{2+}$ may also cause osmotic damage to the cells. The DNA damage model is further corroborated by the membrane damage assay of FIG. 30. This assay quantifies extracellular ATP after treatment with different concentrations of $4^{2+}$, relative to the polymyxin control, cells treated with $4^{2+}$ retain ATP. This is believed to be due to the need for extra levels of ATP within the cells to repair damaged DNA.

Toxicity screening, for $4^{2+}$ (FIG. 31), was completed as described above for $4^{4+}$ (FIG. 4D). $4^{2+}$ is non-toxic to *Galleria mellonella* up to 80 mg/kg (the maximum clinical daily dose for an antibiotic). As with $4^{4+}$, Mantel-cox Log-rank tests showed there was no statistical difference, at any concentration, between percentage survival for the controls and the compound treated larvae. FIG. 32 provides further toxicity screening data, this time with *A. baumannii* AB184, in these tests it is clear that the presence of $4^{2+}$ clears the colonies, as all treated larvae survive for the 120 hour duration of the experiment, whereas the larvae not treated with $4^{2+}$ do not survive. Mantel-cox Log-rank studies showed a one-star significant difference in the percentage survival between untreated infected and treated larvae. Further, FIGS. 33A and 33B show the Bacteria CFU counts from extracted larvae hemolymph (*A. baumannii* AB184 bacteria). From these plots it is clear that after 48 hours under both treatment concentrations (40 or 80 mg/kg of $4^{2+}$) the colonies were cleared. This clearance was achieved from a single compound dose. In comparison, an exponential increase in bacterial growth was observed in the absence of $4^{2+}$.

Comparison of Properties of Mono- and Di-Nuclear Complexes

To further consider the antimicrobial activity of the compounds $1^{4+}$ to $4^{4+}$ and compounds $1^{2+}$ to $4^{2+}$, compounds $4^{4+}$ and $4^{2+}$ were selected for study with a wide variety of microbes, the results are shown in Table 8 below. The MIC and MBC values were determined as above.

TABLE 8

| | | | | | | |
|---|---|---|---|---|---|---|
| MIC and MBC results in for dinuclear and mononuclear complexes ||||||| 
| Bacteria | Strain | Information and Infection caused | $4^{4+}$ | | $4^{2+}$ | |
| | | PLANKTONIC ACTIVITY PROFILE (µM) ||||||
| | | | MIC | MBC | MIC | MBC |
| *K. pneumoniae* | NCTC 13368 | Wild-type non pathogenic | 4.8 | 9.6 | 31.6 | 31.6 |
| *K. pneumoniae* | M6 | Carbapenem resistant Pneumonia, Septicaemia, Meningitis | 4.8 | 4.8 | 16 | 16 |
| *A. baumannii* | AYE | Clinical isolate, multi-drug resistant UTI, Catheter bacteremia, Nosocomial infections | 2.4 | 4.8 | 31.6 | 31.6 |
| *A. baumannii* | ATCC 17978 | Wild-type non pathogenic | 1.2 | 2.4 | 7.9 | 7.9 |
| *A. baumannii* | AB12 | Clinical isolate, multi-drug resistant UTI, Catheter bacteremia, Nosocomial infections | 1.0 | 1.2 | 3.9 | 3.9 |
| *A. baumannii* | AB16 | Clinical isolate, multi-drug resistant UTI, Catheter bacteremia, Nosocomial infections | 1.67 | 2.4 | 10.4 | 10.4 |
| *A. baumannii* | AB184 | Clinical isolate, multi-drug resistant UTI, Catheter bacteremia, Nosocomial infections | 1 | 1.6 | 3.6 | 3.6 |

TABLE 8-continued

MIC and MBC results in for dinuclear and mononuclear complexes

| Bacteria | Strain | Information and Infection caused | $4^{4+}$ | | $4^{2+}$ | |
|---|---|---|---|---|---|---|
| | | PLANKTONIC ACTIVITY PROFILE (μM) | | | | |
| | | | MIC | MBC | MIC | MBC |
| *A. baumannii* | AB210 | Clinical isolate, multi-drug resistant UTI, Catheter bacteremia, Nosocomial infections | 0.83 | 0.8 | 5.8 | 10.4 |
| *P. aureginosa* | PA01 | Wild-type non pathogenic | 4.8 | 4.8 | 15.6 | 15.6 |
| *P. aureginosa* | PA017 | Opportunistic pan-drug resistant Clinical isolate Lung infections, Septicaemia, Nosocomial infections | 2.4 | 4.0 | 15.6 | 15.6 |
| *P. aureginosa* | NCTC 13437 | Multi-drug resistant VEB type extended b-lactamase producer Lung infection, Septicaemia, Nosocomial infections | 4.8 | 9.6 | 31.6 | 31.6 |
| *P. aureginosa* | PA_007_IMP | Carbapenem resistant IMP (metallo-b-lactamase producing) Lung infection, Septicaemia, Nosocomial infections | 4.8 | 9.6 | 63.1 | 63.1 |
| *P. aureginosa* | PA_004_CRCN | Carbapenem and cephalosporin resistant Clinical isolate Lung infection, Septicaemia, Nosocomial infections | 4.8 | 9.6 | 31.6 | 31.6 |
| *E. coli* | NCTC 12923 | Wild-type non pathogenic | 2.4 | 4.8 | 7.9 | 7.9 |
| *E. coli* | PA_007_IMP | Carbapenem resistant IMP (metallo-b-lactamase producing) Pneumonia, Septicaemia, UTI | 2.4 | 4.8 | 3.9 | 3.9 |
| *E. coli* | EC958 | Multi-drug resistant extended b-lactamase producer UTI, Septicaemia, Nosocomial Infections | 1.6 | 2.4 | 3.9 | 3.9 |
| *E. coli* | MG1655 | Wild-type non pathogenic | 1.2 | 2.4 | 3.9 | 3.9 |
| *E. coli* | APEC | Multi-drug resistant avian pathogen Septicaemia, Polyserositis, Aerosacculitis | 1.6 | 4.0 | 1.8 | 3.9 |
| *B. cenocepacia* | H111 | Opportunistic, multi-drug resistant Lung infections, Nosocomial infections | 2.4 | 4.0 | 15.6 | 15.6 |
| *E. faecalis* | V583 | Vancomycin resistant UTI, GI tract infections, Nosocomial infections | 0.5 | 4.0 | 31.1 | 31.1 |
| *S. aureus* | SH1000 | Wild-type non pathogenic | 4.0 | 13.3 | 7.8 | 7.8 |
| *S. aureus* | BH1CC | Methicillin resistant Skin infections, Nosocomial infection | 38.2 | 38.2 | 11.7 | 11.7 |
| *S. aureus* | Clinical isolate | Methicillin resistant Skin infections, nosocomial infections | 19.1 | 38.2 | 7.8 | 7.8 |

As can be seen, the claimed complexes exhibit activity against a broad library of bacterial strains. In particular, both complexes exhibit high activity across all bacteria, including Carbapenem resistant strains identified by WHO as Priority 1:critical.

Tables 9 to 11 further compare the activity of complexes $4^{4+}$ and $4^{2+}$ to the clinical standards Gentamicin and Cisplatin.

TABLE 9

Biofilm activity profile results in for dinuclear and mononuclear complexes against Gram-negative biofilms

| | $4^{4+}$ | $4^{2+}$ | Gentamicin |
|---|---|---|---|
| | Biofilm Activity Profile (uM) | | |
| Bacteria | Minimum Biofilm Eradication Concentration (MBEC) | | |
| K. pneumonia | 4 | 32 | 18 |
| A. baumannii | 2 | 16 | 9 |
| P. aeruginosa | 8 | 32 | 18 |

As can be seen, both compounds are active on the Gram-negative biofilms tested—indicting that the penetrate and disrupt the biofilms. There is a higher activity with the dinuclear complex, $4^{4+}$, than either $4^{2+}$ or the clinical standard antibiotic gentamicin.

TABLE 10

Mutation Assay results for dinuclear and mononuclear complexes HPRT forward mutation assay

| Condition | Mutations | Relative Mutation Frequency |
|---|---|---|
| Untreated | 7.4 per 1 × 10⁵ viable cells | 1.0 |
| $4^{4+}$ | 29.2 per 1 × 10⁵ viable cells | 1.8 |
| $4^{2+}$ | 13.2 per 1 × 10⁵ viable cells | 2.1 |
| Cisplatin | 65.5 per 1 × 10⁵ viable cells | 10.4 |

Table 10 shows that at concentrations above the compounds MIC's the complexes were found to exhibit mutagenic frequencies in the range of the untreated control (natural mutagenesis). The mutagenic frequency was lower than that observed with Cisplatin. It is therefore confirmed that the compounds are non-mutagenic to mammalian DNA.

TABLE 11

Mammalian Cell Toxicity results for dinuclear and mononuclear complexes Mammalian cell toxicity

| Condition | HEK293 | MCR5 |
|---|---|---|
| $4^{4+}$ | 135 | 60 |
| $4^{2+}$ | 23 | 23 |
| Cisplatin | 6 | 6 |

The mammalian cell toxicity data of Table 11, shows that both compounds are less toxic than Cisplatin with the dinuclear $4^{4+}$ being over 10-fold less toxic to healthy eukaryotic cells than this well known drug. In addition, an average therapeutic index of >60 is observed for $4^{4+}$ and ~6 for $4^{2+}$. In comparison cisplatin has a therapeutic index of 2.

The relative rates of uptake for complex $4^{2+}$ and $4^{4+}$. Are shown in FIG. 25, an increase in initial rate of uptake was observed relative to complex $4^{4+}$, this is believed to be due to the lower molecular weight of the mononuclear complex.

Table 12 illustrates the kinetic solubility of complexes $4^{2+}$ and $4^{4+}$ were tested and compared to a soluble positive control drug (Nicardipine). Both compounds passed the DMPK analysis with an optimal solubility and kinetic stability.

TABLE 12

DMPK Kinetic Turbidimetric Solubility

| Compound | Nominal Concentration μM | Pass/fail | Buffer | LogS | Solubility μM |
|---|---|---|---|---|---|
| $4^{2+}$ | 200 | Pass | pH 7.4 | 0.8281 | 6.7 |
| $4^{2+}$ | 200 | Pass | pH 7.4 | 0.7961 | 6.3 |
| $4^{4+}$ | 200 | Pass | pH 7.4 | 1.138 | 13.7 |
| $4^{4+}$ | 200 | Pass | pH 7.4 | 1.138 | 13.7 |
| Nicardipine | 200 | Pass | pH 7.4 | 1.319 | 20.8 |
| Nicardipine | 200 | Pass | pH 7.4 | 1.319 | 20.8 |
| Nicardipine | 200 | Pass | pH 7.4 | 1.319 | 20.8 |

The invention claimed is:
1. A method of treating one or more microbial diseases in a patient, wherein the method comprises:
   (a) administering an antimicrobial compound according to formula (I) or formula (Ia):

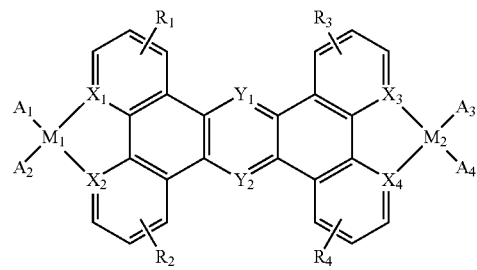

formula (I)

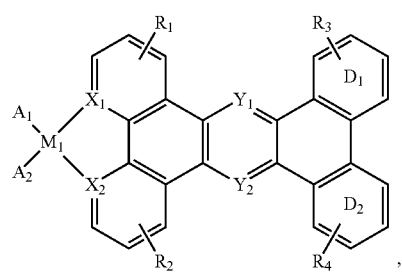

formula (Ia)

wherein,
$X_1$, $X_2$, $X_3$ and $X_4$ are each independently selected from: N, O, S;
$Y_1$ and $Y_2$ are each independently selected from: N, O, S, $C(R_a)$;
$M_1$ and $M_2$ are each a metal centre;
$R_1$, $R_2$, $R_3$, $R_4$ and $R_a$ are each independently selected from: hydrogen, alkyl, alkenyl, aryl, halogen, haloalkyl, haloalkenyl, haloaryl, hydroxy, alkoxy, carboxylic acid, amino, amido, nitro or combination thereof;

$A_1$, $A_2$, $A_3$ and $A_4$ are each bidentate ligands; and rings $D_1$ and $D_2$ each independently comprise one or more heteroatoms selected from N, O, S, $C(R_a)$;

and (b) observing a reduction in numbers of viable microbial cells.

2. The method according to claim 1, wherein the microbial disease is a bacterial disease.

3. The method according to claim 1, wherein the microbial disease is caused one or more bacterial species comprising *E. coli, A. baumannii, B. cenocepacia, P. aureginosa, S. aureus, E. faecalis,* or streptocccus.

4. The method according to claim 1, wherein the microbial disease is pneumonia, tuberculosis, cholera, syphilis, typhoid, tetanus, nosocomial infections (hospital acquired), urinary tract infections, blood stream infections, or combinations thereof.

5. The method according to claim 1, wherein the antimicrobial compound has efficacy as an antibiotic.

6. The method according to claim 1, wherein the antimicrobial compound has efficacy against gram-negative bacteria.

7. The method according to claim 1, wherein, in the antimicrobial compound, $X_1$, $X_2$, $X_3$ and $X_4$ are each N.

8. The method according to claim 1, wherein, in the antimicrobial compound, $Y_1$ and $Y_2$ are each N.

9. The method according to claim 1, wherein, in the antimicrobial compound, $M_1$ and $M_2$ are each ruthenium.

10. The method according to claim 1, wherein, in the antimicrobial compound, $R_1$, $R_2$, $R_3$, $R_4$ and $R_a$ are each independently selected from: hydrogen, alkyl and aryl.

11. The method according to claim 1, wherein, in the antimicrobial, the bidentate ligand is a compound according to formula (III):

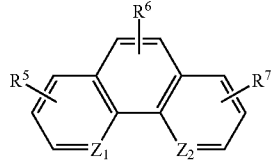

formula (III)

wherein, $Z_1$ and $Z_2$ are each independently selected from: N, O, S; and $R_5$, $R_6$, and $R_7$ are each independently selected from: hydrogen, alkyl, alkenyl, aryl, halogen, haloalkyl, haloalkenyl, haloaryl, hydroxy, alkoxy, carboxylic acid, amino, amido, nitro or combination thereof.

12. The method according to claim 11, wherein $R_5$, $R_6$, and $R_7$, in formula (III), are each independently selected from hydrogen, alkyl and aryl.

13. The method according to claim 11, wherein $Z_1$ and $Z_2$, in formula (III), are each N.

14. The method according to claim 1, wherein, in the antimicrobial compound, $A_1$, $A_2$, $A_3$ and $A_4$ are each bidentate ligands independently selected from (1) to (7):

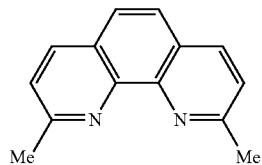
(1)

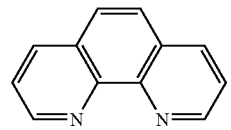
(2)

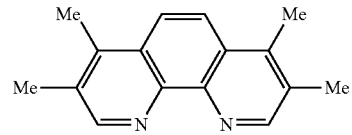
(3)

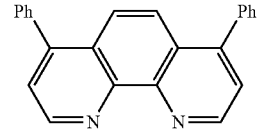
(4)

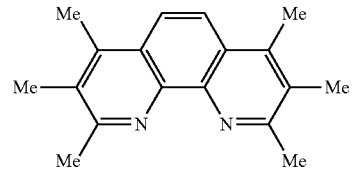
(5)

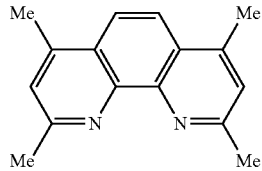
(6)

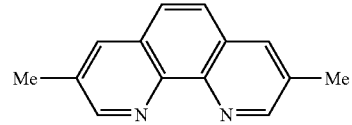
(7)

or combination thereof.

15. A method of treating one or more microbial diseases in a patient, wherein the method comprises:

(a) administering an antimicrobial compound according to formula (IV) or formula (IVa):

formula (IV)

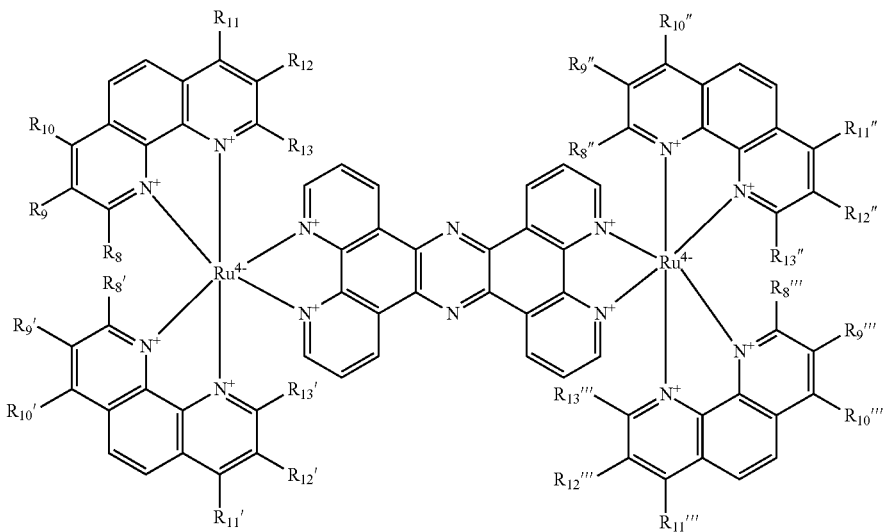

formula (IVa)

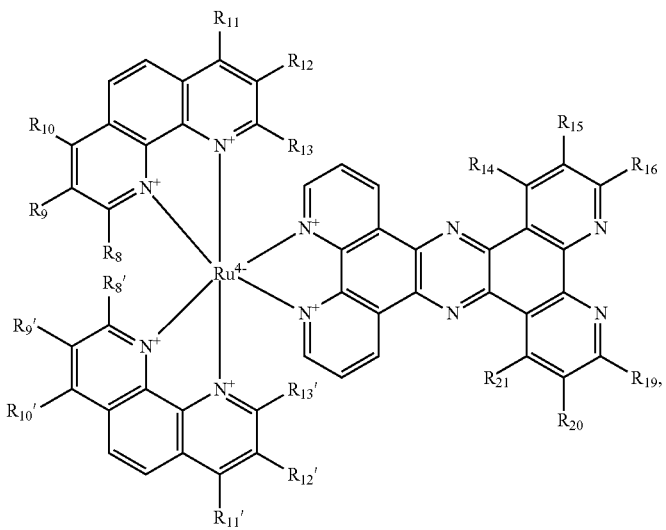

wherein, $R_8$, $R_8'$, $R_8''$, $R_8'''$, $R_9$, $R_9'$, $R_9''$, $R_9'''$, $R_{10}$, $R_{10}'$, $R_{10}''$, $R_{10}'''$, $R_{11}$, $R_{11}'$, $R_{11}''$, $R_{11}'''$, $R_{12}$, $R_{12}'$, $R_{12}''$, $R_{12}'''$, $R_{13}$, $R_{13}'$, $R_{13}''$ and $R_{13}'''$ are each independently selected from: hydrogen, alkyl, alkoxy, alkenyl and aryl;

with the proviso that at least one of $R_8$, $R_8'$, $R_8''$, $R_8'''$, $R_9$, $R_9'$, $R_9''$, $R_9'''$, $R_{10}$, $R_{10}'$, $R_{10}''$, $R_{10}'''$, $R_{11}$, $R_{11}'$, $R_{11}''$, $R_{11}'''$, $R_{12}$, $R_{12}'$, $R_{12}''$, $R_{12}'''$, $R_{13}$, $R_{13}'$, $R_{13}''$ and $R_{13}'''$ is selected from: alkyl, alkoxy, alkenyl and aryl; and wherein $R_{14}$, $R_{15}$, $R_{16}$, $R_{19}$, $R_{20}$ and $R_{21}$ are each independently selected from: hydrogen, alkyl, alkenyl, aryl, halogen, hydroxy, alkoxy or combinations thereof; and (b) observing a reduction in numbers of viable microbial cells.

16. The method according to claim 15, wherein: $R_8$, $R_8'$, $R_8''$ and $R_8'''$ are identical; $R_9$, $R_9'$, $R_9''$ and $R_9'''$ are identical; $R_{10}$, $R_{10}'$, $R_{10}''$ and $R_{10}'''$ are identical; $R_{11}$, $R_{11}'$, $R_{11}''$ and $R_{11}'''$ are identical; $R_{12}$, $R_{12}'$, $R_{12}''$ and $R_{12}'''$ are identical; and $R_{13}$, $R_{13}'$, $R_{13}''$ and $R_{13}'''$ are identical.

17. The method according to claim 15, wherein the antimicrobial compound has a structure according to formula (V) or formula (Va):

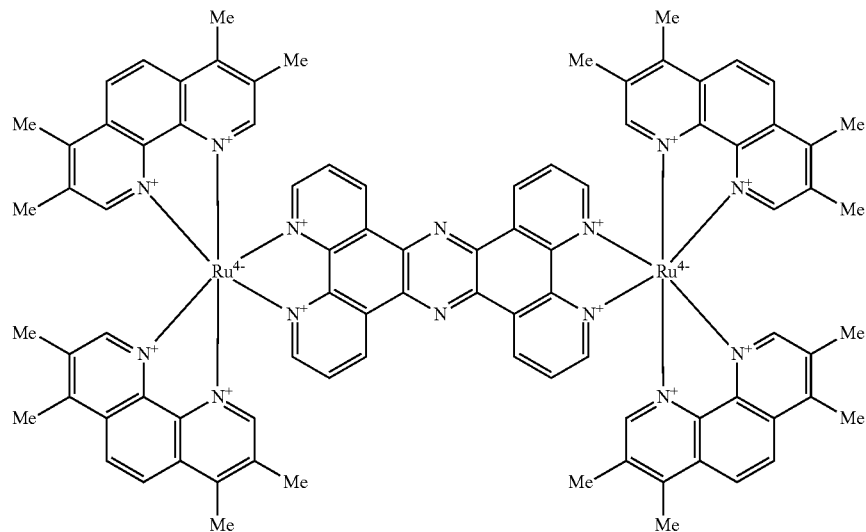
formula (V)
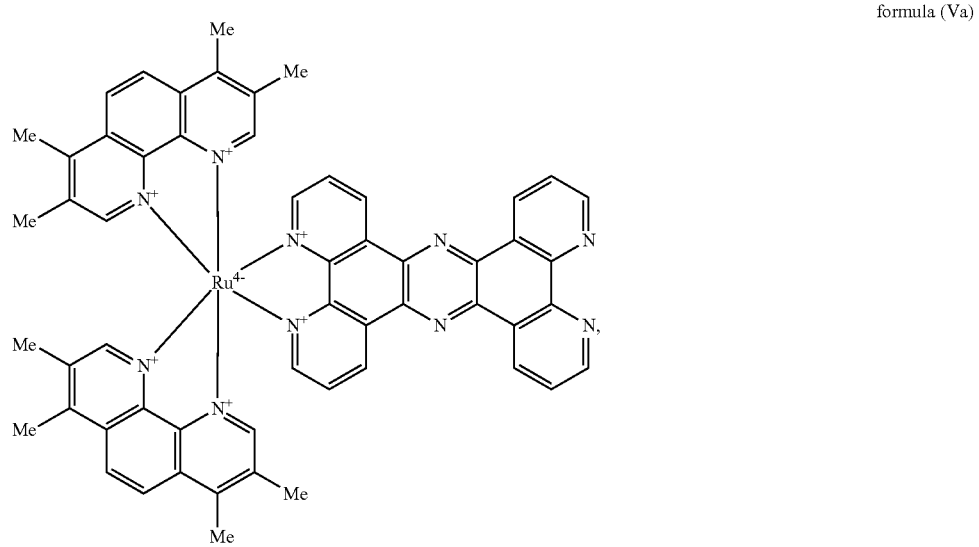
formula (Va)
or pharmaceutically acceptable salt thereof.
* * * * *